US006027722A

United States Patent [19]

Hodgson

[11] Patent Number: 6,027,722
[45] Date of Patent: *Feb. 22, 2000

[54] VECTORS FOR GENE TRANSFER

[75] Inventor: Clague P. Hodgson, Omaha, Nebr.

[73] Assignee: Nature Technology Corporation, Omaha, Nebr.

[*] Notice: This patent is subject to a terminal disclaimer.

[21] Appl. No.: 08/213,741

[22] Filed: Mar. 14, 1994

Related U.S. Application Data

[63] Continuation-in-part of application No. 08/194,208, Feb. 7, 1994, abandoned, which is a continuation-in-part of application No. 08/130,638, Oct. 1, 1993, abandoned, which is a continuation-in-part of application No. 08/097,721, Jul. 26, 1993, abandoned, which is a continuation-in-part of application No. 08/060,568, May 21, 1993, abandoned, which is a continuation-in-part of application No. 08/030,766, Mar. 12, 1993, abandoned, which is a continuation-in-part of application No. 07/968,259, Oct. 29, 1992, Pat. No. 5,354,674, which is a continuation-in-part of application No. 07/603,635, Oct. 25, 1990, abandoned.

[51] Int. Cl.$^7$ .......................... A61K 48/00; A01N 63/00; C12N 15/00

[52] U.S. Cl. .................. 424/93.21; 514/44; 536/23.1; 435/6; 435/69.1; 435/320.1; 435/325; 435/455

[58] Field of Search ...................... 514/44, 2; 435/172.3, 435/320.1, 170.1, 325, 455, 6, 69.1; 424/93.21; 935/55, 66, 62, 63, 71, 72; 536/23.1

[56] References Cited

U.S. PATENT DOCUMENTS

| | | | |
|---|---|---|---|
| 4,405,712 | 9/1983 | Woude et al. | 435/5 |
| 4,615,974 | 10/1986 | Kingsman et al. | 435/68 |
| 4,650,764 | 3/1987 | Temin et al. | 435/240 |
| 4,670,388 | 6/1987 | Rubin et al. | 435/172 |
| 4,686,098 | 8/1987 | Kopchick et al. | 424/424 |
| 4,719,177 | 1/1988 | Baltimore et al. | 435/91 |
| 4,828,987 | 5/1989 | Kopchick et al. | 435/68 |
| 4,861,719 | 8/1989 | Miller | 435/236 |
| 4,868,116 | 9/1989 | Morgan et al. | 435/240 |
| 4,873,191 | 10/1989 | Wagner et al. | 435/172 |
| 4,898,823 | 2/1990 | Kingsman et al. | 435/172 |
| 4,918,166 | 4/1990 | Kingsman et al. | 530/350 |
| 4,957,865 | 9/1990 | Samarut et al. | 435/235 |
| 4,980,289 | 12/1990 | Temin et al. | 435/235 |
| 5,075,229 | 12/1991 | Hanson et al. | 435/455 |
| 5,124,263 | 6/1992 | Temin et al. | 635/325 |
| 5,162,215 | 11/1992 | Bosselman et al. | 435/455 |
| 5,354,674 | 10/1994 | Hodgson | 435/455 |
| 5,399,346 | 3/1995 | Anderson et al. | 424/93.21 |

FOREIGN PATENT DOCUMENTS

| | | |
|---|---|---|
| 3636287 | 4/1988 | Germany . |
| 8808454 | 11/1988 | WIPO . |
| 90/07936 | 7/1990 | WIPO . |
| 92/05266 | 2/1992 | WIPO . |
| 92/07950 | 5/1992 | WIPO . |
| 93/02556 | 2/1993 | WIPO . |

OTHER PUBLICATIONS

Ngo et al., in *The Protein Folding Problem and Tertiary Structure Prediction*, 1994, Merz et al., (ed.), Birhauser, Boston, MA, pp. 433 and 492–495).
French et a., Analytical Biochemistry, vol. 228, 2:354–355, 1995.
Crystal, Science, vol. 270, pp. 404–409, 1995.
Chakraborty et al., Cancer Gene Therapy, vol. 1, 2: 113–118, 1994.
Coghlan, New Scientist, vol. 148, pp. 14–15, 1995.
Mastrangelo et al., vol. 23, 1, pp. 4–21, 1996.
Miller et al., The FASEB J, vol. 9, 190–199, 1995.
Marshall, E., "Gene Therapy's Growing Pains", *Science*, vol. 269, 1050–1055, (Aug. 25, 1995).
Mullins, J.J., et al., "Transgenesis in Nonmurine Species", *Hypertension*, 22, No. 4, 630–633, (1993).
Wall, R.J., "Transgenic Livestock: Progress and Prospects for the Future", *Theriogenology*, 45, 57–68, (1996).
Rogers, J.A., et al., "A Tumor Necrosis Factor–Responsive Long–Term–Culture–Initiating Cell is Associated with the Stromal Layer of Mouse Long–Term Bone Marrow Cultures", *Proc. Natl. Acad. Sci. USA*, 90, 5777–5780, (Jun., 1993).
"Patent Search: Genetic Vectors, Transduction, Genetic Transfection", *Oct. 1990* (a copy of a computer generated search was submitted with the PTO 1449 of the parent application.
Adams, S.E., et al., "Complete Nucleotide Sequence of a Mouse VL30 Retro–Element", *Molecular and Cellular Biology*, 8, 2989–2998, (Aug., 1988).
Anderson, W.F., "Human Gene Therapy", *Science*, 256, 808–813, (May, 1992).
Anderson, W.F., "Prospects for Human Gene Therapy", *Science*, 226, 401–409, (Oct., 1984).
Bestwick, R.K., et al., "Overcoming Interference to Retroviral Superinfection Results in Amplified Expression and Transmission of Cloned Genes", *Proc. Natl. Acad. Sci. USA*, 85, 5404–5408, (Aug., 1988).
Boeke, J.D., et al., "A General Method for the Chromosomal Amplification of Genes in Yeast", *Science*, 239, 280–282, (Jan., 1988).

(List continued on next page.)

*Primary Examiner*—Scott D. Priebe
*Assistant Examiner*—Dave Trong Nguyen
*Attorney, Agent, or Firm*—Schwegman, Lundberg, Woessner & Kluth

[57] ABSTRACT

Improved recombinant retrotransposon vectors for gene transfer are disclosed. The synthetic vectors are truncated so as to reduce or altogether eliminate homologous recombination with retroviral helper sequences found in helper cells used to propagate the vectors, making them safer for use in humans and providing more space for therpeutic genes. The vectors transmit foreign DNA efficiently, are stable, enable abundant RNA expression from the retrotransposon transcriptional promoter, and through their diversity permit many useful applications in therapeutics and transgenics. Methods are described for rescuing tissue-specific spromoters obtaining expression in primary cells, mapping the genome and other techniques of therapeutic and transgenic utility.

38 Claims, 21 Drawing Sheets

OTHER PUBLICATIONS

Carter, A.T., et al., "A Novel Approach to Cloning Transcriptionally Active Retrovirus–Like Genetic Elements from Mouse Cells", *Nucleic Acids Research*, 11, 6243–6254, (1983).

Chakraborty, A.K., et al., "Synthetic Retrotransposon VL30 Vectors For Gene Therapy, Transgenics and Research", *Miami Short Reports*, 99–100, (1994).

Chakraborty, A.K., et al., "Transmission of Endogenous VL30 Retrotransposons by Helper Cells Used in Gene Therapy", *Cancer Gene Therapy*, 1, 113–118, (1994).

Chakroborty, A.K., et al., "Synthetic Retrotransposon Vectors for Gene Therapy", *FASEB Journal, Methodology Communications*, 7, 971–977, (Jul., 1993).

Chakroborty, A.K., et al., "Synthetic Retrotransposon VL30 Derived Vectors for Gene Therapy", *J. Cell. Biol., Suppl. 17E*, Abstract No. SZ 302, 235, (1993).

Cook, R.F., et al., "Liver–Specific Expression of a Phosphoenolpyruvate Carboxykinase–neo Gene in Genetically Modified Chickens", *Poultry Science*, 72, 554–567, (1993).

Cook, R.F., et al., "Retrotransposon Gene Engineering", *Bio/Technology*, 9, 748–751, (Aug., 1991).

Cosgrove, D.E., et al., "Transgenic Animal Models and Gene Therapy", *Exp. Opin. Ther. Patents*, 4, 237–245, (1994).

Cosgrove, et al., "VL30 Vectoring Systems: Some Surprises in Their Regulation in Embryonic Stem Cells", *J. Cell. Biochem., Suppl. 17E*, Abstract No. SZ 303, 235, (1993).

Culver, K.W., et al., "Gene Therapy for Cancer", *TIG*, 10, 174–178, (May, 1994).

Donahue, R.E., et al., "Helper Virus Induced T Cell Lymphoma in Nonhuman Primates After Retroviral Mediated Gene Transfer", *J. Exp. Med.*, 176, 1125–1135, (Oct., 1992).

First, N.L., "New Animal Breeding Techniques and Their Application", *J. Reprod. Fertil., Suppl. 41*, 3–14, (1990).

Foster, D.N., et al., "Isolation of Mouse DNA Segments Containing Epidermal Growth Factor (EGF) Inducible Sequences", *J. Cell Biochem., (Suppl)*, 6, 285, (1982).

Foster, D.N., et al., "Polyadenylylated RNA Complementary to a Mouse Retrovirus–Like Multigene Family is Rapidly and Specifically Induced by Epidermal Growth Factor Stimulation of Quiescent Cells", *Proc. Nat'l Acad. Sci. USA*, 79, 7317–7321, (Dec., 1982).

Giri, C.P., et al., "Discrete Regions of Sequence Homology Between Cloned Rodent VL30 Genetic Elements and AKV–Related MuLV Provirus Genomes", *Nucleic Acids Research*, 11, 305–319, (1983).

Hatzoglou, M., et al., "Dexamethasone Regulated Expression of Mouse VL30 Retrotransposons in Rat Cells Upon Infection with Recombinant MoMLV Viruses", *J. Cell. Biochem.*, Abstract D411, 368, (1990).

Hatzoglou, M., et al., "Efficient Packaging of a Specific VL30 Retroelement by ψ2 Cells Which Produce MoMLV Recombinant Retroviruses", *Human Gene Therapy*, 1, 385–397, (1990).

Hatzoglou, M., et al., "Hepatic Gene Transfer in Animals Using Retroviruses Containing the Promoter from the Gene for Phosphoenolpyruvate Carboxykinase", *Journal of Biological Chemistry*, 265, 17285–17293, (Oct., 1990).

Hennighausen, L., "The Mammary Gland as a Bioreactor: Production of Foreign Proteins in Milk", *In: Protein Expression and Purification, vol. 1*, 3–8, (1990).

Hodgson, C.P., et al., "Gene Engineering with Retrotransposon Vectors", *Advances in Gene Technology: The Molecular Biology of Human Genetic Disease, Miami Symposia*, 44, (1991).

Hodgson, C.P., et al., "Mouse Retrovirus–Like (VL30) Transposable Element RNA is Abundantly Expressed in PSI–2 Helper Cells, Transferred to Recipient Rat Hepatoma Cells, and Expressed in a Dexamethasone–Inducible Fashion Along with Specifically Vectored Sequences: Complete Structure", *J. Cellu. Biochem.*, 13D, 54, (1989).

Hodgson, C.P., et al., "Nucleotide Sequence of Mouse Virus–like (VL30) Retrotransposon BVL–1", *Nucleic Acids Research*, 18, 673, (1990).

Hodgson, C.P., et al., "Retroviral Vectors for Gene Therapy and Transgenics", *Curr. Opin. Invest. Drugs*, 2, 205–216, (Mar., 1993).

Hodgson, C.P., et al., "Retroviral Vectors for Gene Therapy and Transgenics", *Curr. Opin. Therap. Patents*, 3, 223–235, (Feb., 1993).

Hodgson, C.P., et al., "Structure and Expression of Mouse VL30 Genes", *Molec. Cell. Biol.*, 3, 2221–2231, (Dec., 1983).

Hodgson, C.P., et al., "The Long Terminal Repeats and Associated Flanking Sequences of an Integrated Mouse VL30 Gene", *Dissertation Abstracts International*, 44, 700B, (1983).

Hodgson, C.P., et al., "The Long Terminal Repeats and Associated Flanking Sequences of a Mouse Virus–Like Genetic Element", *DNA*, 2, 83, (1983).

Hodgson, C.P., et al., "The Long Terminal Repeats and Associated Flanking Sequences of an Integrated Mouse VL30 Gene", *Doctoral Dissertation, University of Minnesota*, (Feb., 1983).

Hoeben, R.C., et al., "Inactivation of the Moloney Murine Leukemia Virus Long Terminal Repeat in Murine Fibroblast Cell Lines Is Associated with Methylation and Dependent on Its Chromosomal Position", *J. Virol.*, 65, 904–912, (Feb., 1991).

Jaenisch, R., et al., "Chromosomal Position and Activation of Retroviral Genomes Inserted into the Germ Line of Mice", *Cell*, 24, 519–529, (May, 1981).

Jaenisch, R., "Germ Line Integration and Mendelian Transmission of the Exogenous Moloney Leukemia Virus", *Proc. Nat. Acad. Sci. USA*, 7376), 1260–1264, (Apr., 1976).

Jaenisch, R., "Transgenic Animals", *Science*, 240, 1468–1474, (Jun., 1988).

Kantoff, P.W., et al., "Expression of Human Adenosine Deaminase in Nonhuman Primates After Retrovirus–Mediated Gene Transfer.", *J. Exp. Med*, 16, 219–234, (Jul., 1987).

Markowitz, D., et al., "A Safe Packaging Line for Gene Transfer: Separating Viral Genes on Two Different Plasmids", *J. Virol.*, 62, 1120–1124, (Apr., 1988).

Markowitz, D., et al., "Construction and Use of a Safe and Efficient Amphotropic Packaging Cell Line", *Virol.*, 167, 400–406, (1988).

McClintock, B., "Controlling Elements and the Gene", *Cold Spring Harbor Symp. Quant. Biol.*, 6, 197–216, (1957).

Menendez–Arias, et al., "Purification and Characterization of the Mouse Mammary Tumor Virus Protease Expressed in Escherichia coli", *J. Biol. Chem.*, 267, 24134–24139, (1992).

Miller, A.D., "Human Gene Therapy Comes of Age", *Nature*, 357, 455–460., (Jun. 11, 1992).

Miller, A.D., et al., "Redesign of Retrovirus Packaging Cell Lines to Avoid Recombination Leading to Helper Virus Production", *Molec. Cell. Biol.*, 6, 2895–2902, (Aug., 1986).

Norton, J.D., et al., "Temporal and Tissue–Specific Expression of Distinct Retrovirus–Like (VL30) Elements During Mouse Development", *Develop. Biol.*, 125, 226–228, (1988).

Rosenberg, S.A., "Gene Therapy for Cancer", *JAMA*, 268, 2416–2419, (Nov., 1992).

Rosenberg, S.A., et al., "Gene Transfer Into Humans— Immunotherapy of Patients with Advanced Melanoma, Using Tumor Infiltrating Lymphocytes Modified by Retroviral Gene Transduction", *The New England Journal of Medicine*, 323, 570–578, (Aug., 1990).

Rotman, C., et al., "Promoter and Enhancer Activities of Long Terminal Repeats Associated with Cellular Retrovirus–like (VL30) Elements", *Nuc. Acids Res.*, 14, 645–658, (1986).

Salter, D.W., et al., "Artificial Insertion of a Dominant Gene for Resistance to Avian Leukosis virus into the Germ Line of the Chicken", *Theoretical and Applied Genetics*, 77, 457–461, (1989).

Scadden, D.T., et al., "Human Cells Infected with Retrovirus Vectors Acquire an Endogenous Murine Provirus", *Journal of Virology*, 64, 424–427, (Jan., 1990).

Singleton, P., et al., *Dictionary of Microbiology and Molecular Biology*, 753–756, (1987 ed.).

Temin, H.M., "Retrovirus Variation and Evolution", *Genome*, 31, 17–22, (1989).

Vile, R., et al., "Gene Transfer Technologies for the Gene Therapy of Cancer", *Gene Therapy*, 1, 88–98, (1994).

Wagner, E.F., et al., "The Human β–Globin Gene and A Functional Viral Thymidine Kinase Gene in Developing Mice", *Proc. Natl. Acad. Sci. USA*, 78, 5016–5020, (Aug., 1981).

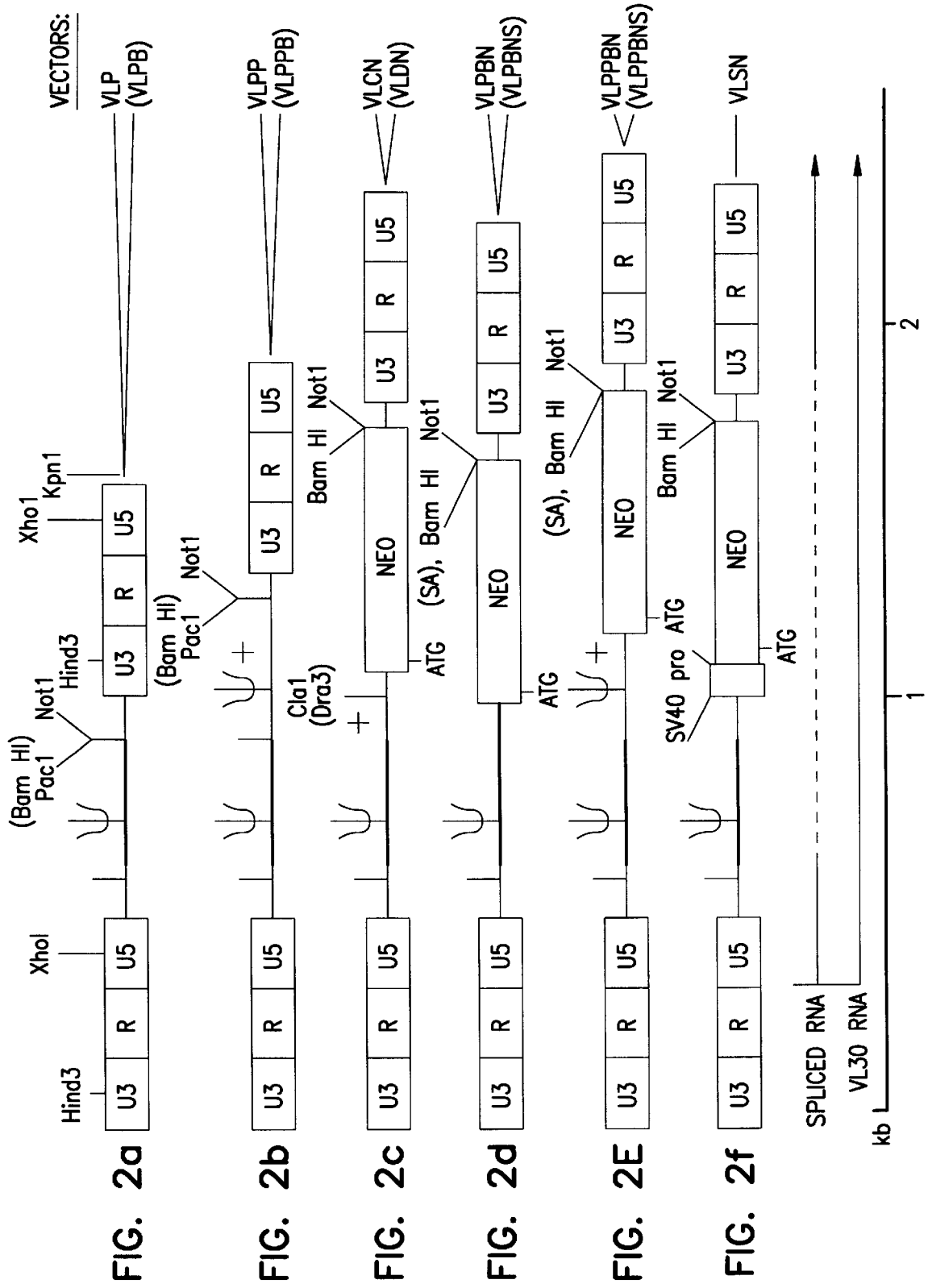

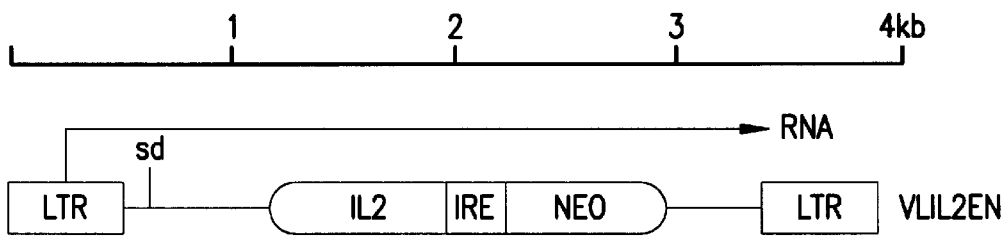
FIG. 2h1
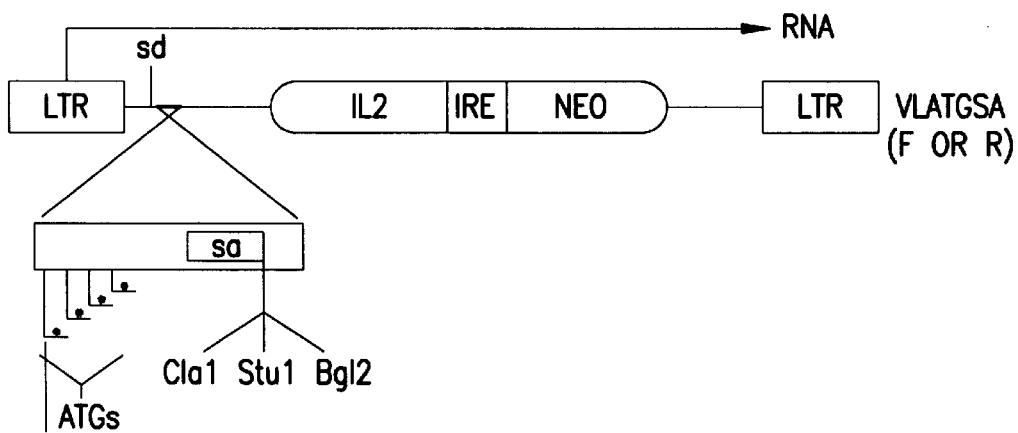
FIG. 2h2
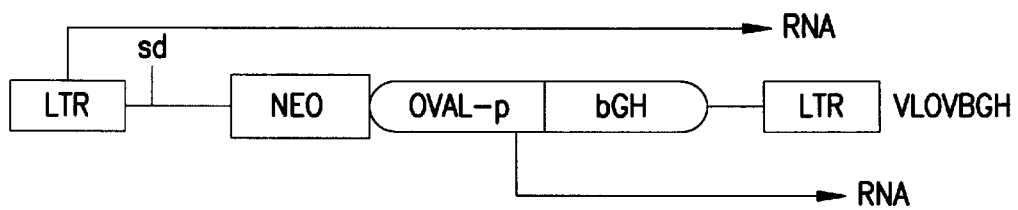
FIG. 2h3
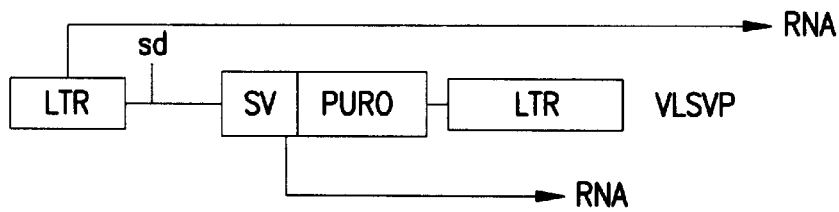
FIG. 2h4

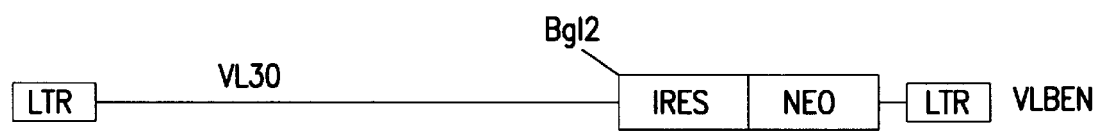
FIG. 2i1
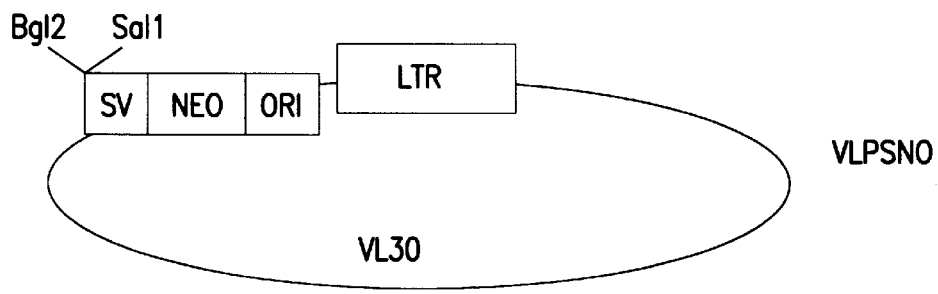
FIG. 2i2

CpG SITES IN LONG TERMINAL REPEATS

CpG SITES IN U3

MLV    17

NVL3    2

ALV (RAV-1)    6

| VECTOR | CELL LINE | NEO PROTEIN | TITER |
|---|---|---|---|
| VLPBN | GPE86 | 3.4bg/mg | 1.65 X EE4 |
| VLPPBN | GPE86 | 1.57ng/mg | 5.6 X EE4 |
| VLCN | GPE86 | 3.74ng/mg | 2 X EE5 |
| VLDN | GPE86 | 3.87ng/mg | 7.5 X EE4 |
| VLPBN | PA317 | 1.25ng/mg | ND |
| VLPPBN | PA317 | 1.92ng/mg | ND |
| VLCN | PA317 | 1.59ng/mg | ND |
| VLDN | PA317 | 1.77ng/mg | ND |

FIG. 11B

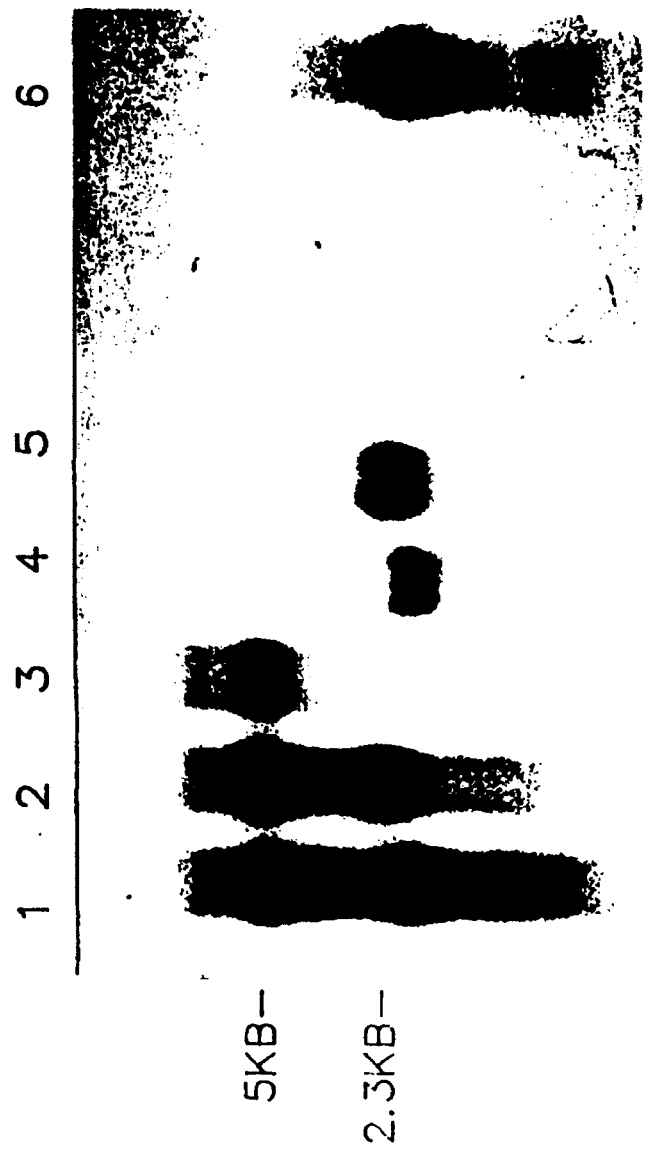

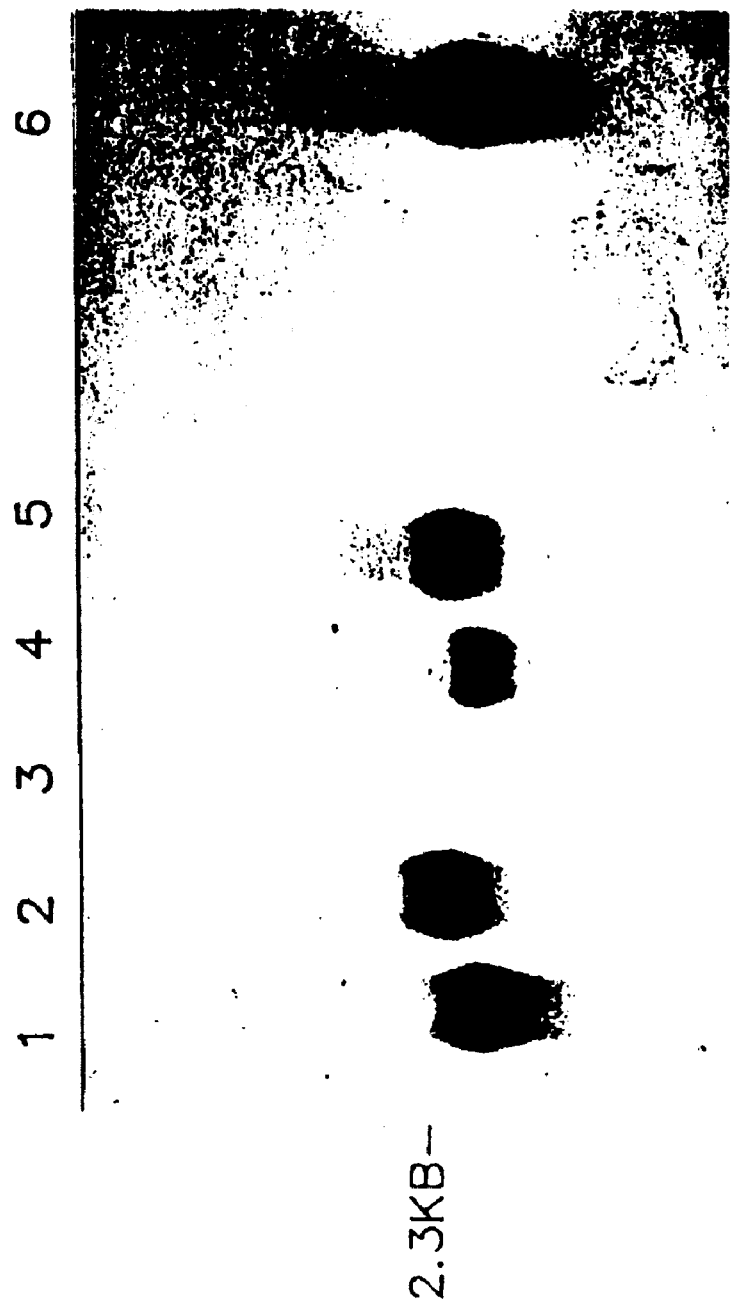

VECTORS FOR GENE TRANSFER

CROSS REFERENCES

Related Applications

The present application is a continuation-in-part of U.S. patent application Ser. No. 08/194,208, filed Feb. 7, 1994 (Attorney Docket No. CU-93-1-3B), abandoned, which in turn was a continuation-in-part of U.S. patent application Ser. No. 08/130,638, filed on Oct. 1, 1993 (Attorney Docket No. CU-93-1-3A), abandoned; which in turn was a continuation-in-part of U.S. patent application Ser. No. 08/097,721, filed on Jul. 26, 1993 (Attorney Docket No. CU-93-1-3), abandoned,; which in turn was a continuation-in-part of U.S. patent application Ser. No. 08/060,568, filed on May 21, 1993 (Attorney Docket No. CU-93-1-2), abandoned; which in turn was a continuation-in-part of U.S. patent application Ser. No. 08/030,766, filed on Mar. 12, 1993 (Attorney Docket No. CU-93-1-1) abandoned; which in turn was a continuation-in-part of U.S. patent application Ser. No. 07/968,259, filed on Oct. 29, 1992, now U.S. Pat. No. 5,354,674; and which in turn was a continuation-in-part of U.S. patent application Ser. No. 07/603,635, filed on Oct. 25, 1990, abandoned. Additionally, this application is related to an application filed with the World intellectual Property Organization pursuant to the Patent Cooperation Treaty, international application No. PCT/US91/07964, filed on Oct. 25, 1991 and published on May 14, 1992 wherein Austria, Belgium, Canada, Switzerland, Germany, Denmark, Spain, France, United Kingdom, Greece, Italy, Japan, Luxembourg, Netherlands, and Sweden were designated and elected. All of these applications are hereby incorporated herein by this reference in their entirety.

OWNERSHIP

The United States government may have certain rights in some aspects of the present invention. The parent application disclosed an invention made with United States government support under grant GM41314 from the National Institute of General Medical Sciences.

SPECIFICATION

Authorization Pursuant to 37 CFR§ 1.71(d) and (e)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The present invention relates to the fields of gene therapy, gene transfer and gene expression. It is especially useful for increasing the levels of safety and gene expression attainable from previous viral vectors.

BACKGROUND ART

Gene therapy involves the introduction of foreign genes into the cells or tissues of a patient in order to treat hereditary disorders or other diseases such as cancer or AIDS. Early successes with gene therapy have involved the use of the preferred retrovirus-derived vectors to insert genes capable of marking cancer cells, or of treating cancer, or diseases such as severe combined immunodeficiency (reviewed in Anderson, W F, 1992, Science 256:808–813). In early trials with cancer gene therapy by Rosenberg and his colleagues, two patients with advanced metastatic melanoma experienced remission after gene therapy (Rosenberg, S A, 1992, J. Amer. Med. Assoc. 268,2416–2419). However, it is difficult and often impossible to achieve acceptable levels of expression for prolonged periods from such retroviral vectors.

Until recently, gene therapy experiments have taken place only after extensive review, and only a limited number of patients have been treated. A primary reason for such caution stems from the problems associated with the use of retrovirus-derived vectors used to deliver the genes into the cells and chromosomes of the recipient. The most difficult problem has been the ability of the retrovirus-derived vector to genetically recombine with related, retrovirus-derived helper gene sequences present in the donor cell. The combination of the retrovirus vector sequences plus the retrovirus helper sequences together comprise nearly the entire viral genome. When these two parts recombine, the result is an infectious and oncogenic virus which is capable of developing into a full-blown infection, leading to characteristic viremia and cancers in mice and primates. For example, three monkeys undergoing gene therapy trials at The National Institutes of Health died from lymphomas that were subsequently traced to recombination events within the cells used to propagate the virus (Donahue, R E, et al, 1992, J. Exptl. Med. 176, 1125–1135). In addition, retroviral vectors are often transcriptionally silenced after entering the cell. It has been noted that cells of mammals often attach methyl groups to certain regions (called CpG islands) of the viral promoter DNA, apparently preventing the transcription of RNA (Hoeben, R C et al, 1991, J. Virol., 65:904–912). This methylation of CpG residues has been postulated to be primarily a host defense mechanism for eliminating expression from foreign DNA entering the cell, such as a virus. Unfortunately, it also reduces expression from viral vectors used to deliver therapeutic genes, and thus reduces their effectiveness. This problem may be overcome through the use of vectors which are not foreign to cells.

It would be very desirable to invent vectors which have no homology to viral helper sequences, thus preventing the possibility of homologous recombination leading to the production of a replication competent virus. Second, it would be desirable if vectors could be used which have no oncogenic phenotype, or at least a greatly reduced oncogenic phenotype. Thirdly, it would be best if the vectors had a transcriptional promoter with enhanced capability for producing regulated expression in cells. Fourthly, it would be best if the vectors lacked CpG methylation 'islands' in their transcriptional promoters, and are normally expressed in living tissue. Finally, it would be best if the vector was made suitable and convenient for human gene therapy, by reducing the load of unnecessary genetic sequences (thus providing more space for foreign therapeutic genes), by including useful cloning and regulatory sites, and by making the vector generally amenable to change, permitting it to be easily adapted for delivery of a wide variety of genetic material. If all these goals could be attained, human gene therapy would be made much safer, and more efficacious. This, in turn, would permit the widespread implementation of gene therapy among afflicted groups of individuals, such as the million or so persons who die of cancer each year in the United States alone. Thus, the implementation of gene therapy as a lifesaving technology will require not one, but several technical improvements over the retroviral vectors currently available.

Limited progress has recently been reported in reaching these theoretical goals. For example, Temin and his colleagues have been successful in combining viruses of different origins in order to decrease homology and homologous recombination in helper cells (U.S. Pat. No. 5,124, 263). The oncogenic transcriptional promoter was inactivated by making a deletion at the 3'-end of the virus vector. These changes, combined with the use of safer helper cell lines (U.S. Pat. No. 5,124,236), did decrease the rate of homologous recombination although the resulting viral titers have been disappointing. Others have devised safer helper cell lines in which there is less overlap and homology between the nucleic acid sequences which make the viral genes for transmission (Markowitz et al, 1988, J. Virol. 62, 1120–1124; Markowitz et al, Virology 167, 400–406; WO9205266). Titer is very important since it limits the effectiveness of the viral infection, and the highest titers are attained with retroviral vectors which have a large portion of the gag helper gene sequence intact, thus increasing the level of homologous recombination and RCR. This problem can be partially overcome by introducing multiple mutations in the viral gag gene, however the vectors can still participate in homologous recombination, and they generally have fully-oncogenic transcriptional promoters. The background of retroviral vectorology together with recent advances in patented vectors and public domain technology have recently been reviewed by the applicant (Hodgson, C P, 1993, Curr. Opin. Thera. Patents, 3:223–235.), a copy of which is appended and which shall be referred to in this application, together with other references, as if fully set forth.

Previously, the applicant filed patent applications (pending) covering the Method of Gene Transfer Using Retrotransposons (USA/07/603,635, Oct. 25, 1990, and subsequent continuation application; also WO 92/07950), which described the first use of a nonviral mobile genetic element (VL30) for intercellular gene transfer and expression. Previous vectors had used replication-competent or defective viruses derived from a replication-competent oncogenic virus family, thus facilitating recombination and oncogenesis. The vector of choice until now, Moloney murine leukemia virus (MoMLV), is also the vector most commonly used in helper cell lines, including those currently being used in human gene therapy (Miller, A D, and Buttimore, C, 1986, Mol. Cell. Biol. 6:2895–2902; (U.S. Pat. No. 4,861,719). The instant invention describes new retrotransposon VL30 vectors which are made useful for human gene therapy through a number of modifications and improvements.

The use of transposable genetic elements for gene therapy is a natural extension of their evolutionary importance, first described by McClintock (McClintock, B, 1957, Cold Spring Harbor Symp. Quant. Biol. 21:197–216), and represents a fundamental departure from the use of pathogenic agents for gene therapy vectors in the past.

The mobile element VL30 vectors which the applicant described in his previous application were made from a mouse retrotransposon which is present at 100–200 copies in the germ line of mice. The LTR transcriptional units and complete genomes of some of these genes in mice have been characterized by the applicant and others (Hodgson, C P et al, 1983, Mol. Cell. Biol. 3:2221–2231; Adams, S E, et al, 1988, Mol. Cell. Biol. 8:2989–2998; Hodgson, C P, et al 1990, Nucleic Acids Res. 18:673), and transcription from the LTR promoter has been observed by a variety of methods in cell culture, including reporter genes, RNA blotting techniques, etc. (Norton, J D, and Hogan, B L, 1988, Dev. Biol. 125:226–228; Rotman, G, et al, 1986, Nucleic Acids Res. 14:645–658). Comparison of VL30 to other types of transposable elements such as those found in Drosophila (fruitfly) and yeast indicated that they had features in common such as primer binding sites. This suggested that they replicated in a manner similar to retroviruses. But the elements found in great abundance in yeast, mouse, and Drosophila had a remarkable lack of disease phenotype compared to retroviruses. The mouse VL30 genomes sequenced to date have no viral structural genes (see Adams et al, 1988 supra; also Hodgson et al, 1990, supra).

Instead, they contain an internal conserved sequence of unknown function, which does not appear to contain any long open reading frames. Unlike MoMLV proviruses, they are abundantly expressed in vivo. In this disclosure, we demonstrate for the first time that a surprising amount of the internal sequences can be removed and replaced with facilitating sequences or additional useful genes which can be delivered by the VL30 and expressed in recipient cells, without negative effects on transcription. This in turn permits more genetic material to be added later. Despite their notable lack of phenotype, VL30 genes are capable of mobilizing in the presence of retrovirus infection, or in retroviral helper cells, using their innate ability to copackage into the viral particle to escape from the cell genome and enter a new host cell during viral transmission. Thus, they provide an additional means for the transmission of nonviral genetic information. This information may then be transmitted to a different location within the same cell, to different cells of the same organism, into the germline, to cells in different organs, or between organisms or between species.

INDUSTRIAL VIABILITY

Accordingly, in addition to the objects and advantages of the retrotransposon vectors described in my previous patent application, the present invention provides additional commercial and industrial attributes, for example, providing:

(a) a much smaller vector, capable of transmitting and expressing a proportionately larger amount of insert DNA;

(b) a variety of facile cloning sites, selectable marker genes, transcriptional promoters, and/or reporter genes to enable direct visualization of expression;

(c) a method for developing tissue-specific, developmental-specific, or hormonal-specific expression by trapping the promoter of choice from the expressing cell;

(d) a method of delivering a toxic or rearranged gene to a recipient cell such as a cancer cell, without affecting the delivering cell or other cells which are not direct targets for gene insertion;

(e) a demonstrated method and a strategy for devising vectors which are entirely synthetic products, made by combining the highly specific coding inherent in synthetic oligonucleotides with the specificity now attainable from various gene amplification techniques, such that a biologically active vector can be made to suit exactly the sequence desired by the artisan, rather than by using the less precise method of subcloning available restriction fragments from DNA grown in living organisms, as was the state of the art prior to the instant invention; and (f) a method of eliminating all but a few base pairs of homology to retroviral helper systems, thus, preventing recombination events which could lead to replication competent retrovirus.

Still further industrial attributes will become apparent from a consideration of the ensuing description and drawings.

DISCLOSURE OF THE INVENTION

The general method and several preferred embodiments of the present invention are seen in FIGS. 1 and 2. One such embodiment (FIG. 2a) includes a greatly reduced VL30 retrotransposon genome, in which nearly all of the nonessential VL30 sequences were absent. In the examples shown, extensive synthetic oligonucleotide sequences have been used in combination with primer sequences to make vectors by gene amplification. Most of the nonessential sequences of the VL30 prototype, NVL3, have been eliminated in the process, resulting in short, functional vector sequences containing synthetic restriction endonuclease sites for the insertion of one or more foreign genes and/or transcriptional promoters or other regulatory sequences. FIG. 2b shows a similar vector which has a slightly larger packaging region (+), and a similar multiple cloning site. Some advantages of the overall strategy are: (1) reduction in the amount of VL30 sequences needed to transmit the vector, permitting a concomitantly larger amount of foreign genetic material to be used and eliminating homologous recombination sites; (2) inclusion of multiple cloning sites, which permits more than one gene to be included, said gene(s) to be transcribed from either the LTR promoter or from an internal promoter, or both; (3) the inclusion of splicing signals to permit possible expression of two types of genetic information (spliced or unspliced) which may be used to express two genes from the vector promoter; (4) an increase in the expression of RNA attainable through the reduction of internal sequences; and (5) a new use for a patented process (polymerase chain reaction U.S. Pat. No. 4,683,202), which provides the construction of complete, biologically active vector sequences capable of transmission, expression and replication.

Previously it was apparently not known that gene amplification could be used to make large, biologically active vectors. This is because gene amplification is an error prone process (Saiki, R K, et al, 1988, Science 239:487–491), resulting in buildup of mutations over many rounds of gene amplification, as well as through errors at the ends of molecules and primer artifacts. However, by carefully gel-purifying the desired products repeatedly during the gene construction process as disclosed in techniques and materials, and by "polishing" the ends of fragments by restriction endonuclease cleavage near the ends, the present invention achieves bioactive vectors which were constructed entirely out of synthetic (oligonucleotide and in vitro-amplified) products. The advantage of this approach is the precision which it allows in synthesis, in contrast to the less precise method of conventional endonuclease digestion/ligation types of recombinant DNA technology which have been used to construct most biologically active portions of the vectors previously used. Only the exact sequences desired have been included in the instant invention.

In a preferred form, a selectable gene (neomycin phosphotransferase) was cloned into the multiple cloning site (FIGS. 2c through 2f), permitting selection of the recipient cells with the drug G418. Using this type of VL30 vector, the genes could be passaged repeatedly without evidence of rearrangement. The selectable gene was also adapted so that it could be efficiently expressed as protein either from the long terminal repeat transcriptional promoter (LTR) (permitting another therapeutic gene to be driven from an additional inserted promoter) (FIGS. 2a through 2e), or so that the selected gene could be driven from another promoter such as the SV40 promoter illustrated in FIG. 2f, permitting the additional (therapeutic) gene to be expressed from the powerful VL30 promoter. The vectors were designed so that the favorable ATG start codon which the investigator inserts (along with structural genes) into the multiple cloning site (MCS) was the first such favorable codon, thus permitting good expression of the inserted gene. In contrast, murine leukemia virus-derived vectors have multiple ATG codons preceding the translational start site, some of which may have a purine base three nucleotides before the ATG. Even the previously described VL30 vectors had such a site prior to the unique site available in such vectors. Such preferred start sites may confound translation of the desired gene from the LTR promoter in conventional retroviral vectors. The methods used here permit the user to now easily insert a gene containing the first favorable context for ATG start sites.

In another preferred embodiment, a multiple cloning site is included. One example of how the invention containing such a site may be utilized by the artisan is illustrated in FIG. 2g. An insert with a preferred-context ATG codon is included (the latter includes an Nco1 unique cloning site to permit translation of an inserted sequence), possibly with a typical reporter gene (β-galactosidase), and or a common selectable marker such as zeocin (drug resistance), which can be a fusion protein with β-galactosidase. In the particular modification shown, the relative level of expression from the VL30 LTR promoter may be determined by staining the cells with x-gal, a colorless material which is converted to a blue dye by the β-galactosidase enzyme. This enables the investigator to perform regulatory studies in cultured cells or organs of animals and to visualize the results by conventional microscopy. For additional specificity, a nuclear localization sequence permits the staining by the enzyme to be confined mostly to the nucleus.

Other preferred VL30 vectors are shown, including the deposited enabling prototype, VLPPBN, which contains in addition to the minimal packaging region, a cluster of repeats resembling RNA polymerase 3 promoters, including the so-called B box motif. These are useful regulatory elements, in that they may permit either alternative RNA transcription by RNA polymerase 3 or other enzymes, or by acting as primer binding sites for reverse transcription (the sequences are complementary to tRNA ends which in turn have been shown to act as primers for reverse transcription). One modification includes a single copy of the repeated sequences (instead of four copies found in VLPPBN) and another includes one copy interrupted by an 8bp sequence which is also a unique cloning site for the insertion of genetic material (VLDN and VLCN, respectively, FIG. 2d) These forms of the vectors enable regulatory effects to be determined in cells.

Another aspect of the invention as disclosed is the ability to copy additional VL30 or other retroelement LTRs from the genome or cloned sequences from any species harboring them. The gene amplification methods disclosed herein will additionally permit selective gene amplification of an LTR, by including in the primers the highly conserved VL30 LTR termini. Thus, it is possible for an average person skilled in the art, using the primers shown or others similar to them, to copy an LTR from genomic or cloned DNA, as disclosed herein. For example, some VL30 elements (such as NVL1 and NVL2) respond to epidermal growth factor stimulation or oncogenic transformation (the latter useful as a tumor-specific promoter for use in inactivating cancer cells). Such specific promoters may be copied from complementary DNA made from RNA in the cell type or stimulated cell condition which is specific for them (commercial kits and instructions for reverse PCR are available from Cetus Perkin-Elmer Corp. Emeryville, Calif.). Or, the complete set of complementary VL30 promoters may be amplified from cell DNA from mouse using conventional PCR. The primers together with the vectors and gene amplification methods described herein, enable the facile insertion and conveyance of the promoter to the left side of the genome, from which it may direct expression of the included genetic sequences (FIG. 3). Many new promoters may be derived from the disclosure of the present invention specificities from the many VL30 and other mobile genetic elements present in cells of various types, which promoters will respond to a particular developmental, spatial, temporal, or hormonal condition and which would be useful for imparting expression in a like manner in other cells. Thus, it is not necessary to understand the reasons for specific expression from a particular VL30 promoter in order to clone and immediately use this technique of LTR promoter capturing described here. In this technique, the vector used to capture the promoter is adapted as a gene therapy vector also, since during retrotransposon transmission, the promoter (U3) region of the LTR at the 3'-end of the vector is also copied to the 5'-end, making both LTRs uniform. By isolating the amplified LTR gene fragment from a gel, digesting it with the two enzymes shown (Not1 and Kpn1), and reisolating the fragment from another gel, it will automatically directionally clone into the similarly digested and purified vector fragment, such as VLPPBN.

In yet another preferred embodiment, the right LTR is further modified by the elimination of some U3 (promoter) region sequences, and by the addition of a multiple cloning site (FIG. 4). This enables either its immediate use (as a null promoter upon transposition, but not before), or else as the site into which virtually any promoter-enhancer type of element may be inserted, either individually or in a number greater than one in either forward or backward orientation. Another use of this embodiment is to permit any gene, (for example encoding a toxic molecule) to be delivered to a cell such as a cancer cell without inflicting toxicity upon the delivering cell. In this applied use, the recipient cell is transfected or the VL30 gene is otherwise introduced in a manner which also permits its use as a helper cell (i.e., through the co-introduction or successive introduction of viral helper sequences). The vector contains the 3'-LTR cassette bearing the genetic sequences encoding a synthetic exon 1 of a toxin such as the ricin A chain (or a similiar toxin, such as dyphthera toxin), together with LTR promoter sequences. The recipient cell will not produce a toxic molecule because its exon 2 is upstream of exon 1 (i.e., in reverse order), but will package and export RNA in which the 3'-end of the RNA will become reverse transcribed into DNA in which the 5'-LTR now contains exon 1, thus making it capable of producing an intracellular toxin only in recipient cells. An example of this embodiment would be a tumor infiltrating lymphocyte from a cancer patient, which transmits viral particles bearing the toxic ricin gene. After the recipient cell in the tumor dies from the toxin, the formerly toxic molecule becomes nontoxic in the extracellular environment because it lacks the second polypeptide chain which makes it capable of entering a separate cell. However, if it is transferred to an adjacent tumor cell by a gap junction or other intercellular connection, it will toxify that cell also. This mechanism, and other poorly understood mechanisms will amplify the killing effect. The system is autoselecting during creation of TIL cells bearing the foreign genes. This is because uninfected TIL not bearing the toxic construct will be killed by infection from the helper TIL. However, the helper-cell TIL will not be killed due to the principal of viral exclusion, which prevents superinfection by another viral particle producing TIL with the same envelope subtype (for example, amphotropic envelope). Thus, toxic molecules can be delivered safely to specific targets by tumor infiltrating lymphocytes, similar to current methods of TIL gene therapy. After the TIL find their way to the tumor site and infect tumor cells, these infected cells will die along with uninfected tumor cell which are killed due to the so called "bystander effect" (WO93/02556, Freeman, et al.). This embodiment is but one example of delivery of a gene or gene product to a recipient cell without concomitant expression in the donor cell.

The present invention enables those skilled in the art to insert a cloned gene into a unique site, to transfect the vector into viral helper cells, to harvest the virus from the helper cells, to infect progeny cells with the viral particles containing the vectors described here and their derivatives, and to select recipient cells which produce the products of the inserted genes. A particular advantage of the present invention has to do with the size of the vectors. For example, the vector VLPPB shown in FIG. 2*b* has only one and 3/10 kilobase of RNA transcribed, yet we have shown that it is fully capable of transmitting expressible genetic information via the viral particle, of reverse transcribing the vector genome into double stranded DNA, of inserting into the DNA of the recipient cell, and of expressing genetic material from the LTR transcriptional promoter. The vector VLPB (FIG. 2*a*) is also effective, and has only approximately 1.059 kilobase of RNA transcribed. This is the smallest retrovector known to us. In addition to reducing opportunities for homologous recombination which would otherwise render the vectors dangerous to use in man, the size of the vector permits a larger gene to be inserted without exceeding the 10–11 kb packaging limit of the viral particle. For example, a dystrophin minigene for the treatment of muscular dystrophy (6–9 kb) may be inserted into this vector. An additional advantage is that because there are no retroviral genes present, it is not necessary to inactivate the 3'-LTR in order to prevent certain oncogenic effects such as those associated with replication-competent retroviruses and derived viral vectors such as spleen necrosis virus and MoMLV. This in turn also permits the vector to be safely amplified using the ping-pong technique (WO88/08454) which has been shown to increase titer (under certain conditions) when retrovirus vectors were used. Another advantage is that there are only two CpG methylation sites in the U3 promoter region, compared to seventeen in Moloney murine leukemia virus-derived vectors. This is not sufficient to create an island for binding by methyl binding inhibitory proteins which generally requires 8–12 CpG residues in a localized region or island to be effective. Thus, VL30 genes are expressed in vivo whereas retroviral genes are frequently silent.

Although the description contains many specificities, these should not be construed as limiting the scope of the invention but as merely providing illustrations of certain exemplary embodiments of the present invention.

Certain objects of the present invention, therefore, include:

a. providing a retrotransposon vector of the above kind which may be used to introduce genes into cells, tissues, or organisms where the foreign gene(s) is (are) expressed from a simplified mobile genetic element such as VL30 which does not contain viral structural gene sequences, using either the LTR transcriptional promoter of the mobile element, or else the internal promoter provided by the investigator; and b. providing a progeny stock of the above kind, c. providing a method for the production of like kind from a variety of viral and nonviral sources.

These and other objects and advantages of the instant invention will become apparent from the specifications which follow. The description of the preferred embodiments with reference to the accompanying drawings will make it possible for a person of average skill to reproduce the invention in a manner useful for a variety of applications such as gene therapy wherein it is important to use materials allowing the efficient and faithful transmission of large genes for expression at significant levels.

The scope of the invention should be determined by the appended claims and their legal equivalents, rather than by the examples given.

BRIEF DESCRIPTION OF THE DRAWINGS

In the drawings, closely related figures have the same number but different alphabetical suffixes.

FIGS. 2a through 2g, 2H1–2H4 and 2i are diagrammatic illustrations which show maps (a through i) of vectors intended for general applications;

FIGS. 4 and 5 are diagrammatic illustrations which depict a method for introducing a gene which produces a toxic or rearranged gene product in the recipient, but not the donor cell;

FIG. 11B is a table showing relative titers and expression of proteins by synthetic vectors;

FIGS. 12A, 12B, 12C, and 12D are black and white photographs of VL30 RNA expression in various cell types; and FIGS. 13A, 13B, and 13C are black and white photographs, wherein FIG. 13A illustrates an RNA blot showing expression of a number of vectors, while FIGS. 13B and 13C illustrate a gel showing insertion of a VL30 vector into chicken DNA in vivo.

BEST MODE FOR CARRYING OUT THE INVENTION

1. Definitions

Figure 1:
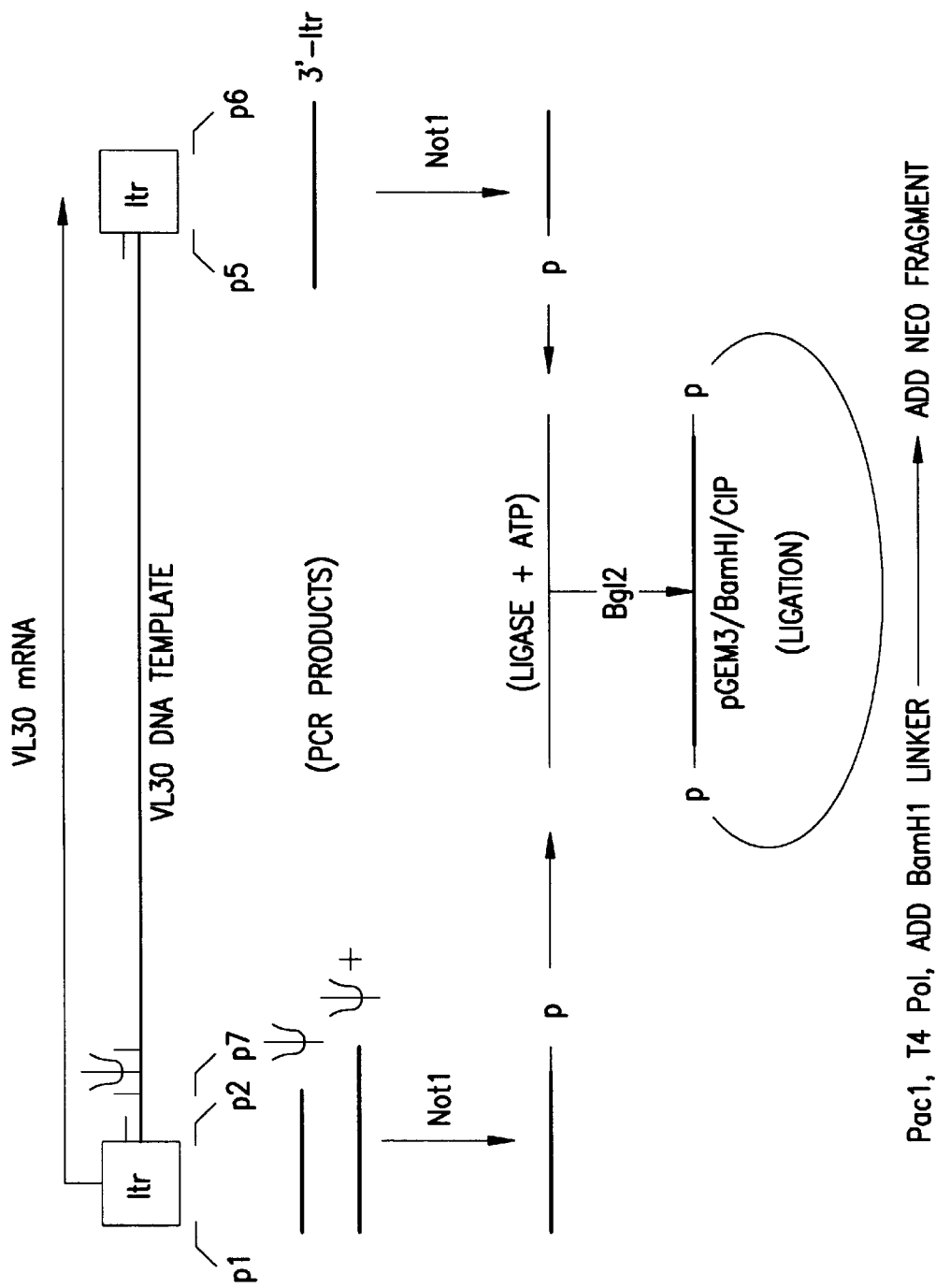
FIG. 1 is a diagrammatic illustration which shows a method and strategy for constructing vectors using as the example the vectors VLP and VLPP.

The following definitions of biological and genetic terms will be useful in understanding this invention:

DNA: Deoxyribonucieic acid, the genetic material of cellular chromosomes.

RNA: Ribonucleic acid, the genetic material of the RNA tumor viruses and retrotransposons during part of the life cycle.

DNA sequence: A linear sequence comprised of any combination of the four DNA monomers. The DNA monomers, nucleotides of adenine, guanine, cytosine and thymine code for genetic information, including coding for an amino acid, a promoter, a control or a gene product. A specific DNA sequence has a known specific function, for example, codes for a particular polypeptide, a particular genetic trait or affects the expression of a particular phenotype.

Gene: The smallest, independently functional unit of genetic material which codes for a protein product or controls or affects transcription and comprises at least one DNA sequence.

Chimera: A hybrid gene produced by recombinant DNA technology; also refers to an animal which has normal cells as well as genetically engineered cells containing a vector (also called a mosaic animal).

Genotype: The genetic constitution of a cell or organism.

Phenotype: A collection of morphological, physiological and biochemical traits possessed by a cell or organism that results from the interaction of the genotype and the environment.

Phenotypic expression: The expression of the code of a DNA sequence or sequences which results in the production of a product, for example, a polypeptide or protein, or alters the expression of the zygote's or the organism's natural phenotype.

Chromosome: A fiber or threadlike structure which is completely or partially composed of genetic nucleic acid.

Retrovirus: A virus which requires reverse transcription of RNA into DNA at some point during its life cycle; specifically the retroviridae, or RNA tumor viruses. This family encompasses all viruses containing an RNA genome and RNA-dependent DNA polymerase (reverse transcriptase).

Retrotransposon: A cellular, movable genetic element with long terminal repeats.

Vector: Usually an agent transmitting a disease or natural genetic information; here restricted to a genetic agent transmitting a foreign gene (DNA or RNA) construct, unless other indicated.

Genome: One set of chromosomes, haploid or diploid, for an agent or organism.

Transduction: Here limited to the transmission of viral, retrotransposon, or exogenous (added) genes (unless otherwise indicated by means of viral particles or viral functions).

Helper Cell Line: In this context, a cell line which has been genetically engineered or which naturally contains genes capable of generation of some or all necessary retroviral trans-acting functions or proteins, such as reverse transcriptase, viral core proteins, envelope glycoproteins, and/or tRNA for priming reverse transcription and the like. Examples of helper cell lines include psi2, or "ψ2" PA317.

Replication Competent Retrovirus: A retrovirus which bears all genes necessary for cis and trans functions; complete, able to replicate without additional viral functions.

Non-replication competent (defective) retrovirus: A retrovirus which requires supplemental functions in order to replicate, or which is unable to replicate by itself. In this context, it usually requires trans acting functions such as named above.

Transgene: A foreign gene, usually inserted into a vector.

cis-acting element: Genetic element which must be located on the same piece of nucleic acid in order to function, such as transcriptional promoter or enhance elements, primer binding sites and the like.

trans-acting element: Genetic element which need not be located in cis, i.e., that which may be located elsewhere, such as in the cellular genome. Examples of trans elements are the retroviral core protein, polymerase, and envelope glycoprotein genes.

Psi sequences: Sequences of genetic information which encode the packaging functions which enable particles to package and transmit viral or retrotransposon RNA, also called encapsidation or packaging sequences.

RCR: replication-competent retrovirus.

CpG: a linear DNA sequence consisting of a deoxycitidine residue followed by a gaunosine residue, or 5'-CG-3'.

VL30: a retrotransposon sequence from the VL30 family, consisting of long terminal repeats separated by 3–5 kb of internal DNA sequences, which are found integrated at 100–200 copies in the chromosomal DNA of most mus species.

NVL3: a particular VL30 genetic sequence from the mouse, described by Carter et al., supra, and sequenced in entirety by Adams et al supra.

PCR: the polymerase chain reaction, a patented technique for the amplification of gene.

Gene amplification: refers to any of a number of techniques for in vitro increasing the copy number of a genetic sequence.

dNTPs: deoxyribonucleotide triphosphates, the four precursors to DNA (dCTP, dATP, dGTP, TTP).

MoMLV: Moloney murine leukemia virus, an oncogenic retrovirus of mice which is often used as a vector for gene transfer and gene therapy.

ALV: Avian leukosis virus, and avain retrovirus sometimes used as a vector for gene transfer.

SNV: Spleen necrosis virus, another retrovirus sometimes used in vector construction.

neo: The neomycin phosphotransferase gene, which imparts neomycin drug resistance in prokaryotic organisms, and G418 drug resistance in eukaryotic organisms.

ATCC: The American Type Culture Collection, of Rockville, Md., U.S.A., a depository for strains such as the patented helper cell PA317, which can be used to enable the instant invention.

PuXXATG: refers to a translational start codon (ATG) which is preceded three base pairs by a purine base-containing nucleotide, making this ATG a favorable context for the start of translation.

amphotropic envelope: refers to a viral envelope glycoprotein subtype which is capable of infecting human cells, and cells of many other species.

retrovector: any vector transmitted using reverse transcriptase to copy an RNA template into DNA (i.e., retrotransposon vectors, retrovirus-derived vectors, synthetic vectors, retroposon vectors, etc.).

2. Description of FIGS. 1 through 11

Figure 2G:
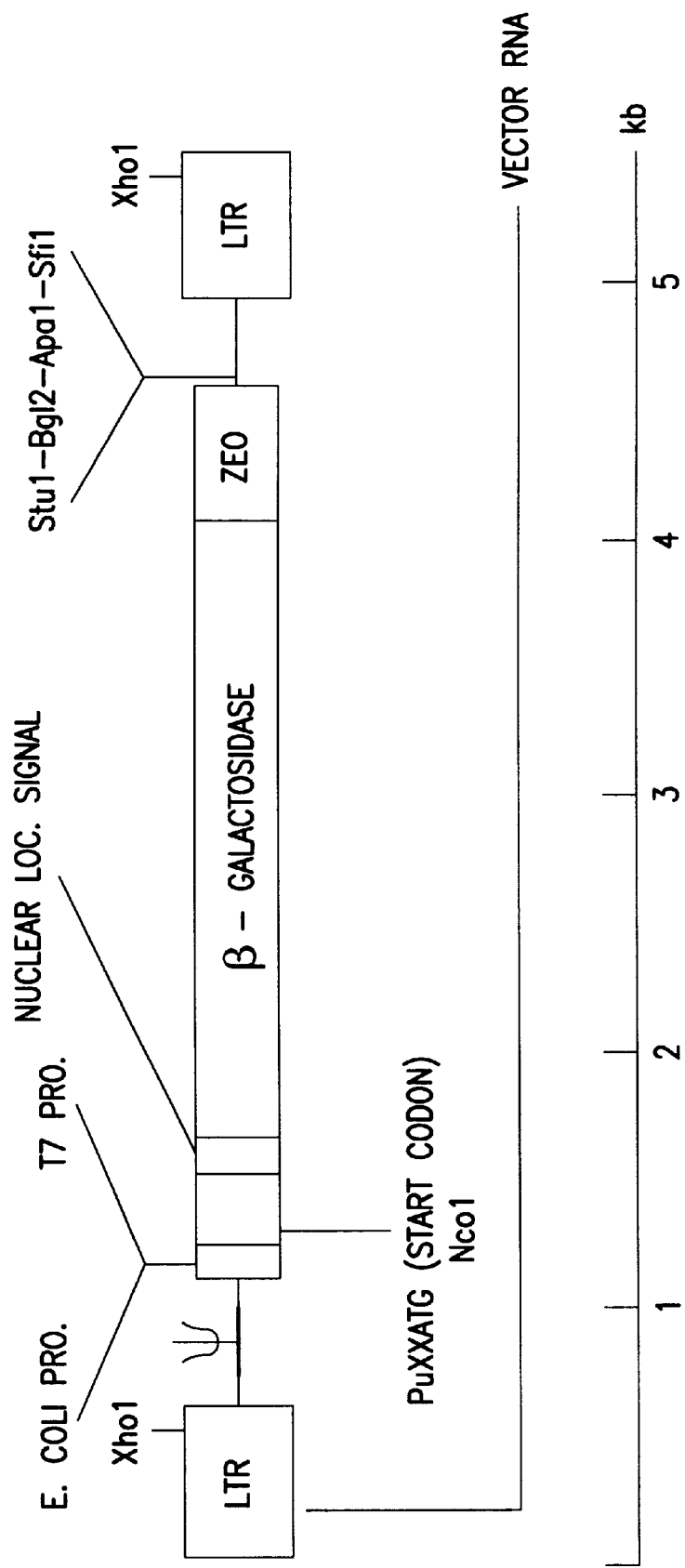

The strategy for making vectors VLP and VLPP involved the use of synthetic oligonucleotide primer pairs, and the use of the polymerase chain reaction process (PCR) to copy the region between the primers (FIGS. 1 and 2). The synthetic oligonucleotides had restriction endonuclease sites encoded into their distal termini, while their proximal termini were complementary to the regions which were to be copied from known VL30 vector sequences derived from the VL30 element, NVL3 Adams et al., supra. Only the suspected essential or desired regions of the VL30 genome were copied, including the LTRs, integration sites, packaging signal, and primer binding sites. Since the exact boundaries of the packaging signals (if any) are not known, two vectors were made which have slightly different amounts of genetic material flanking the left LTR. After the vectors VLP and VLPP were constructed, a synthetic linker (Bam HI) was added, followed by a PCR-amplified neomycin resistance gene (neo), resulting in VLPBN and VLPPBN. Slight variations in the primers resulted in the inclusion of a synthetic RNA splicing signal (vectors VLPBNS and VLPPBNS). Additional vectors with modifications in the extended packaging region (+) were made by deleting a repeat region containing several Dra3 restriction sites. VLD contains only one Dra3 repeat set, instead of four. VLC has a Cla1 synthetic linker inserted into the blunted Dra3 site, to interrupt it and to provide a convenient cloning site. VLSN (FIG. 2f) provides an internal promoter for the selectable neo marker gene. The several neo marker constructs are useful for recovering the vectors after the initial transfection stage, by selecting with G418 drug to kill nonvector-containing cells. FIG. 2g shows a vector VLPPBGZ which combines with the invention several additional advantages illustrating the versatility of the system: (1) a reporter gene (β-galactosidase, or β-gal); a different selectable marker (zeo, encoding bleomycin or phleomycin resistance) fused to the reporter; (2) a cloning site (Nco1) which enables a gene of choice to be easily inserted into the vector such that the Nco1 site represents the first favorable ATG codon within the vector (enabling translation of the encoded protein); (3) an *E. coli* bacterial promoter for use in bacteria as well as in mammalian cells; (4) a T7 bacterio-phage promoter; (5) a nuclear localization signal which enables the β-gal activity to reside mostly within the nucleus, facilitating staining of cells; and (6) an extended multiple cloning site at the right end, for cloning additional genes. This example illustrates how the basic embodiments of FIG. 2 can be expanded by the individual investigator to provide for many industrially viable modes. For example, the vector shown in FIG. 2g would be useful for determining the relative levels of expression possible from the LTR promoter in various cell types during stimulation with drugs or hormones. FIG. 2h shows more industrially viable modes: 1) VLIL2EN, which contains a cytokine (IL2) gene expressed from the VL30 LTR and a neo gene expressed from an internal ribosome entry site, so that both genes may be expressed from a single, polycistronic messenger RNA; 2) VLATG (F or R, for forward and reverse, respectively), this vector contains four false ATG start codons and a splice acceptor site (forward orientation), and just one preferred ATG codon in the reverse orientation; 3) VLOVBGH contains a selectable neo gene expressed from the LTR, while a chicken ovalbumin gene promoter is used to express a bovine growth hormone gene from an internal promoter. The promoter is herein employed to direct protein expression into eggwhite. By including promoter sequences to −900 before the start site of transcription, steroid hormone regulation can also be used in the control of transgene expression; 4) VLSVP has a BamHI site in front of the SV40 early promoter, which drives the marker, therefore the LTR promoter and a cloning site are reserved for the gene of choice. FIG. 2i shows more industrially important clones, wherein the entire VL30 packaging sequence is left intact, with a selectable marker placed near the right or 3'-end of the genome together with sites for cloning therapeutic genes. In one embodiment, VLBEN, an internal ribosome entry site is included to eliminate the need for a second promoter, while in another, neo is driven by the SV40 early transcriptional promoter, and also contains a bacterial origin of replication so that it is unnecessary to have plasmid sequences in addition to those shown. This vector, VLPSNO, also has only one copy of the LTR so it is less recombination-prone during cloning processes. This necessitates that the first round of propagation by helper cells must take place after transfection of the clone to produce a transient burst of VL30 RNA. After that, the element propagates as usual. This clone and others derived from it will be useful for mapping the genome, as it can be extracted in the presence of phage packaging oligomers, together with the genomic sequences flanking the VL30. It can be combined with in situ hybridization techniques to localize the chromosomal site of insertion.

Figure 3:
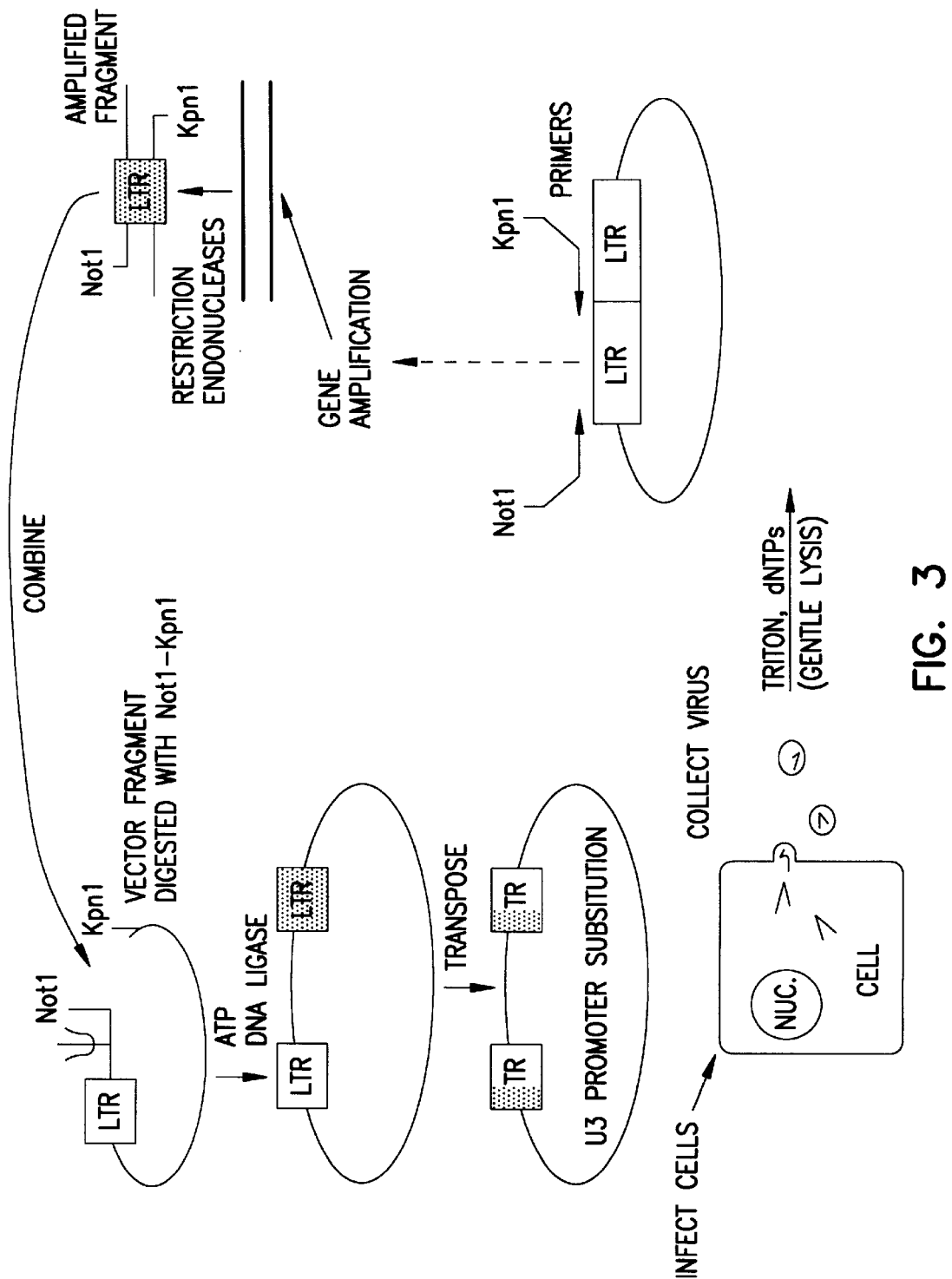
FIG. 3 is a diagrammatic illustration which shows a strategy for capturing a long terminal repeat transcriptional promoter.

FIG. 3 shows a promoter trap, by which the investigator captures and integrates a portion of the VL30 encoding the transcriptional promoter, and inserts it into the vector using (in this case) the unique Not1 and Kpn1 endonuclease sites in the various embodiments such as VLPPBN. After isolating RNA from the mouse cells expressing VL30 exhibiting the response desired, the generic VL30 primers (such as those described in the Techniques and Materials section below) are used together with reverse transcriptase and DNA polymerase activities to amplify the specific VL30 U3 promoter regions expressed in the subject cell. The primers have the Not1 and Kpn1 primer sequences, such as those illustrated, to enable directional cloning of the LTR PCR product. After the plasmid with the copied LTR is transfected into helper cells, the original VL30 primer at the left LTR will express a VL30 RNA containing the U3 region of the new sequence. After transmission, the copying process of the retrotransposon naturally selects the new U3 sequence and copies it to both LTR termini, making it the new promoter which is copied with each new round of replication. Thus, the vector promoter has changed to that of the VL30 from the cell from which it was trapped. This is expected to be useful for acquiring VL30 promoters expressed in any cell type. Another particular advantage of trapping is that the promoter of the current vector, NVL3 (or another preferred promoter) is conserved during the first round of replication, enabling efficient expression by the helper cell during transmission, and allowing for specific expressions during subsequent use.

Figure 4:
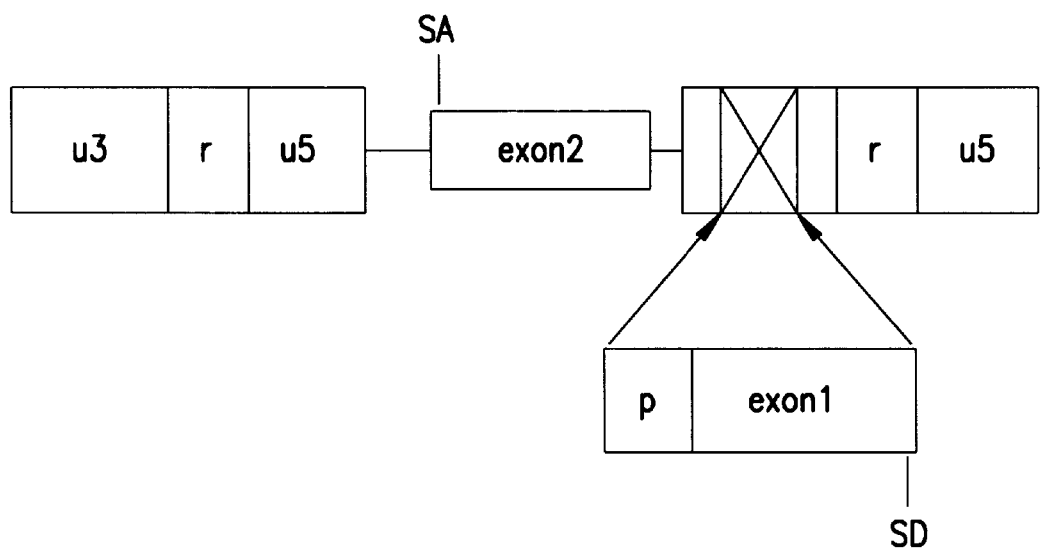
Figure 5:
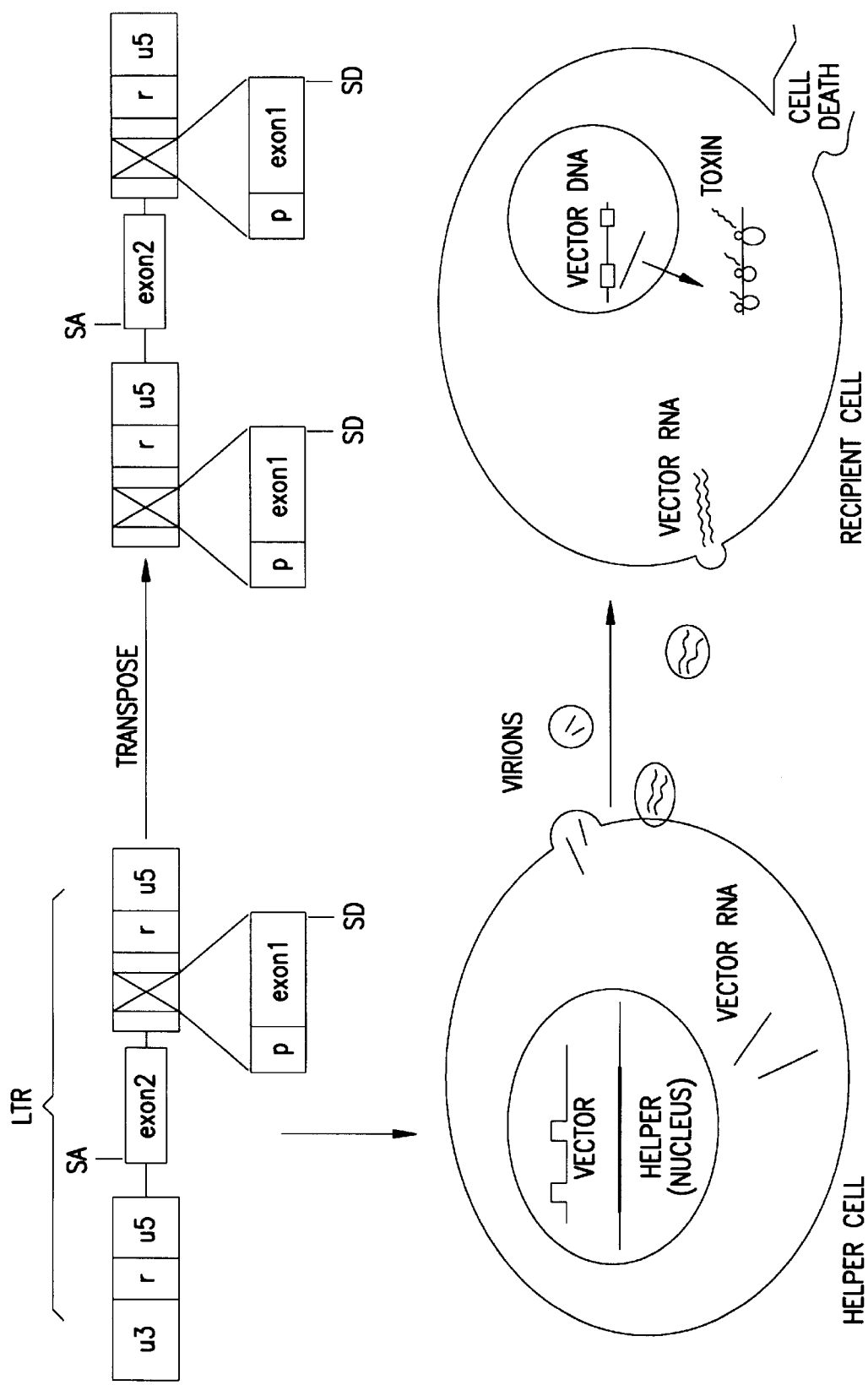
Figure 6:
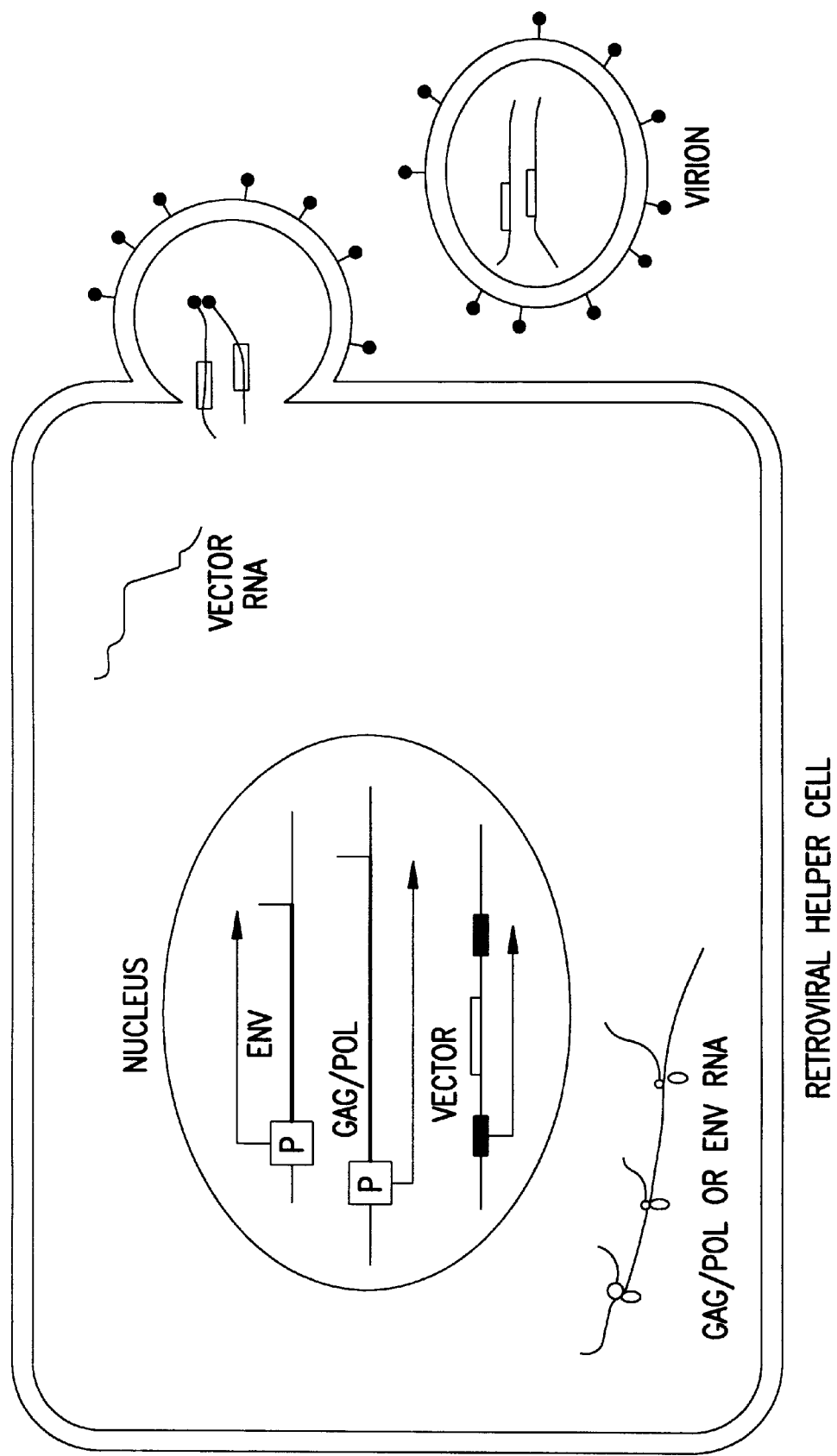
FIG. 6 is a diagrammatic illustration which shows the manner by which helper cells transmit the vectors to recipient cells.

FIG. 4 shows an additional embodiment in which a deletion is made at the right LTR U3 promoter region. The insertion of one or more unique endonuclease sites enables a promoter or gene to be inserted in either orientation. However, a sequence such as a synthetic sequence made using the above gene amplification processes, or similar strategies, may be inserted into the LTR. The inserted sequence comprises a transcriptional promoter possibly together with an exon (exon1) which may be a synthetic or natural exon encoding a portion of a gene. During the transmission of the retrotransposon, it naturally copies the U3 region from the right LTR, placing it also at the left LTR, so that in the recipient cell exon1 is placed before exon2, enabling it to function as a correctly ordered gene for the first time in the recipient cell. This strategy is intended for cells such as cancer cells. For example, in one embodiment, killer lymphocytes such as tumor infiltrating lymphocytes (TIL) may be transfected with helper sequences and with the vector sequences. The vector will not kill the TIL because the gene sequences are unrearranged. However, the TIL after migrating into the tumor, will release viral particles which contain the RNA capable of rearrangement. After integrating, the rearranged sequences express potent toxin such as ricin A, killing the cell and its neighbors in the tumor, but leaving other (nondividing) cells unaffected. This is because viral particles appear to enter and integrate into replicating cells, such as cancer cells. An additional approach toward treatment of cancer is to use a VL30 promoter which is responsive to cancerous transformation of the 22 cell, such as the NVL1 or NVL2 promoters (Carter et al, Nucleic Acids Res. 18:6243–6254, 1983) in combination with a therapeutic gene such as a cytokine gene. Interestingly, the TIL which do not take up the genes will be killed by those that do, enriching the population for effective TIL and providing 5 a new method for self-selection and enrichment. This is due to the principal of viral exclusion, which prohibits reinfection of the cell by the same type of virus which it is already expressing. Finally, the ricin toxin of the example will not seriously affect neighboring cells after death of the cancer cells, because ricin toxin is effective only inside the cell and because only the intracellular toxin subunit of ricin is included, prohibiting entry into the cell. To make it work, gene amplification processes such as those described here (for vector construction) are used to make synthetic exons for any molecule which the investigator wishes to include within the framework of the Not1-Kpn1 fragment of VLPPBN, or other suitable vector, such as those illustrated.

FIG. 5 also illustrates a method for introducing a gene which produces a toxic molecule in recipient, but not donor cells. Such method may be accomplished such that (1) a deletion is made in the right LTR and an exon from a gene is inserted into a cloning site in the deleted region, (second exon is inserted upstream); (2) upon transfection into a first cell type (donor cell), the transfected DNA integrates into cellular DNA, making RNA transcripts from the left LTR in which exon2 precedes exon1 (nonfunctional); (3) the donor cell, which is a helper cell, produces virions which transmit the LTR transcript to a recipient cell (in the recipient cell, the U3 region, containing exon1, is copied to the left LTR before integration, resulting in a rearrangement. The new transcript is spliced to produce exon1-exon2 mRNA, which is translated to produce a toxic molecule such as ricin, dyptheria toxin, etc,); and (4) the recipient cell dies, releasing the toxic molecule, which becomes nontoxic in the extracellular environment. Such intracellular toxins can spread to neighboring cells via various cell junctions, enabling the so-called bystander effect.

FIG. 6 shows the manner in which helper cells commonly transmit vectors such as retroviral vectors or the retrotransposon derivatives of the instant invention. Viral genes encoding the viral core proteins (gag), the viral polymerase, reverse transcriptase (pol), and the envelope glycoprotein (env) which surrounds the viral particle, are inserted into the helper cell. The vector is also inserted by transfection, electroporation, or other mechanism. The vector RNA which is expressed in the helper cell is specifically packaged into the virion, which buds from the cell surface and infects the recipient cell. Many helper cell types are widely available through public sources such as American Type Culture Collection, Rockville Md., which will serve to transmit the vectors disclosed here, or others made by this process. However, the preferred helper cells are those which lack, in addition to packaging sequences, both their left and right LTRs, associated promoters, and integration sequences. These types of helper cells, exemplified by the VIAGENE patented cells (WO 9205266), should have very little if any homology to the vectors described here, and have the additional advantage that they do not transmit endogenous murine retroelements and viruses. Such cell lines are in no way a part of the present invention, however their concurrent use with the invention disclosed here will impart additional advantage toward transmission in absence of replication competent retrovirus.

Figures 7A, 7B, 7C:
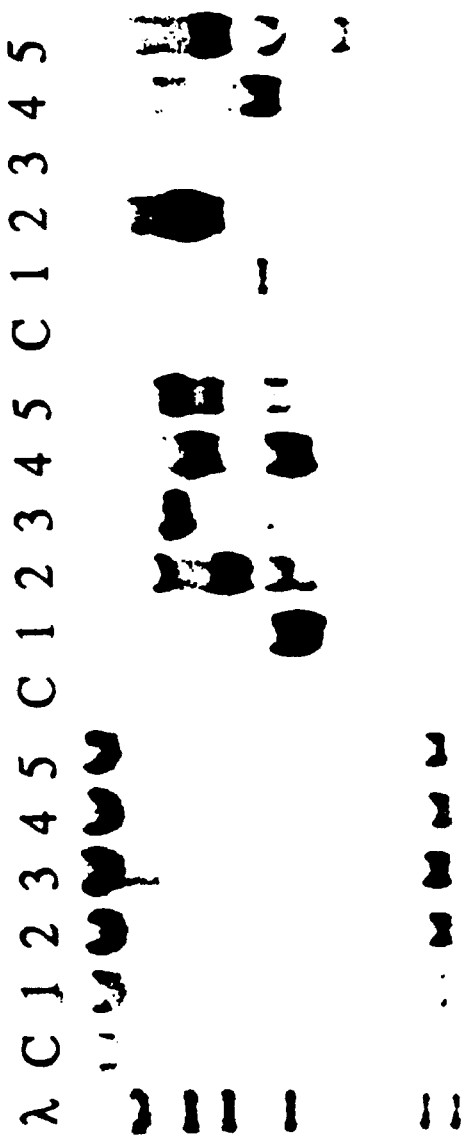
FIGS. 7 and 8 are black-and-white photographs which show physical evidence that the vectors are efficiently and stably introduced and are abundantly expressed as RNA from the VL30 transcriptional promoter in the recipient cells.
Figure 7D:
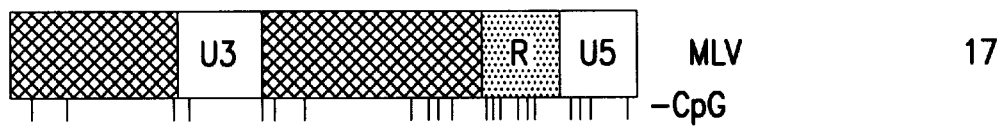
Figure 7D:
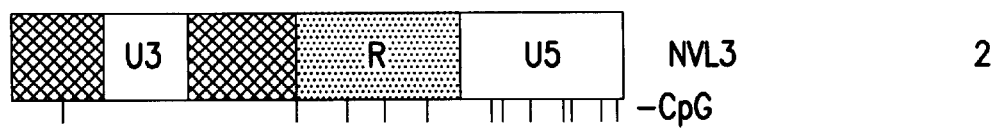
Figure 7D:
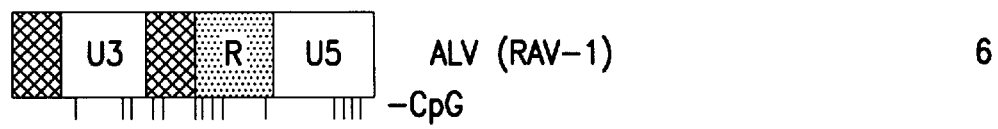
Figure 8:
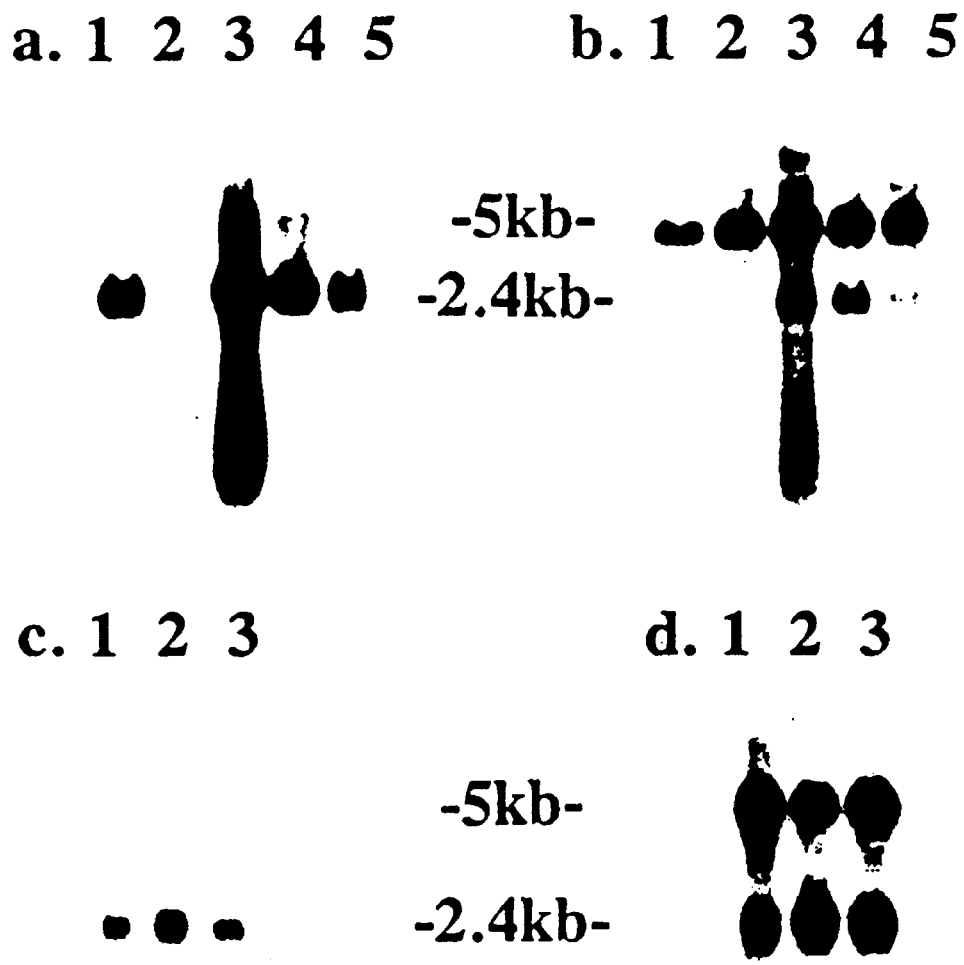

FIGS. 7 and 8 show the manner by which the vectors may be biochemically visualized after integration into recipient cell DNA by the technique of DNA or RNA blotting. FIGS. 7a through 7b show stable integration of VLPPBN DNA after transfer into recipient cells. FIG. 7a shows the unique 2 kb Xho1 fragment (reacting with the neo gene probe) which is always released from cellular DNA after integration of VLPPBN (lane C is a negative control 2 cell clone, lanes 1–5 are transduced with VLPPBN), together with the flanking heterogeneous cellular-VL30 sequences which remain associated with high molecular weight cellular DNA. This illustrates the characteristic faithfulness and stability of the vectors after passage to recipient cells. This also illustrates that the Xho1 sites in the LTR are not extensively methylated, which would render them refractile to digestion by Xho1. FIGS. 7b and 7c show similar digestions with enzymes Bgl2 and Stu1 which do not digest within the vector. This pattern illustrates integration at multiple sites within the genome of the same clones shown in 7a. A small number of integrants (usually 1–3) is seen in each case. FIG. 7d shows the limited potential for methylation of CpG sequences in the NVL3 promoter (U3), compared to MoMLV and avian leukosis virus (ALV). FIG. 8a shows expression of RNA containing neo in transfected PA317 helper cells (lane 1, pSV2neo positive control, transfected; lane 2, untransfected control; lanes 3–5, individual transfected clones containing VLPPBN). After rehybridizing the previous blot to a generic VL30 probe consisting of the Xho1 insert from the vector, mouse endogenous, expressed VL30 RNA (5 kb) is seen, along with vector RNA (2.4 kb). By comparison, FIGS. 8c and 8d show equivalent blots of ψ2 helper cells after being infected (transduced) by PA317 producer helper cells. In this case, an increase of vector RNA (relative to endogenous VL30 RNA) after transduction may be seen by comparing relative expression of both between 7b and 7d (transfected and transduced, respectively). Surprisingly, the amount of RNA from this truncated vector in each transduced clone is comparable to the total expression of VL30 RNA from all active VL30 loci endogenous to the cell, demonstrating remarkably efficient transcription of the vector RNA. FIG. 8 shows expression of an abundant RNA of the expected size (2.3 kilobase pairs) after entry of VLPPBN into recipient cells. To date, no evidence of rearrangements or deletions of the vectors have been observed (N>20), although some are expected to result from the reverse transcription process, which is error prone. Titers of vectors generally ranged $1.65 \times 10^4$ to $2 \times 10^5$ infectious units per ml of culture media for mass cultures of helper cells transduced by the vectors, using either 2 or PA317 viral helper cells.

Figure 9:
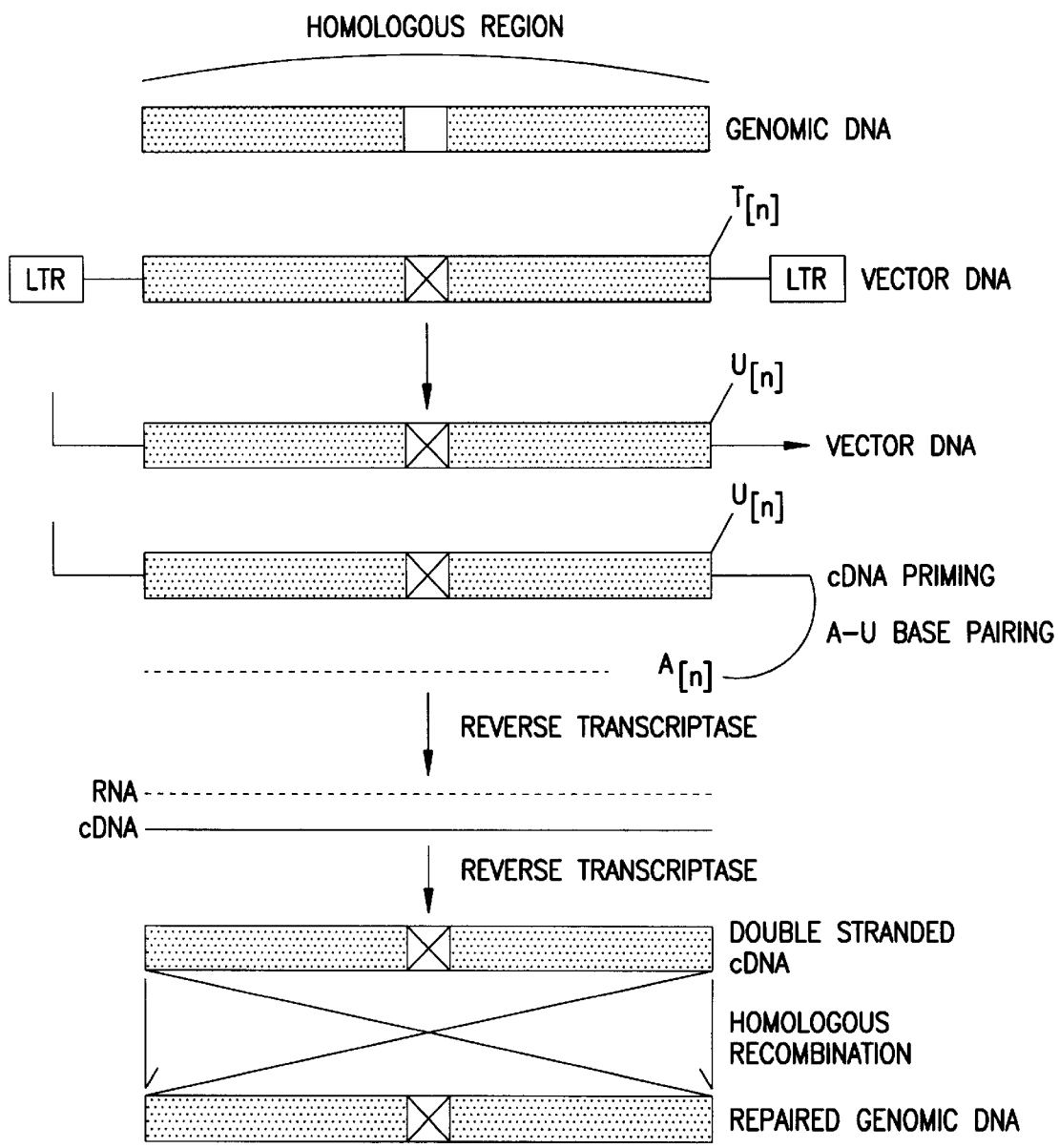
FIG. 9 is a diagrammatic illustration of retrovector homologous recombination.

FIG. 9 illustrates how a vector may be used to deliver a sequence targeted for homologous recombination with its equivalent cellular sequence. The targeting sequence together with any modification or insertion (symbolized with a boxed X) is inserted into the vector flanked by multiple T residues. After vector RNA enters the cell, the polyadenylate sequence at the 3'-terminus will hydrogen bond with the poly(U), acting as a primer for reverse transcription (equivalent to cDNA synthesis reactions), copying the targeting sequence directly instead of copying the synthetic vector sequences. A similar poly U sequence at the 5'-end of the targeting sequence will also act as a primer, resulting in degradation of the 5'-vector sequences by virion reverse transcriptase/RNAse H activity, and creating a natural terminus for the targeting sequence which will often contain only the targeting DNA sequences. The ability of the vector to efficiently deliver the targeting cDNA sequences and reverse transcribe them without vector integration sequences enables the sequences to be introduced into their homologous loci by cellular mechanisms which presently are poorly understood.

Figures 10A, 10B, 10C:
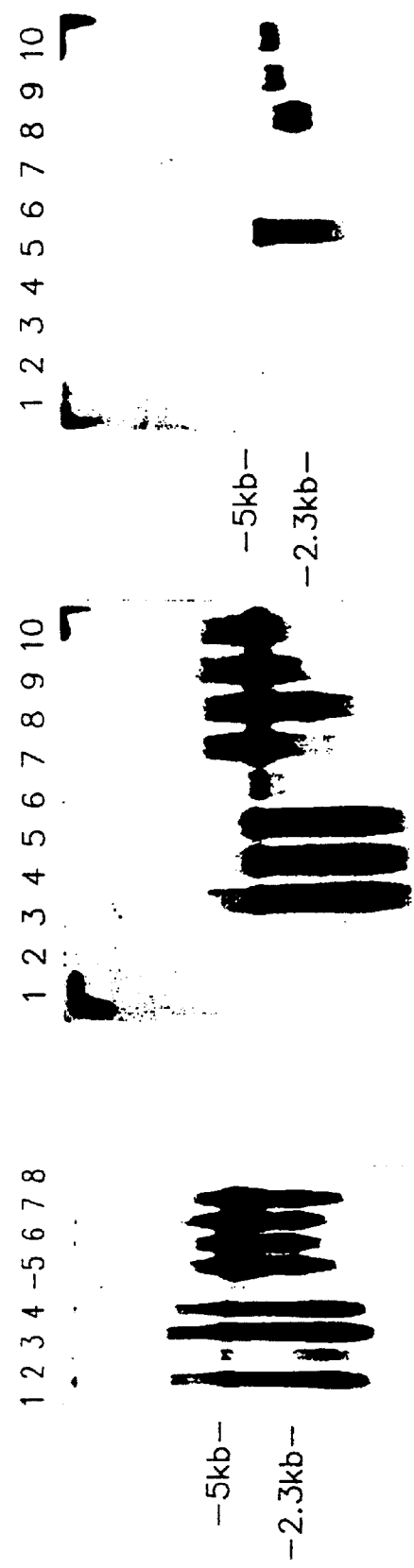
FIGS. 10A, 10B, and 10C are black-and-white photographs of VL30 transmission by helper cells.

FIG. 10 shows expression of vectors and of endogenous VL30 RNA which is transmitted by vector producer cells. FIG. 10A. shows RNA blots: total cellular RNA (lanes 5–8) from neo-selected PA317 vector producer cell lines, electrophoresed and hybridized to a VL30 probe; 5) VLPBN, 6) VLPPBN, 7) VLCN, 8) VLDN. 5 kb RNA is endogenous VL30 RNA, vector RNA is variable size, usually ~2–2.5 kb. for vectors with neo genes only. Lanes 1–4, RNA from supernatants of cells in 5–8. FIGS. 10B and C shows RNA blots made from supernatant RNA from vector producer cells (lanes 1–5) or total cellular RNA (6–10) from various PA317-derived producer cell lines, hybridized to VL30 probe (B), or neo probe (C). Lanes 1=NIH3T3 control; 2=PA317 control; 3=PA317/LPPBN; 4=PA317/LIL2EN, (VLCN containing IL2 human cDNA and internal ribosome entry site-neo); 5=PA317/RVIL2EN (retrovirus-derived positive control, not a part of the instant invention); 6=NIH3T3 total cell RNA (control); 7=PA317 total cell RNA (control); 8=total cell PA317NLPPBN RNA; 9=total cell PA317/LIL2EN RNA; 9=total cell PA317/RVIL2EN (control) RNA.

Figure 11A:
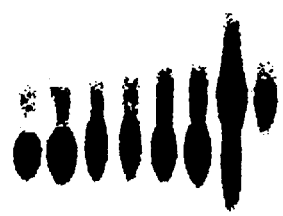
FIG. 11A is a black-and-white photograph illustrating expression of synthetic vectors.

FIG. 11 shows RNA from various vectors expressed in GPE86 cells (Markowitz et al, Virology 167:400–406, 1988) (A) together with the titers and protein expression (B, table) observed from the same cell preparations as (A). FIG. 11A: lane 1=VLPBN; lane 2=VLPBNS; lane 3=VLPPBN; lane 4=VLPPBNS; lane 5=VLCN; lane 6=VLDN; lane 7=RVIL2EN (retrovirus MLV-derived vector control); lane 8=VLIL2EN. Probe=neo. FIG. 11B shows neo protein expression and titer (colony forming units/ml, scientific notation). Protein determinations and titer were made using the same cells used in RNA blot experiments in FIG. 11A (EE=10 raised to the power).

FIG. 12 shows expression of VL30 vectors as RNA in various cell types: A) Normal human mammary epithelial (NHME) cells (VL30 probe): lane 1) uninfected NHME control, 2) NHME transduced with VLPPBN, 3) PA317 uninfected control, 4) PA317 vector producer cells transduced with VLPPBN. The 5 kb signal represents endogenous VL30 which is cotransmitted; 2.3 kb indicates vector RNA expression. B) Human peripheral blood lymphocytes (PBL) immortalized with Epstein-Barr virus (neo probe): 1) PA317NLPPBN control, 2) PBL negative control, 3) PBL transduced with VLPPBN. C) Human fibrosarcoma and colon carcinoma cells expressing transduced VL30 vectors (VL30 probe): 1) PA317NLPBN control, 2)PA317NLPPBN control, 3) PA317 control, 4) HT108ONLPBN (fibrosarcoma), 5) HT108ONLPPBN, 6) SW620 (colon carcinoma)/VLPPBN; D) same as C, probe=neo. Note smaller forms of vector in lane C6 which are not present in D6, indicating processing, or splicing of vector RNA.

Figure 13A:
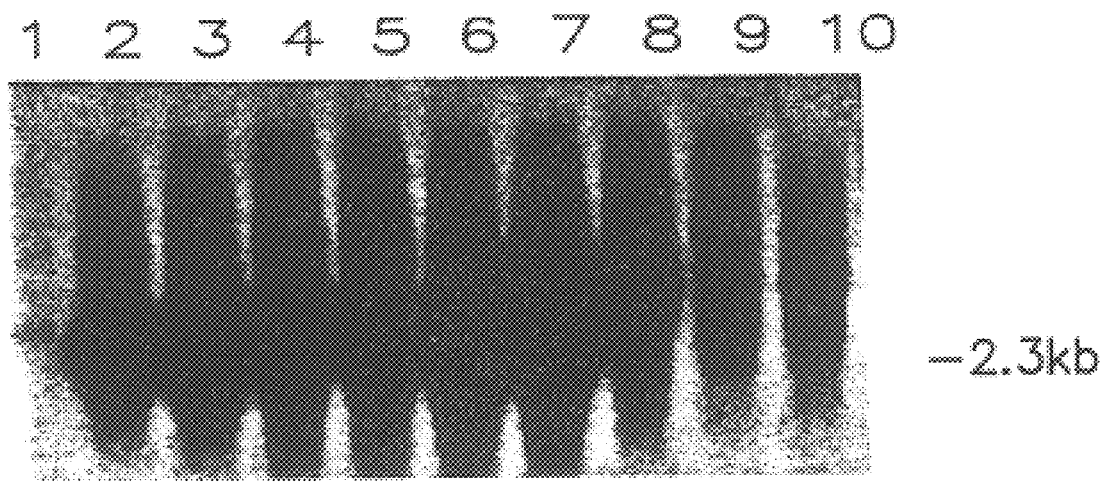
Figure 13B:
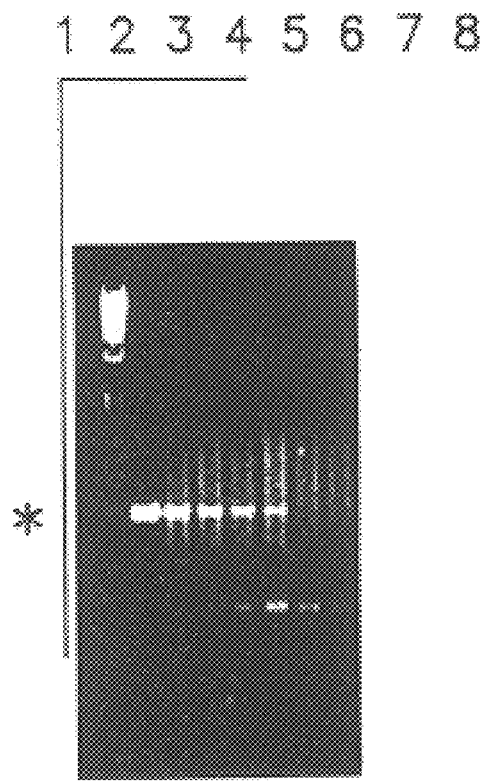

FIG. 13A shows expression of RNA in GPE86 helper cells (neo probe). Lane 1=control (no vector); 2=VLPBN; 3=VLPBNS; 4=VLPPBN; 5=VLPPBNS; 6=VLDN; 7=VLCN; 8=VLIL2EN; 9=VLATGSAF; 10=VLATGSAR. FIGS. 13B&C shows photographs of gels of gene amplification reactions assaying for the presence of OVALBGH (ovalbumin-bGH) sequences in chicken blood.

FIG. 13B shows a typical gene amplification procedure designed to identify hybrid ovalbumin-bGH gene sequences in chicken blood DNA after birth; lane1=bacteriophage lambda DNA digested with rtestriction endonuclease Hind3 (marker); 2=1 ng target (OVAL-BGH) in 1 µg of normal chicken blood DNA; 3=0.1 ng; 4=0.001 ng; 5=1.0 pg; 6=0.1 pg; 7=0.01 pg; 8=0.001 pg. The upper band (*) is diagnostic of OVAL-bGH gene insertion.

Figure 13C:
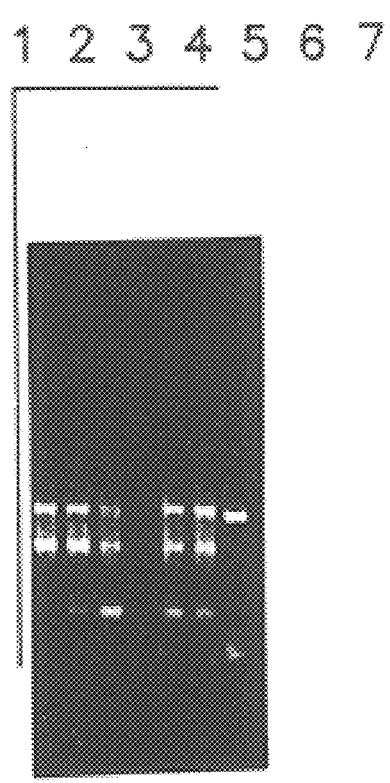

FIG. 13C shows PCR analysis of blood DNA from six chimeric chickens after birth (lanes 1–6) and a positive chicken DNA control (lane 7, 1 ng OVAL-bGH DNA in normal chicken DNA). Upper band is diagnostic.

Figure 14:
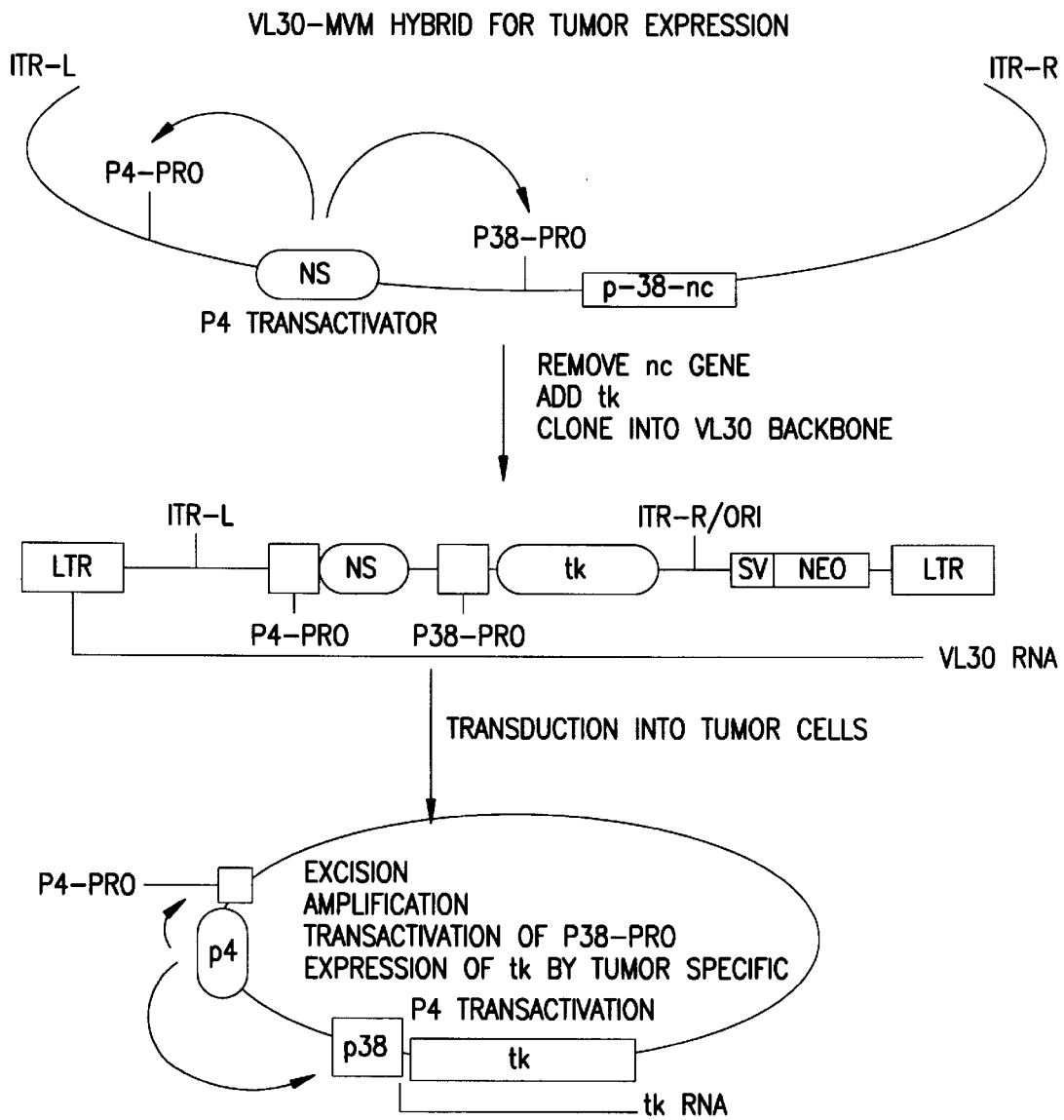
FIG. 14 illustrates a method for delivering another genome inside the vector, such as the illustrated MMV, which is useful for expressing genes in cancer cells.

FIG. 14 illustrates the method for including a MVM parvovirus genome into the vector. The parvovirus genome contains a gene encoding a transactivator protein which excises the viral DNA from the vector in the recipient cell. The transcriptional promoter of this virus is strongly activated in cancer cells. After excision, the virus replicates and expresses a protein such as herpes virus thymidine kinase enzyme, useful for cancer therapy with gancyclovir drug treatment.

3. Techniques and Materials

A. Cell Lines and Plasmids.

Cell lines NIH 3T3, C3H10T1/2, 2BAG and PA317 were obtained from The American Type Culture Collection (ATCC), Rockville, Md., and were grown in Dulbecco's modified Eagle medium (DMEM) containing 10% (vol/vol) Calf serum. The medium contains HT (20 µµM Hypoxanthine and 30 M Thymidine) in case of PA317 cells. Plasmids pSV2neo and pGEM3 were obtained from ATCC and Promega Biotech, Madison, Wis., respectively. Plasmid pNVL3 (Carter, A T, et al, Nucleic Acids Res. 11:6243–6254) was kindly provided by J. Norton. ψ2 cells were kindly provided by R. Mulligan.

B. Primers and amplification reactions.

Oligonucleotide primers were made by Genosys Biotechnologies, Inc., Houston, Tex. Gene amplification reactions were performed in 100 µl of 10 mM Tris.HCl, pH 8.3, 50 mM KCl, 1.5 mM $MgCl_2$ 200 mM of deoxyribonucleoside triphosphate, 2.5 units of taq DNA polymerase (from *Thermus aquaticus*), 10 ng plasmid pNVLOVHGH (containing the complete NVL3 genome) and 1 µg of each primer. [Note: any suitable VL30 template, such as one of the many cloned VL30 DNA sequences, or mouse genomic DNA, can be used as a template]. Reactions proceeded through 35 cycles of denaturation (94° C. for 1 min ), primer annealing (56° C. for 2 min), and primer extension (72° C. for 3 min). In most cases the annealing temperature was 5° C. below the calculated denaturing temperature. Sequences of the primers were as follows (5"-3"):

```
P1  5'-TCAGCAGATCTTGAAGAATAAAAAATTACTGGCCTCTTG-3', (SEQ ID NO:1)

P2- 5'-AAGGGCGGCCGCTTAATTAATCCCTGATCCTCCCCTGTTCCTC-3', (SEQ ID NO:2)

P5- 5'-ACTGCGGCCGCATAGACTTCTGAAATTCTAAGATTA-3', (SEQ ID NO:3)

P6  5'-GAAGATCTTGAAAGATTTTCGAATTCCCGGCCAATGC-3', (SEQ ID NO:4)

P7  5'-AAGGCGGCCGCTTAATTAATCTAAGGCCGGCCAATTGAGACC-3', (SEQ ID NO:5)

N55'-GGTTAATTAATTAGATCTAGCATGATTGAACAAGATGGATTGCAC-3', (SEQ ID NO:6)

N3  5'-TACTTAATTAACCATGGATCCGTTAACTCCGAAGCCCAACCTTTCATAG-3', (SEQ ID NO:7)

N3S 5'-TACTTAATTAACCATGGTCTAGTGGATCCGACCTTGGAGAGAGAGAGTCAGTGTTAACTCCGAAGCCCAACCTTTCATAG-3',
                                                                                (SEQ ID NO:8)
```

4. Additional Primers Made for LTR Substitutions

```
BGL2RU5 5'-TTTAGATCTTCCCTCCCCATTCCCCCTCCCAGTT-3' (SEQ ID NO:9)

3PHETLTR 5'-CGAGGTACCTGAAAGA(CT)(CT)(CT)(CT)CG-3' (SEQ ID NO:10)

MCSP3P5'-GGGTTCAGATCTTGATCAG (SEQ ID NO:11)

3LTR5MCS 5'-TAAGCGGCCGCTAGACTTCTGAAATTCTAAGATTAGAATTATTT
          ***********ACAAGAAGAAGTGGGGAATGAAGAATAAAAAATTCTGATCAAGATCTGAACCC-3' (SEQ ID NO:12)

3LTR5 5'-TAAGCGGCCGCTAGACTTCTGAAATTCTAAGATTAGAATTATTTACAAGAAGAAGTGGGGAATGAA-3' (SEQ ID NO:13)

KPN1IRU5 5'-CGAGGTACCTGAAAGATTTTCGAATTCCCGGCCAAT-3' (SEQ (SEQ ID NO:14)
```

5. Subcloning of Gene-amplified Fragments

Gene-amplified fragments were run in a 1% agarose gel and each DNA fragment was excised from the gel and purified using Geneclean II kit (BIO 101 Inc., La Jolla, Calif.). For example, the DNA fragments P1/P7 and P5/P6 (FIG. 1) were digested with restriction ennuclease Not1, run on 1% agarose gels and further purified by the Geneclean II method. Ligation reactions (P1/P7 & P5/P6, or P1/P2 & P5/P6) were performed (to join the two Not1-digested fragments) in 10 µl Vol. containing 66 mM Tris.HCl, pH 7.6, 10 mM MgCl2, 1 mM DTT, 1 mM ATP and 1–2 units of T4 DNA ligase (Boehringer Mannheim Biochemicals) at 4° C. for 16 hrs. The ligated products were run 1% agarose gel, desired bands were excised from the gel and purified by the Geneclean II method. Then the fragments were digested with Bg/II, further purified as above, ligated into plasmid pGEM3 vector (Promega, Inc., Madison, Wis.) at the BamH1 site, transformed into *E. coi* SURE competent Cells (Stratagene, La Jolla, Calif.) and selected in Luria Broth-agar-Ampicillin plates. Two clones (pVLP and pVLPP) were selected by restriction enzyme analysis (XhoI, NotI, XbaI, KpnI & HindIII) (FIG. 1b). A BamHI linker (pCGGATCCG) was introduced into the PacI site of both clones after blunting the Pac1 overhanging ends with T4 DNA polymerase, yielding pVLPB and pVLPPB. Then the (BamHI/BgII digested) neo amplified fragments N5/N3 (no splice acceptor site) or N5/N3S (splice acceptor site) were ligated into the BamHI digested, calf intestinal alkaline phosphatase (CIP)-treated pVLPB, yielding pVLLPBN and pVLPBNS, or into Bam HI and CIP-treated pVLPPB, yielding pVLPPBN and pVLPPBNS. The orientation of the neo-vector was determined by BamHI restriction enzyme analysis. VLDN was created by digestion to completion of VLPPBN by Dra3, followed by dilution and religation. Additional treatment of the Dra3 limit digestion above by T4 DNA polymerase in the presence of nucleotide triphosphates, followed by addition of an 8 bp linker encoding Cla1 (Boehringer Mannheim), followed by digestion with Cla1, followed by gel isolation of the vector fragment, and religation, yielded VLCN.

6. Nucleic Acid Procedures

Total RNA was isolated from 80% confluent cells as described (Chomczynski, P, and Sacchi, N, 1987, Anal. Biochem. 162:156–159). Neo (0.76 kb Pvu2 fragment of pSV2NEO) or VL30 (0.9 kb Xho1 fragment of pVLPB) hybridization probes were made by Nick Translation (N5000, Amersham, Arlington Heights, Ill.). Nucleic acid hybridizations, transfection of calcium phosphate/DNA coprecipitates, infection in the presence of 6 g/ml of polybrene and titer determination were performed as described (Ausubel, F M, et al, 1989, in Current Protocols in Molecular Biology (Greene Publishing Assoc. and Wiley Interscience, New York, N.Y.).

7. Design of VL30 vectors

The NVL3 transcriptional unit was selected as a template for vector construction because its LTR transcriptional promoter constitutively expresses abundant RNA in mouse and human cells. The template plasmid was pVLOVHGH which is a derivative of pNVL3 (kindly provided by Dr. J. Norton) containing the entire NVL3 genome (Carter et al, 1983, Nucleic Acids Res. 18:6243–6254) in nonpermuted form [note: since NVL3 is also found in the mouse genome as a proretrotransposon, a template is readily available from such sources as NIH3T3 cells]. Putative nonessential DNA was reduced to a minimum through the use of selective gene amplification, leaving as much space as possible for foreign genes to be inserted into the multiple cloning site (MCS) which was encoded into the oligonucleotide primers (retroviral packaging is limited to 10–11 kb total vector size). Homology between VL30 and intact MoMLV was restricted mostly to 11 bp of direct homology at the left LTR/(−)-primer binding site junction; 17/19 bp homology at the (+)-primer binding site/right LTR boundary; and 24/30 bp homology in the encapsidation hairpin region. No other concerted homology was observed. Thus, helper cell types, such as the Viagene cells listed above (which lack encapsidation regions and 3'-LTR sequences) have almost no purposeful homology with the vector sequences.

Because the exact boundaries of packaging sequences in VL30 are not known, we utilized a region elongated to 611 bp beyond the LTR (FIG. 1a). The region was determined a priori by analogy to a packaging enhancer region (Armentano, D, et al, 1987, J. Virol. 61:1647–1650; Bender et al, 1987, J. Virol. 61:1639–1646) of MoMLV which extends well beyond a hypothetical hairpin structure and into the retroviral gag gene, which enhances packaging by at least 10 fold. The strategy for amplification of essential cis-acting regions comprising vectors is shown in FIG. 1a. The basic vector (pVLPP) was designed so that any gene placed into the multiple cloning site could contain the first AUG codon in a favorable context (such as PuXXAUG or PuXXAUG) for translation such a codon would be deliberately placed there by the investigator. This enables any gene to be efficiently translated from the LTR promoter, and is fundamentally different from MoMLV transcriptional units where translation is often confounded by favorable AUG codons upstream from the cloning sites. Oligonucleotide primers included multiple cloning sites and in one case a synthetic consensus splice acceptor site. (Darnell, J. E., Baltimore, D. & Lodish, H. F. (1986) in *Molecular Cell Biology* (Scientific American Books, New York, N.Y.) pp305–369). The template included a potential splice donor site upstream near to the LTR (SD, FIG. 2a). For directional cloning and to remove the TATA-like residues of the Pac1 cloning site, a BamHI linker was inserted at the Pac1 sites, generating pVLPPB. Two secondary vectors were constructed which contained the amplified neo gene: (PVLPPBN and pVLPPBNS). The vector which contained the synthetic splice acceptor site encoded into the oligonucleotide was denoted by S at the end of the designation. This putative splice vector was intended to permit two types of RNA to be expressed from the spliced and unspliced forms of the LTR transcript. The neo gene was expressed from the first favorable (Kozak, M, 1978, Cell 15:1109–1123) translational start codon (PuXXAUG) contained within the pVLPPBN vector RNA. The similar vectors made from VLPBNS (those with shorter packaging sequences and one P in the designation) were made in a like fashion, starting with VLPBNS.

8. Expression of Synthetic VL30 Vectors

The neo vectors shown in FIG. 1b were transfected into PA317 retroviral helper cells (Miller and Buttimore, 1986, Mol. Cell. Biol. 6:2895–2902) using the calcium phosphate method (Graham and van der E B, 1973, Virology, 52:456–467). pSV2NEO plasmid DNA was also transfected into the helper cells as a positive control. Interestingly, three transfections done with synthetic vector VLPPBN preparations produced as many or more colonies than the pSV2NEO control plasmid upon selection with the drug G418 (not shown). This result indicated that transcription and translation of the neo gene was effective and that gene amplification methods were effective in the majority of cases, since each experiment represented a separate vector construction. RNA blot analysis is described in the figures legend.

9. Integrated VL30 Vector DNA Sequences VLPPBN-transduced ψ2 helper cell lines were cloned and examined by DNA blotting in order to determine copy number and integrity (FIG. 7a). The vector LTRs contain only two CpG residues in the U3 promoter region, compared to 17 CpGs in MoMLV and 7 in avian leukosis virus (see comparison, FIG. 3d). Unlike MoMLV which is transcriptionally inactivated during embryogenesis, the avian virus is often expressed at significant levels in the tissues of adult and developing animals (Cook et al, 1993, Poultry Sci. in press). It has been suggested that cytosine methylation is primarily a mechanism for neutralizing invading DNA (Bestor, T H, 1990, Phil. Trans. R. Soc. (London) B 326:179–187). Lack of methylation potential of VL30 sequences such as these may therefore help to explain why significant amounts of VL30 RNA is expressed in mouse cells in vivo (Norton, J D, and Hogan, B L, 1988, Dev. Biol 125:226–228) while retroviral sequences are often transcriptionally silenced 10. Transmissibility of Synthetic VL30 Sectors Filtered (0.45m) media from the PA317 helper cells bearing the vectors was transferred to ψ2 ecotropic helper cells. After selection, media was again transferred to PA317 cells and selected with G418. Finally, the transduced forms of T2 and PA317 helper cells were co-cultured for two weeks in a permissive ping-pong (Bestwick et al, 1988, Proc. Nat. Acad. Sci. (USA) 85:5404–5408) experiment, wherein vectors were transmitted back and forth between the two compatible cell lines in order to amplify vector copy number. Titers of mass cultures averaged $10^5$ for ecotropic and mixed helper cell types, and from $2-4 \times 10^4$ to $1.2 \times 10^5$ for the amphotropic helper cells.

In order to ascertain the RCR potential of the present vectors, they were transduced into ψ2 helper cells (which occasionally produce replication-competent virus), and into the PA317 helper cell line. PA317 is used to generate stocks free of replication-competent virus for human gene therapy, but it can still generate wild-type virus under permissive circumstances (Muenchau, D D, et al, 1990, Virol. 176:262–265. Stocks of three VLPPBN vector preparations, or of a retroviral control BAG-virus vector (ATCC, #CRL 9560) were transmitted via 10 ml ($10^{5-6}$ IFU) of filtered media to recipient NIH3T3 cells, and drug-resistant colonies were selected by G418 treatment. Mass cultures of resistant colonies were grown to near confluence, and culture media from each was filtered and transmitted to a second plate of NIH3T3 cells. None of the three VLPPBN vector preparations produced drug-resistant (RCR) colonies upon secondary passage (<1 IFU/10 mls), in either ψ2 or PA317 cells. However, the control BAG retroviral vector resulted in ~200 CFU/ml upon secondary passage of a stock which had tested negative for RCR two passages earlier (data not shown). The replication-competent retrovirus detected in the BAG recipient cells, but not VL30 vector infected cells, could have represented passive carryover of the ψ2 genome (Mann R, et al, 1983, Cell 33:153–159), or else recombination or endogenous retroviral transmission occurred, resulting in the production of replication competent retrovirus.

These results illustrate the usefulness and relative safety of VL30-derived synthetic vectors.

11. Right (3') LTR Cloning Cassette

To insert a cloning site and promoter deletion in the 3'LTR region, a synthetic double-stranded oligonucleotide is made by DNA polymerase (Klenow fragment, Boehringer Mannheim) using a synthetic oligonucleotide spanning from the Not1 site of the vectors up to the deletion and MCS site inside the LTR. The oligo 3LTR5MCS is annealed with the oligo MCSP3P in the presence of 200 mM deoxynucleoside triphosphates and extended by Klenow DNA polymerase. The full length product is isolated from an agarose gel using the technique described above, and is digested with Bgl2 enzyme, after which it is again gel purified as above. NVL3 template such as pNVL3 or pNVLOVHGH is used for gene amplification as described above using the primers BGL2RU5 and KPN11RU5. The resultant fragment is isolated from an agarose gel as described, is digested with Bgl2, is reisolated from the gel, is ligated to the Klenow product described above, and is again reisolated from the gel. This product is digested with Not1 and Kpn1 enzyme, is again reisolated from a gel, and is ligated into the large Not1-Kpn1 digested fragment of the vector, such as VLPPBN. The resulting 3'-LTR contains a large deletion in the U3 region, which can be used as a cloning site for objects such as a foreward or reverse promoter, in addition to the basic promoter which is still left in the LTR, defining the "CAAT" and "TATA" transcriptional sites. This enables the investigator to clone a VL30 or other transcriptional promoter into the Bcl1 or Bgl2 restriction endonuclease sites provided.

12. To Trap a Promoter from a Specific Cell Type

Different mouse tissues, developmental stages, or stages of stimulation by various factors will occasionally give rise to specific subsets of VL30 RNAs defined by their transcriptional promoters. These promoters can be very useful to the investigator or gene therapist to elicit a similar transcriptional response. It is possible [using the 3'-LTR cloning cassette described in (11.) above, or an equivalent cassette] to clone a desired highly speific promoter by a number of similar methods.

First, RNA is isolated from the target cells, and the sequence of the specific VL30 promoter is determined (for example, by reverse transcriptase-PCR, using conserved LTR sequences such as (+)PBS-inverted repeat, and U3-R, etc.). A set of primers is then devised to permit amplification of the U3 region of the VL30. The primers used should terminate in Bcl1 and/or Bgl2 restriction endonuclease recognition sequences to permit cloning into the 3'-LTR cloning cassette. This or a similar method will provide the investigator with a promoter having a desired transcriptional specificity, such as a muscle cell, an estrogen stimulated cell, or a developing brain cell. A major advantage of this method is that the promoter is ready made and useful in the VL30 format (ie, it is not necessary to clone a specific cellular gene, characterize its promoter, and then adapt it for possible use in a VL30 vector). The diversity of VL30 promoters in nature provides an elaborate array of possibilities which are very useful for specific gene therapy applications. Furthermore, the ability of VL30 promoters to function effectively in human cells makes them highly adaptable to human medicine.

13. To Trap an Entire LTR from a Specific Cell Type

In addition to the method of promoter traping, it is possible to trap an entire or intact LTR from a cell which expresses it. To do so, the cell is first infected with helper (MoMLV or equivalent) virus (conversely, an endogenous virus is activated within the animal or cell, for example by 5-azacytidine stimulation). The viral particles are harvested and the RNA is reverse transcribed using the endogenous reverse transcription reaction of partially disrupted virions as described by Carter et al, 1983. The intact LTRs generated by reverse transcription are then amplified (either directly by PCR, or after gel isolation of high molecular weight cDNA as described in Carter et al, supra). As a preferred example, the primers 3LTR5 and 3HETLTR are used to copy the LTR with preprogrammed synthetic Not1 and Kpn1 unique restriction endonuclease sites on the ends to permit rapid directional cloning into the preferred vectors.

An alternative method is to directly isolate the RNA from the cell (Chomczynski et al, supra), reverse transcribe it in the presence of dNTPS and Moloney murine leukemia virus reverse transcriptase (Ausubel et al, supra), and isolate large cDNA from a gel prior to amplification, or else directly amplify the LTR region from the complex mixture using primers such as those suggested above. In many cases, it is helpful to consult a standard source such as the latest version of Ausubel, supra, for advise and reaction conditions for performing reverse transcription and PCR reactions. In addition, the manufacturers (Cetus Perkin-Elmer and Invitrogen) provide detailed kits and instructions for such reactions as PCR and reverse transcription PCR.

To clone the LTR, digest the vector such as VLPPBN or VLPP with Not1 and with Kpn 1, and isolate the large fragment from a gel. Cloning will be made easier if the plasmid fragment is also treated with alkaline phosphatase (see Ausubel, supra, for details) to reduce nonspecific cloning. After combining the LTR fragment and the vector, ATP and ligase are added in a standard ligase reaction (Ausubel, supra). After transforming *E. coli* SURE competent cells (or equivalent, Stratagene, Inc.), ampicillin resistant colonies bearing the expected fragments can be determined by restriction endonuclease digestion. These fragments can then be used as vectors for genes with specific promoter activity. The first helper cell into which the construct is transfected will transmit the vector with the same transcriptional specificity as NVL3, since it still has the original promoter in place at the 5'-end. However, recipient cells will have this promoter replaced with the sequences at the 3'-end. In the event that the R region of the new promoter differs significantly from that of the 5'-LTR, difficulty may be encountered in reverse transcription, or a hybrid R region may result. This should not affect the U3 promoter region, provided enough similarity exists to permit reverse transcription.

14. To Trap Promoters from Hetergeneous VL30 Sequences using Mouse Cellular DNA as a Source of all Possible VL30 Promoters Gene amplification reactions are performed using the primers 3LTR5 and 3PHETLTR. After denaturing the genomic DNA at 95° C. for one minute, the primers are annealed at 36° C. for one minute, then gene amplification is performed with extension, denaturation, and annealing temperatures of 72° C., 94° C. and 360° C. for two additional rounds, after which the annealing temperature is changed to 55° C. for the remaining 35 cycles. Magnesium and nucleotide concentration as well as annealing temperature for specific templates should be varied to determine the optimum. After amplification the fragments are isolated from a gel as described above, digested with Not1 and Kpn1, and ligated into the large Not1-Kpn1 fragment of the vector, such as VLPPBN.

15. A Method of Performing Homologous Recombination using a Vector

Retrovectors are useful for precisely integrating genes into the genome in a nonsequence-specific manner. However, repair of a genetic defect often requires the precise change of one or more base pairs of genetic information, which is not usually possible with retroviruses. Instead, homologous recombination methods are used, wherein homology between the inserted gene and the endogenous locus is the basis for natural cellular processes guiding insertion of the theraputic gene into the appropriate place. Unfortunately, homologous recombination is an inefficient process compared to retrovector transduction, requiring physical transfection methodology followed by careful screening of individual cell clones. Thus, it would be very desirable to substitute a method which inserts a single copy with precision and efficiency into a homologous locus.

To make a homologous recombination vector, the genetic sequences which are to be precisely recombined into the genome are first constructed using standard recombinant DNA technology (Ausubel et al, supra). The sequence or sequence change of choice is inserted in or between isolated sequences from the homologous region of the genome, in exactly the sequence configuration desired, as shown in FIG. 9. Next, the target sequence and flanking homologies to the genome are inserted into the retrovector, such as VLPPBN, or any similar retrotransposon or retrovirus-derived vector.

In one preferred method, the sequences are constructed so that the 3'-end of the homologous region contains a T-tract, consisting of several T residues (preferably, 8 or more Ts should be used). In many instances, it may be desirable to include a tract containing Ts (or alternatively, a polypurine tract) at the 5'-end of the homologous region. One or both of these sequences in concert with reverse transcriptase, will act as primers for reverse transcription of the region containing the homologous sequences and target DNA sequence. This process is very similar to the in vitro synthesis of cDNA using oligo d(T) as a primer. This is because the vector RNA is polyadenylated, and will fold back to prime synthesis of first strand complementary DNA from the T-tract [by base pairing with the T residues (or U residues in RNA)]. Polypurine is also a natural primer of second strand synthesis of retrovector RNA, and hence it is also a preferred primer. If second strand synthesis does not begin at the desired locus, it will occur naturally by folding back of first strand cDNA. This is the same principal which is used to generate second strands during in vitro cDNA synthesis. Another preferred method is not to use any priming regions such as T tracts, but to simply permit the vector to undergo homologous recombination, resulting in elimination of some or all vector sequences. Since the exact site of initiation of cDNA synthesis is not critical for homologous recombination, any of these mechanisms might be preferentially used. Thus, double-stranded cDNA will result which does not include some or all of the vector sequences, permitting homologous recombination to occur by well-established natural mechanisms (recombination between the flanking homologous sequences). The vector thus permits entry and reverse-transcription of the sequences by a novel mechanism which results in elimination of some or preferably all of the vector sequences. It has been previously shown that inclusion of a selectable gene such as neo permits targeting of neo to a specific locus due to the homology of the flanking sequences (also called knockout, since it eliminates gene activity through precise insertional mutagenesis). This is a useful means of producing transgenics as well as cell and animal models of disease. Primary advantages of using a retrovector to deliver the genes as described are, 1) efficiency, and 2) delivery of a single copy of the gene to the desired locus.

16. To Increase Titer of a Vector, and to Increase Resistance to Retroviral Disease Through Competitive Inhibition, and to Easily Mark Cells with a Vector Previously, it was shown that VL30 retroelements were copackaged into virions, including virions of packaging cell lines (Hatzoglou et al, Human Gene Therapy, 1:385-, 1990). However, it was not known how much VL30 RNA was copackaged, or how much effect it might have upon the ability of helper cells to propagate a vector. Nor was it shown that improved helper cells used in human gene therapy (Miller, PCT WO8808454) also transmitted endogenous VL30. It is now disclosed for the first time that a cell line used in human gene therapy (PA317), also transmits significant amounts of contaminant endogenous VL30 during vector transfer (FIG. 10). The RNA blot of virion RNAs extracted from the supernatant (viral) fraction revealled much endogenous (5 kb) VL30 RNA being packaged and transmitted, but little if any vector RNA was detected (2.3–2.5 kb), unless blots were reprobed with a neo gene probe. Thus, endogenous VL30 sequences iterated at 100–200 copies per cell are able to produce much competing VL30 RNA which will affect titer attainable from competing retrotransposon vectors such as VL30 vectors or from retroviral vectors. Fortunately, no adverse effects have ever been observed in animals or in man resulting from mouse VL30 retrotransposons. One aspect of this phenomenon is that VL30 retrotransposons are de facto approved for human gene therapy, since their presence is inevitable in all gene therapy experiments using these approved cells. Another aspect is that endogenous VL30 elements are transmitted with significantly higher titer than present vectors such as retrovirus-derived vectors; and that the "stuffer" regions of endogenous VL30 are thus recognized and designated herein as packaging sequences useful for high titer. For example, in human gene therapy it would be desirable to transmit a vector efficiently so that no drug selection was necessary, or so that gene therapy could be administered directly in an efficient manner to mark cells without introducing unnecessary expressed genes. FIG. 10B illustrates that after one exposure to one dose of helper cells expressing endogenous VL30 vector, the human recipient cells are expressing large amounts of the transmitted sequences in the form of RNA, and that the result was obtained without drug selection as desired. However, when the blot was rehybridized with a neo gene to detect co-transmitted vectors, only one (high-titer retrovirus-derived vector control) lane gave a significant signal after exposure. Thus, the endogenous VL30 sequences are themselves able to be used as very efficient vectors, which do not require drug selection or other types of enrichment in order to be expressed effectively in recipient cells. This result also illustrates that endogenous VL30 sequences contain variable-length (approximately 4 kb) regions which are capable of increasing the efficiency of transmission. This genetic material, (including the stuffer regions of NVL1,2, & 3 (which individual elements are a major part of the VL30 milieux expressed in NIH3T3 cells or vector producer cells), excluded from the vectors shown in FIG. 2, is thus designated as the VL30 enhanced packaging region. The skilled artisan can thus use this stuffer region (defined as the entire region between the VL30 LTRs), or portions derived from it, to enhance the packaging efficiency attainable from conventional vectors, or the synthetic vectors shown. Yet another aspect of the results shown in FIG. 10 is that considerable contamination occurs when murine helper cells are used. One possible way to avoid contamination is to use a nonmurine cell line, such as a human cell line, to avoid competitive exclusion caused by endogenous VL30 (and possibly other murine retroelelents). For example, Jolly (PCT WO9205266) disclosed a a dog D17-derived and a human HT1080-derived cell line for the transmission of vectors. The evidence shown here is the first direct evidence known to us of competitive packaging observed in viral particles caused by VL30 endogenous sequences. It is also apparently the first demonstration of the superiority of the VL30 enhanced packaging sequence defined herein. It is also apparently the first clearcut demonstration of contamination of packaging cells used in human gene therapy, such as PA317. This data also demonstrates a new use of endogenous VL30 (or other retrovectors similar to or derived from them), which is to act as a competitive inhibitor of retroviral infections such as those of leukemia viruses or HIV virus. While this may be a natural biological role of VL30 in feral mice, the experiment teaches a new method for inhibition of viral infection in man, which is through the introduction into human cells of a competitive inhibitor of viral packaging. This is distinct from the old method of inhibition of retroviral infection caused by viral exclusion phenomena related to envelope subtype, which are well known.

17. To Transduce a Therapeutic Gene into Cells without the use of Helper Virus

As shown in the section above, biological entities such as helper cells are a serious potential source of contamination. Such contaminants include viruses, bacteria, and mycoplasmas, as well as retrotransposons and other retroelements. Hence, it would be very desirable to eliminate their use altogether by combining synthetic vectors such as those described here with other purified biochemical components such as reverse transcriptase and liposomes, and/or coat proteins or other agents for the purpose of gaining entry into cells.

In one preferred mode, cellular RNA containing a vector such as VLPPBN or other retrovector (along with cellular tRNA primer) is purified and combined with purified reverse transcriptase enzyme and with cationic liposomes [or a commercial liposome preparation such as Lipofectin™ (BRL Inc., Bethesda, Md.) according to the manufacturers instructions] or specific liposomes such as those prepared from phosphatidyl serine or phosphatidyl inositol. The preparation will not enable reverse-transcription of the RNA in the absence of RNA precursors. The four deoxynucleotide triphosphates may be included in the liposomes, or they may be provided by the cell after entry into the cell. The liposome preparation is added to the cell culture media surrounding the recipient cells, and is allowed to enter the cells or tissue. Once in the cell, the reverse transcriptase/vector RNA/primer complex is reverse-transcribed in the presence of cellular deoxyribonucleotide triphosphates. The complex will be naturally integrated into cellular DNA due to the presence of integrase activity in Moloney murine leukemia virus reverse transcriptase (or other unmodified reverse transcriptase enzyme).

In another preferred embodiment, the vector RNA can also be generated from other sources, such as T7 or SP6 bacteriophage polymerases. Indeed, the vectors VLPPBN etc. (FIG. 2) come with bidirectional RNA polymerase promoters (SP6 and T7) flanking the vector sequences to enable probes and virus-like RNA to be generated in vitro. The RNA is generated from the bacteriophage promoter by following the manufacturers instructions included with the polymerase kit (Riboprobe, product #P1071, Promega, Inc., Madison, Wis., or similar kits). It may also be desirable to modify the vector so that the RNA start site is at or near to the U3-R boundary of the vector, so that it is an effective mimic of full-lingth VL30 RNA. In some cases, it may be desirable to enzymatically cap vector RNAs prior to use, by means of capping reagents such as commercially available capping kits (Stratagene, #200350, La Jolla, Calif.), according to the manufacturers instructions. For example, it has been shown that capping increases the efficiency of translation and may be important for processing/stability (Nielson, D A, and Shapiro, D J, 1986, Nucleic Acids Res. 14:5963; Banerjee, A K, 1980, Microbiological Reviews 44:175–205; Filipowicz, 1978, FEBS Lett. 96:1–11;). In addition, the (−)-strand primer can also be a synthetic nucleic acid molecule compatible with the viral delivery system, or it can be purified from cellular RNA as a tRNA fraction (VL vectors have a tRNA$^{gly}$ primer binding site). When used together, the synthetic vectors together with synthetic "helper" chemicals described here constitute a completely synthetic system which should be free of complicating biological entities such as endogenous retroviruses (however, if cellular RNA is used as the source of vector RNA, investigators should be aware that retroelements may be present). These innovations together permit gene therapy to be performed with greater safety and fewer validation problems. This is of particular importance as it will permit gene therapy to be used as practical medicine rather than as complicated procedure with few practical applications. In addition, liposome preparations or similar chemical vehicles can be stabilized in the absence of cellular enzymatic activities such as ribonucleases which are present when helper cells are used to transmit the vectors. The synthetic system is not limited by the availability of starting material, since large quantities of RNA can be generated in a highly purified form by enzymatic mechanisms such as those described. In addition, synthetic RNA carries little risk of contamination by retroelements other than the vector. Thus, safe and efficacious vector delivery is possible with synthetic systems such as those disclosed herein.

18. A Method of Transmitting a Gene without a Vector Any RNA transcript, such as an SP6 or T7 bacteriophage RNA, may be packaged into liposomes as described above together with reverse transcriptase and any molecule which can anneal to the RNA to provide a primer (such as oligo dT primer to permit copying of mRNA from the 3'-poly(A) tract). The cDNA generated using this procedure may be integrated into cellular DNA without retroviral or retrotransposon cis-acting signals, although the natural recombinase mechanisms for random DNA integration are not often as precise as reverse-transcriptase mediated mechanisms. In order to overcome this difficulty, a preferred method is to include at the termini of the RNA vector sequence the R or repeat region found at the ends of VL30 or other retrovector RNA, enabling the cDNA to replicate as a circle or concatamer. If the integration sequences found at the junctions of joined LTRs are included, along with primer binding sites, reverse transcriptase specifically recognizes these sequences, such as those found on the synthetic vectors of FIG. 2, and integrates them specifically into the recipient cell genome.

19. A Method for Adjusting the Equilibrium Between Packaging and Gene Expression Unlike cellular RNAs which are dedicated mainly to protein expression, retrovectors of all types have two major roles: transmission and protein expression. Since these two activities cannot efficiently take place at the same time, factors which influence the direction they take (either toward translation via polyribosomes, or toward packaging by virions) can have a powerful effect upon titer as well as protein expression levels. For example, consider a vector RNA such as VLPPBN. If a long region inserted into this vector is translated, large polysomes may form, repeatedly copying the information into protein molecules. However, if an AUG (initiator) codon in the 5'-untranslated region is quickly followed by a stop codon such as UAG, UGA, or UAA, the ribosome will disengage, releasing the RNA. Thus, the RNA becomes eligible for packaging once more. If several AUG codons are each successively followed by stop codons, then repeated starts and stops can be expected, regurgitating the vector RNA repeatedly and making it more eligible for packaging. If, however, one wishes to translate a protein from the vector RNA which initiates within the LTR, the presence of one or more confounding AUG codons (preceeding the genuine start site of translation for the desired protein) will significantly decrease the efficiency of translation. This is because the mechanism which is proposed for translation is believed to involve recognition of the 5'-cap structure, followed by scanning to the first AUG codon. Sometimes the first AUG codon is not recognized, and scanning continues. If an AUG codon is preceeded by a purine base three positions 5'- to the initiator AUG codon, then it is a preferred site for translation initiation. If the AUG is followed by a G base, it is more preferred. Thus, AUG codons and the stop codons which follow can have a powerful influence upon the direction (toward packaging or toward translation) which the vector RNA takes. This was not previously recognized by vectorologists. An example of the effect of ATG codons on packaging efficiency is shown in FIG. 11. The insertion of a single additional ATG codon to the left of the open reading frame for the neo gene caused an approximate threefold increase in of the transmissibility of the vector (compare VLDN to VLCN).

For gene therapy, it would be especially desirable to have a vector which has both high titer as well as strong protein expression. This can be attained by combining AUG start codons with splicing of the 5'-leader sequence. Unspliced vectors are packaged efficiently because translation is frequently aborted. In the recipient cell, processing of a 5'-intron containing AUG codons and packaging signals permit more efficient translation of a protein product, especially if it resulted in the removal of confounding ATG codons. Thus, it would be desirable to have a splice donor and acceptor site in the 5'-end of the RNA which would permit some percentage (less than 100%) of the RNA molecules to be spliced. Ideally, it would be desirable to have efficient splicing in the recipient cell, but not in the producer (donor, or helper) cell. The synthetic vectors shown in FIG. 2 have splice donor site concensus sequences just preceeding the packaging signal. It is possible to insert a splice acceptor sequence into a unique restriction endonuclease site, such as the Cla1 site of VLCN or its derivatives, or the Dra3 site of VLDN. However, in order for this to have greater effect, it is also desirable to mutagenize some or all of the confounding AUG codons which lie outside the splice region. This can be done by using any technique of site-directed mutagenesis (Ausubel, supra; or, for example, using the commercially available kit with manufacturers instructions, Stratagene #200510, La Jolla, Calif.; ref: Felts, K., et al. 1992, Strategies 5:26–28). Alternatively, it is possible to use a splice donor which is farther upstream, for example in the LTR. To enhance the dichotomous effect described and to achieve high levels of both packaging and translation, it is also desirable to position AUG and/or termination codons within the intron of the vector. A sample set of oligonucleotides is illustrated below for creating a region which has the following structural features: Cla1 compatible ends for insertion into VLCN; multiple advantageous ATG codons, followed quickly by termination codons for abortive translation; a splice acceptor site homologous to the AKV virus splice acceptor site (to give partial, but not complete splicing in cells); and several unique and useful restriction endonuclease sites.

ATGSACU UPPER STRAND, CLA1 OVERHANGS WHEN ANNEALLED, NO CLA1 SITE

5'-CGGAAATGATCATGGMTGATAAGATGACCTMCTAATAGCCCATCTCTCCAAGATCGATCAGGCCTAGATCT-3' (SEQ ID NO:15)

ATGSACB BOTTOM STRAND

5'-CGAGATCTAGGCCTGATCGATCTTGGAGAGATGGGCTATTAGTTAGGTCATCTTATCATTCCATGATCATTTC-3' (SEQ ID NO:16)

The two oligonucleotides were synthesized chemically using commercial phosphoramidite chemistry. The artisan can also order these or other sequences like them from many commercial firms (eg. Genosys, Houston Tex.). The sequences can be annealed (hybridized) simply by coincubating the two molecules in the presence of a salt solution. The resulting hybrid nucleic acid molecule (unphosphorylated) is a substrate for ligation to the Cla1 site of the digested plasmid, pVLCN, or pVLIL2EN (which should not be dephosphorylated after digestion with Cla1),. The ligation is typically performed using a 3:1 molar ratio of insert to plasmid, at 4 degrees C., using a DNA concentration of 20 micrograms/ml. After ligation, the plasmid is again cut with Cla1 and electrophoresed on a 0.8% agarose gel. Comparison of digested and undigested material, before and after ligation, permits identification of an undigestible band representing closed circular (relaxed) DNA, containing the desired vector. Excision of this band from the gel is followed by transformation of *E. coli*, and identification of candidate clones using standard techniques (Ausubel et al, supra). Analytical digestion of the plasmid with any of the unique sites included within the oligo sequence will be useful to help establish orientation and identity. By combining the AUG codons with the splicing strategy, an especially preferred type of vector, suitable to the needs of the individual investigator is attainable. This strategy can be applied to any retrotransposon or retrovirus-derived vector (or example, to achieve high titer and increased protein expression). In the examples depicted supra, the AKV splice acceptor site was used because it is slightly different from the MoMLV splice acceptor which is found in helper sequences (discouraging to homologous recombination). However, the investigator may use any other splice acceptor of choice, and the invention is not intended to be limited in scope to the examples given. FIG. 2H shows the synthetic construct in schematic form for VLATGSAF. VLATGSAR is the same except that the direction of the insert is reversed. FIG. 13A shows expression of RNA from a number of vectors, including the parent vector VLIL2EN, and derivatives of VLATGSA(F or R). These data demonstrate that a mix of spliced and unspliced RNA can be obtained from such a vector with a synthetic splice site. Other vectors with synthetic splice sites (VLPBNS and VLPPBNS) reveealled no evidence of splicing, but were expressed at greater steady state RNA levels. The vectors with ATGSA inserts appeared to have spliced RNA in the foreward orientation of the insert, but were expressed at reduced RNA levels regardless of whether the insert was foreward or backward. However, the parental vector was also expressed at reduced levels, indicating a reduction may have been caused by both the ATGSA insert as well as IL2EN inserts.

The disclosures above, and the explanation thereof were previously not known to vectorologists. For example, Mulligan et al disclosed a splicing retroviral vector which gave high titers and provided excellent protein expression (WO 92/07943; Guild et al, & USA/071607,252). However, the reasons for high expression, although associated circumstantially with a splice acceptor site, were not disclosed. In fact, the cryptic splice site was apparently included in the vector by accident. Similar vectors have since been constructed by other investigators. The present disclosure permits investigators to manipulate the vector to obtain the correct blend of expression and packaging by understanding the methodology described.

Previously, the effect of ATG codons in the 5'-untranslated region was similarly not well understood. For example, the vectors of Miller et al (Bio/Techniques 7:980-1989) (and all other retrovirus-derived vectors known to the inventor) contained ATG codons in the 5'-untranslated region, but the vectors functioned somewhat and thus the difficulty was apparently disregarded. The beneficial effects of splicing upon expression of protein from various genes have been anecdotally appreciated for some time. However, poor LTR-driven expression of protein has been a persistent problem of retroviral vectorology up to the present, confounding interpretation of early gene therapy experiments (for example see Anderson, C., Science 259:1391-, 1993). Therefore, given the disclosure of how translation and packaging work together, it is now possible for investigators to use the methods described herein to improve protein expression as well as transmission. Although the preferred embodiments are synthetic or retrotransposon vectors, the invention is equally applicable to retroviral-derived vectors.

FIG. 11 shows data from expression of RNA and protein from the various vectors. Addition of a single AUG codon to the VLDN vector in the form of a Cla1 linker (producing VLCN) resulted in an approximate 2–3 fold increase in titer, with minimal impact upon protein expression. Removal of the extended packaging region of VLPPBN resulted in decreased titer (see VLPBN vs. VLPPBN). Use of native (endogdenous) VL30 sequences present in helper cells provides decreased cloning space, but increased efficiency of transmission (titer). The investigator is here taught to use a natural VL30 element such as NVL3 to attain higher titer at the expense of cloning space. Thus, the spectrum of vectors shown here teaches the investigator to choose those characteristics most needed. None of the vectors shown in FIG. 2 naturally have a known or predominant splice acceptor site between the canonical splice donor site and the start site of translation.

20. Mapping the Genome

Mapping and sequencing the human genome as well as the genomes of model species has become an international scientific priority. In order to establish a good map, many contiguous loci must be established on the chromosomes. This can be accomplished by transducing a vector (such as those taught here) into the cell. For example, FIG. 12A, lane 1 shows an RNA blot of human HT1080 fibroblast cells which are uninfected, whereas lane 2 shows the same cells after infection with PA317 helper cells and various vectors. The expression of endogenous VL30 illustrates the presence of mouse VL30 in these human cells. The use of a vector to infect these cells permits the identity of VL30 sequences to point out particular loci on the chromosomes by hybridization, for example by chromosome painting or in situ hybridization methods (described in Ausubel et al, supra). In a preferred method, drug resistance is used to establish clones or mass cultures which have unique loci tagged with the vector. Many clones of cells infected in this manner can be purified by drug selection, for example after infection by VLPPBN, and the loci identified by the methods described. Thus, an ordered array of vector sequences integrated along a particular chromosome can be attained after examination of stained chromosomes obtained by fluorescence in situ hybridization (FISH). Since the ends of VL30 LTRs are of known sequence, they can be extended by assymetric PCR techniques (Ausubel et al, supra) to obtain the genomic DNA sequences flanking the integration sites. Several other techniques can be combined with this method to give more powerful usage. For example, bacteriophage lambda COS (packaging) signals or other phage packaging signalos can be combined with the vector to permit recovery of the locus from a restriction digest. One way to do this is to ligate the synthetic COS sequence between fragments of digested genomic DNA to permit lambda packaging. The genomic DNA from a clone or mass culture of infected (eg human) cells is digested to yield (eg 40 kb) fragments, some of which include the embedded VL30 loci. These are ligated to COS oligomers, and then packaged in bacteriophage lambda heads by in vitro packaging (eg. Stratagene Gigapack kit), or by similar techniques for other phages which permits packaging of much larger pieces of DNA. The phages infect bacterial cells where they circularize at the COS sticky ends and begin to replicate as plasmids due to the presence of plasmid replication origin regions also included in the vector. In a preferred embodiment, a reporter gene such as β-gal is included to permit easy visulization of clones. Thus, the eukaryotic cell clone is marked at the appropriate chromosomal loci, and at the same time it is cloned into $E.\ coli$ or a similar prokaryotic or yeast host to permit propagation as a plasmid or cosmid, together with flanking host sequences which mark the loci. In an additional improvement, the VL30 also contains a eukaryotic origin of replication, such as the SV40 viral ori to permit propagation of circular, marked loci in eukaryotic cells. In this case, the DNA is digested to include eukaryotic chromosomal flanking regions as before, but then it is ligated at low concentration (preferrably <20 $\mu g/ml$ total DNA concentration) to allow circularization. Then it is transfected into eukaryotic cells and selected with drug such as neo which is included in the vector to provide eukaryotic cells with episomal copies of the locus. Conversely, it can be propagated as a cosmid or phagemid as before, but then transferred to eukaryotic cells. This will permit expression of any genes in the flanking region which are intact enough to permit expression. The only eukaryotic cells surviving selection are those which contain the marked loci. In each case, the correct VL30 transcriptional unit is embedded in the circular, episomal chromosome. In an additional improvement, the clones are used in conjunction with a phage propagation system which permits larger pieces of DNA to be cloned, such as the phage P1 packaging system. In this case, appropriate modifications are made according to the manufacturers instructions (Genome systems Inc. St. Louis, Mo. 63143-9934) to permit efficient packaging. This permits propagation of even larger pieces of DNA. In an additional improvement, the marked DNA is cloned into eukaryotic double minute chromosomes or circular minichromosomes. The clones are selected using the drug marker found on the primary vector (the one used to mark the chromosome). This permits propagation of megabase-sized pieces of DNA. In this embodiment, fewer clones would be needed because each would span a larger segment of DNA. In an additional improvement, a linker is inserted at the circle joint when the DNA is extracted from the genome. The known sequence of the synthetic linker or of the restriction site permits sequencing bidirectionally from the joint using a complementary PCR primer, correctly identifying the circle junction (ends of the genomic element). In additional improvement, transcriptional activity of the VL30 LTR inserted into the genomic DNA can be used to express nearby genes downstream from the locus. This RNA can be used to make probes for natural gene expression/insertion or to express proteins encoded within the locus. Interesting changes in expression can be correlated with changes in the cell phenotype to identify interesting new genes. Thus, the vectors and methods presented herein can be used to map and sequence the human genome in an ordered way, or to create selectable mutations in specific genes, using an array of contiguous, proximal, or overlapping clones identified visually or biochemically. To facilitate such work, use vector VLPSNO, which contains several improvements as shown in FIG. 2$i$. First, the VL30 genome is permuted with a single LTR flanking the internal sequence. The former SnaB1 site of NVL3 is converted via Not1 linkers to a unique Not1 site, into which is inserted a sequence containing the SV40 ori-early promoter region. This sequence is used to transcribe the neo gene in eukaryotic cells, however, it also functions as a kanamycin resistance marker in $E.\ Coli$ cells. To the right of the neo gene is a bacterial plasmid origin of replication, which enables the plasmid form of the vector to replicate in $E.\ coli$ cells. The single LTR prevents homologous recombination during cloning of foreign genes into the VL30 (thus facilitating recovery of genuine recombinants vs. LTR deletion mutants). For ease, unique Bgl2 (compatible with Bam HI, Bcl1) and Sal1 restriction endonuclease sites are located in the immediate 5'-flanking sequence of the insert. This enables foreign DNA to be cloned into essentially the same site, providing minimal disruption of the packaging signals of the VL30 vector. Thus, this vector can be used either for transmitting or expressing therapeutic genes, or for marking chromosomal loci and recovering the loci as transfected plasmids or phage-transmitted plasmids, or as enkaryotic viruses capable of expressing the genes in cultured cells.

21. A Method for Reconstituting an Animal using Hematopoietic Stem Cells, and for Treating or Curing Diseases Such as Sickle Cell Anemias, Thallasemias, etc.

Various methods have been devised for isolating and partially purifying hematopoietic stem cells (primitive blood cells which develop and differentiate into all the cells of the blood lymphoid, myeloid, and erythroid cell lineages). Generally, these involve rescueing stem cells from the bone marrow or peripheral blood, for example using antibodies which recognize stem cells (e.g., CD34). Such methods would potentially permit reintroduction of genetically engineered blood stem cells (BSC) into the blood. For example, an animal could be irradiated to kill the bone marrow, and autologous or heterologous bone marrow stem cells or their derivatives (progenitors of various blood cell lineages, or fully differentiated blood cells) could then be introduced into the animal. If stem cells were reintroduced exclusively into an irradiated animal, the animal would be permanently changed with respect to any altered genetic material in the cells. Many common disorders of blood or amenable to blood therapy have been identified. A major problem has been to identify and purify BSC, which may require stroma or other types of cells in order to remain viable in the undifferentiated state. Several growth factors have been identified which can promote the cultivation of BSC. For example, the combination of interleukins 3, 6 and Steel factor are used. A promising finding is that leukemia inhibitory factor (LIF) is useful for maintaining BSC in culture.

However, to efficiently transduce undifferentiated BSC, better methods are desired. Conventional vector transduction into stem cells is seriously impeded by their lack of ability to proliferate and remain undifferentiated. One possibility is that when BSC divide normally in culture, they differentiate. Thus, the multipotent state is lost. If BSC are sometimes self-renewing, then the mitotic cells into which retrovectors insert will be conserved in the undifferentiated state, and could be used to repopulate the animal with permanently altered bone marrow. Ideally, a single stem cell clone should be transduced. Unfortunately, retroviral vectors are often transcriptionally inactivated in primitive cells. In addition, BSC in a nonmitotic state are retractile to infection by retroviral derivatives. However, the usefulness of the MoMLV-derived vectors in blood cells is enhanced somewhat by the fact that they are blood-tropic. This was no doubt important to the partial success of the early gene therapy trials affecting severe combined immunodeficiency (adenosine deaminase deficiency). However, therapy using non-stem cells must continue long term due to the inability to correctly and efficiently identify and alter BSC. Marker experiments have shown that one or at most two BSC could reconstitute an animal. However, the technology of identifying, transducing, maintaining in culture and transmitting the engineered cells is not efficient. Treatment of lymphocytes with retroviral vectors has demonstrated that some self renewal has occurred, thus some apparently self-renewing cells (perhaps BSC) have been targeted in mass cultures of infected cells. However, this targeting is circumstantial and is not discreet, efficacious targeting. Ideally, the cells should be induced to proliferate efficiently while in culture so that the vector could be efficiently introduced while the cells remain in the undifferentiated state. Thus, small populations or single cell clones could be characterized to perfection in culture using special vectors known to express in a variety of cell lineages including blood cells and primitive cells, and these could be used to reconstitute the blood of individuals afflicted with common disorders such as those mentioned above, or those which are foreign to blood but which might be amenable to blood-bourne therapy.

A promising new technique has recently been devised [Rogers et al, Proc. Nat. Acad. Sci. (USA) 90:5777–5780, 1993] which permits the artisan to control proliferation of BSC, and thus permits the introduction of a retrovector such as VLATGSAF, VLPPBN, VLCN, or any other retrovector during self renewal. A major advantage of the method is that it does not require the use of CD34+ purified BSC. In this method, a bone marrow plug is cultured in vitro as described by Rogers (supra) for approximately 30 days, using prescribed mycophenolic acid treatment to destroy all mitotic cells. Then, tumor necrosis factor (TNF) is added in the absence of mycophenolic acid in order to induce proliferation of BSC.

We now disclose that during the early stages of proliferation under the influence of TNF (or other proliferation inducing factor), a supernatant containing the retrovector particles (for example, a helper cell line producing the VL30-derived or other retrovector) is added to expose the mitotic BSC to the vector. Ideally, the vector contains a marker such as neo, β-galactosidase, etc., to permit the identification of clones of cells later. Since the BSC are apparently the majority of mitotic cells in the culture, they will be predominantly affected by the vector. Since differentiated cells form colonies in agar and eventually die after terminal differentiation, it is possible to identify clones of cells arising from transduced BSC after growing the marrow in culture for six months (longer than the survival of differentiating, non-stem cells). Either drug selection (in the case of a selectable marker such as neo), or vital staining (in the case of a reporter gene such as β-galactosidase) can be used to purify or visualize the cells, respectively. Such long-term surviving BSC can then be used to reconstitute bone marrow. In a preferred embodiment, the vector is derived from VL30 or a synthetic vector such as the NVL3-derived vectors described herein (which are expressed in human lymphocytes in culture). If high levels of LTR-driven transcription are desired, it is possible to substitute the use of the LTR transcriptional promoter of BVL-1 (Hodgson et al, 1983) or a promoter similar to BVL-1 which has been shown (Park et al, Blood 82:77–83, 1993) to be especially transcriptionally activated during erythroid differentiation, in response to the blood factor erythropoietin. The gene amplification methods described above also permit promoter substitution or traping from a library (or directly from tissue), and thus allow the investigator to adapt the promoters to natural murine counterparts expressed in specific cell lineages without requiring direct access to any special materials except the animal (or cells, cell lines or tissues of the animal). Alternatively, an internal promoter from another gene such as globin can be used to obtain equimolar ratios of proteins in the cells (such as the globin gene promoters) which may be desired to complement existing proteins or subunits. A primary advantage of the instant invention is its ability to be expressed in human blood cells (FIG. 12B), permitting it to be used for selection of genetically engineered cells in vivo.

22. Gene Transfer using Retroelements and Retroposons without Long Terminal Repeats Many retroelements are found in the genomes of man and other species which lack the packaging signals and retroviral genes necessary to transmit intercellularly via retroviral particles. We have shown how the packaging signals of VL30 permit this RNA to transmit efficiently via standard helper cells. However, other types of retroelements also have the capability of reverse transcription and insertion into the genome, but lack the ability to be packaged. Therefore, it follows from the teachings and disclosures contained herein that the packaging signals such as those contained in VLPBN, alone or in combination with the increased packaging signals contained in VLPPBN, or the special enhanced functions contained in the identified spacer regions of endogenous VL30 loci, can be utilized in other types of retroelements to permit retrotransposition via virions, since the other functions necessary for retrotransposition are already present in these elements. In this way, it is possible to transmit and/or express genes via elements such as LINES (long interspersed elements in man and related species), ALU (short retroposons in mouse, man, and others), and similar elements which do not bear long terminal repeats, which may not otherwise move between cells.

23. Reconstitution of Bone Marow and Blood using Embryonic Stem Cells: a Stem Cell Vector A consideration which was apparently overlooked during the search for BSC pure cultures was that blood cells are able to differentiate very quickly during embryogenesis. For example, red blood islands are visable in chick embryos after just one to three days of incubation, starting with a fertile zygote. Therefore, the blood stem cell quickly differentiates from the pluripotent ES cell. Furthermore, it may be unnecessary to search for primitive blood cell markers such as CD34, especially if such cells are already restricted as to their potential. Such restriction may also mark them as blood progenitors, which are already partially differentiated or restricted, or they may not be immortal. Since any restriction on pluripotency is potentially deleterious, it is desirable to replace techniques using blood stem cells with those using pluripotent embryonic stem (ES) cells. For example, if ES cells are stimulated with plant lectins such as ConA, they differentiate into lymphoid cells. Since the factors normally necessary for differentiation into the lineages of blood are present in the bone marrow and its associated stroma, it is desirable to insert ES cells into the bone marrow in order to permit their differentiation into mature blood cells. The key elements to success are: (1) maintaining good stocks of ES cells (ie. non-aneuploid, non-differentiated); and (2) inserting the ES cells into the appropriate microenvironment). Alternatively, the method for growing BSC from marrow cultures described by Rogers et al, supra, may also be used to cultivate BSC in culture from added ES cells. In one modification of the above procedure, the mycophenolic acid treatment described by Rogers is repeated in the presence of TNF to kill off proliferating BSC in the marrow culture. The genetically engineered ES cells (preferably a single clone) are then added to the culture, and the cells are grown in TNF without mycophenolic acid to permit outgrowth of BSC derived from the ES cells. In one modification, the mycophenolic acid treatment can be repeated at any time to kill ES cells which are proliferating but which are not becoming a part of the BSC (for example, ES cells on the periphery of the culture), sparing quiescent blood stem cells derived from the introduced ES cells. A stem cell vector such as the instant VL30 vector VLPPBN can be used to transduce ES cells selectably in culture (Cosgrove et al, J. Cellular Biochem. 17E:235, 1993). Such cells can also be modified with respect to the histocompatibility antigens, either by gene knockout procedures (Cosgrove et al, Cell 66:1051–1066; Benoist et al, WO9211753), or by insertion of histocompatibility genes using the instant invention. Thus, ES cells can be used to design blood histocompatibility antigens for individual recipients, using the vectors described herein to deliver the new histocompatibility antigens, as well as to deliver therapeutic genes to bone marrow transplantation recipients. It follows that human ES cells, once isolated, can be histocompatibility-modified for insertion of genes into many recipients. Thus, blood can be transplanted from these primitive cells to correct genetic defects via ES cells. In the past, a major problem was that BSC would not proliferate efficiently in pure culture. However, ES cells proliferate in the presence of fibroblast feeder layers or in the presence of leukemia inhibitory factor (LIF), therefore, the problem is circumvented. However, another problem which exacerbated effective gene therapy of ES cells was the fact that these and similar embryonal carcinoma cells (Robertson, et al, Nature 323:445–448,1986; Stewart et al, Proc. Nat. Acad. Sci. (USA) 79:4098–4102) would quickly inactivate transcription from MoMLV retroviral vectors used to transmit genes to cells. This necessitated tiresome screening procedures to identify the clones (see Robertson, supra). Furthermore, MoMLV vectors are transcriptionally inactivated in BSC (Challita et al, J. Cellular Biochemistry, 17E:229, 1993). However, Cosgrove et al, supra, illustrate that the instant invention enables VL30 retrotransposons and their synthetic derivatives to selectably express RNA and protein in ES cells, permitting recovery of clones and saving tiresome screening procedures which were previously required. More importantly, since endogenous VL30 retrotransposons are also effectively expressed in vivo in the mouse, the problem of inactivation of retroviral vectors in vivo (reviewed in: in Richards and Huber, Human Gene Therapy, 4:143–150, 1993) is also overcome. A major advantage of the instant invention is thus that it enables improvements in the use of ES cells as a vector. An instant advantage of working with pluripotent cells is that, since they are perpetually self-renewing, it is never necessary to replenish them in vivo once they are established. Technology such as CD34 purification of blood stem cells is not required. Many diseases of blood, such as sickle cell anemia, thallassemias, immunological and clotting disorders, can potentially be treated by modification of blood using the materials and methods described herein. Equally important, many other disorders which are not restricted to blood are amenable to gene therapy through blood, as blood nurtures each organ and can thus deliver many compounds and enzyme activities to such tissues.

24. Expression in Primary Cells: Mammary Expression System, and Applications to Transgenics A major difficulty of retrovirus-derived vectors has been that they are expressed easily in transformed cells and lymphoid cells, but are poorly expressed in primary cells or in vivo (re; in Richards and Huber, supra). Using an internal promoter marginally improves their performance in nonlymphoid cells, although they are still restricted by the inhibition of the enhancer elements located in the LTRs. Ideally, the vector of choice should insert the foreign genes into regions of active chromatin, and the transcriptional enhancers should not be heavily methylated. More ideally, the enhancers should be very active in the mammary gland, permitting higher levels of gene expression at the target locus (ie., of the recombinant product). Most ideally, a hormone-regulated expression should be enabled, permitting the investigator to use either the flanking enhancer with mammary promoter or with the vector transcriptional unit (the LTR).

Figure 12A:
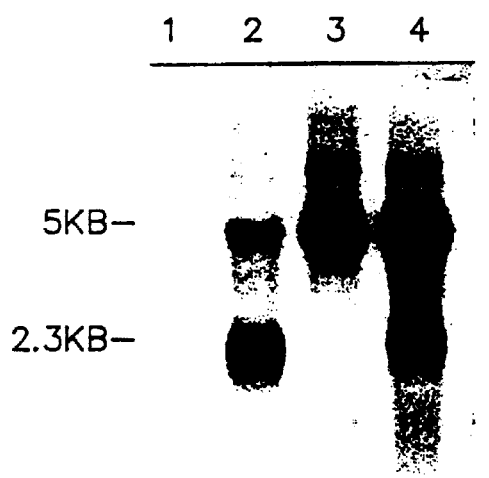
Figure 12B:
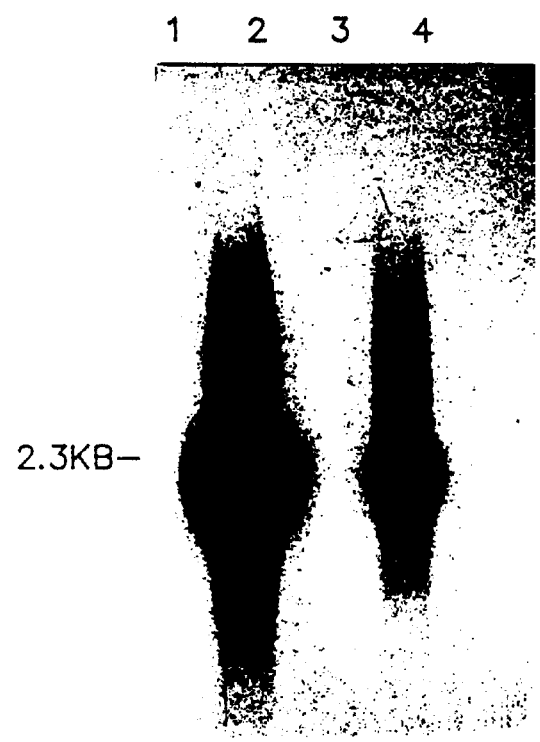

Fortunately, the novel vectors described herein (such as the prototype VLPPBN) are have some or all of these desirable characteristics, depending upon context. FIG. 12A discloses RNA blots, hybridized to a VL30 probe, revealling abundant expression of RNA from the NVL3 promoter in normal human mammary epithelial cells (NHME) (from Clonetics Research, La Jolla, Calif.). Expression was found to be elevated significantly by insulin stimulation. Similar experiments showed that the NVL3 LTR promoter can be up-regulated by insulin and/or basic human fibroblast growth factor in mammary MCF7 cells.

The usefulness of this preferred embodiment (a mammary cell culture system for production of recombinant gene products) can also be extended to the whole animal using the transgenic methods already disclosed, or by using the unique ability of retrotransposon vectors such as VL30 to be expressed selectably in pluripotent embryonic stem cells (ES cells) (Cosgrove, Chakraborty, Grunkemeyer, and Hodgson, 1993, J. Cellular Biochem. 17E:235), which cells can be injected into embryos and used to generate chimeric and transgenic animals FIG. 12 demonstrates that the instant vectors are readily expressed as RNA in primary cell types (such as lymphocytes and mammary cells), as well as in transformed cells, including human cells. Selectable expression of neo protein was detected in primary cultures of human fibroblasts, mammary epithelia, and lymphocytes. Selected human peripheral blood lymphocytes transformed with Epstein Barr virus (mostly B cells) expressed significant vector RNA as detected by northern blot analysis. Importantly, mammary epithelia also expressed significant amounts of RNA from the LTR promoter. The instant invention can thus be used for mammary gland expression of gene products. Mammary expression of proteins is an important mode of production of recombinant materials which can be extracted from milk. Thus, a mammary vector is a major enabling step in the production of useful transgenic animals. Furthermore, since ES cells bearing vectors can be obtained by drug selection with the same vector therefore, ES cell-derived transgenics made from the instant invention enable mammary cell or milk production of proteins of value. One mode is to use the natural mammary expression property of an instant vector such as VLPPBN to enable LTR-driven protein expression, such as the illustrated example where neo protein and RNA was expressed in human mammary cells in culture. Another mode is to use the mammary specificity of the LTR to augment expression from an internal promoter with known mammary specificity, such as casein promoters, whey acidic protein promoters, lactoferrin promoters, etc., which are known to be active in the mammary gland and which will permit mammary-specific expression of recombinant proteins. An advantage over transfection methods such as microinjection which have been used to deliver genes for mammary expression to the zygote is that the tremendous variability of expression which is frequently observed in such transgenic animals may be reduced because the sequences are integrated as single copy genes flanked by the active mammary enhancer sequences of the LTR. The ability to preselect for expression in ES cells is an advantage which can be appreciated over animal selection methods, especially when the cost of large transgenic animals is considered. Thus, it is advantageous to perform selection at the ES cell stage where hundreds or thousands of clones can be prescreened in vitro prior to the expensive process of transgenic animal production.

In a somewhat different mammary expression method, the mammary duct can be perfused by helper cells or helper virus, to permit transduction of proliferating cells (ideally during development when proliferation is optimal). Preferably, the gland should be rinsed with saline to remove colostrum or milk materials before perfusion via the teat canal. Ideally, the mammary should be at a very early stage of development, and the vector producer cells should be injected directly into the mammary fat pad at an early time during development to permit the primordial cells to be genetically altered at an early stage of proliferation. Vector producer cells making the vector, or media supernatant from such cultures can also be perfused up and into the canal, permitting it to enter the mammary alveoli where it is exposed to proliferating mammary cells. Ideally, the gland should be in a highly proliferative state in order to permit efficient transduction. This state is induced naturally during pregnancy, or can be induced hormonally. Vector producer cells or supernatants can be injected into the mammary fat pad just prior to or during hormonal stimulation to enable early lineages to become infected and to proliferate during later stages of mammary development. In this manner, proteins can be produced in the milk of chimeric animals without the need to develop lines of pure transgenic animals. Although the vectors illustrated here are preferred embodiments, the methods and procedures described are not intended to be limited in scope to the examples given.

25. Splicing and Expression of RNA and Protein using the Instant Invention

The vectors of the instant invention contain at least one canonical splice donor site, identified as SD on FIG. 2. However, each cell has unique capabilities for splicing which can be utilized for context specific expression. FIG. 12C(6) shows at least three messenger RNAs containing VL30 sequences from cells transduced by VLPPBN. The RNAs may represent the ability of colon cancer cells to splice the vectors at unusual sites. FIG. 13 also shows the spliced and unspliced mRNA sequences which are expected from the vector VLATGSAF (explained in section 19), but not from the control experimental vector VLATGSAR, in which the oligonucleotides are inserted in the reverse orientation. These vectors contain ATG codons followed by termination codons, to encourage packaging, but ATGSAF also contains a splice acceptor site downstream from SD, to encourage a spliced mRNA which will permit efficient translation of protein without interference from the numerous false ATG codons located upstream (ATGSAR is a negative control in which the ATG-splice acceptor sequence is inserted in reverse). In addition, a putative SD site also exists in the LTR. Both spliced and unspliced mRNAs were observed, indicating that more than one gene may be expressed from the LTR promoter, and lessening the need for internal promoters which could lead to problems caused by promoter interference. Thus, alternative splicing pathways are an object of the instant invention.

26. In vivo Gene Introduction into Animal Embryos

The ability to generate transgenic animals would be greatly facilitated by methods which permit the direct introduction of genes into the embryo to generate chimeric or mosaic animals which could then be bred to generate transgenic offspring which were either heterozygous or homozygous for the trait. The technique would be especially advantageous for avian species, such as chicken, where retroviral (Salter et al, Virology 157:236–240, 1987), microinjection (Love et al, Bio/Technology 12:60–63, 1994) and primordial germ cell methods (Vick et al, Proc. R. Soc. Lond. B 251:179–182, 1993) have been successfully used, but not perfected. In addition, it would permit the expression of proteins in the eggs of the avians, where said proteins could be purified and used for industrial purposes without harm or invasive procedures to the animal.

In a preferred embodiment, a supernatant from helper cells, or a supernatant containing vector producer cells, is injected directly into the blastoderm tissue of the early (day zero) chick embryo, and the egg is incubated to term. Up to 0.2 mls of cell culture fluid together with $\geq 1 \times 10^6$ cells can be injected without harm into the day zero embryo. To facilitate injection, a hole can be drilled in the large end of the egg over the airsac (0.5 cm, using a sterile dental drill). After visualizing the blastoderm through the airsac inner membrane (one hour of preincubation of the egg at 37° C. makes the blastoderm easier to see through the membrane, as it poistions itself directly under and against the membrane), the vector fluid is injected directly into the blastoderm using a hypodermic needle (such as a 1 ml tuberculin syringe fitted with a 18–20 ga. needle). After manipulation, the hole is closed by using first aid tape (3M company, St. Paul, Minn.) or preferably by sealing a cover slip over the hole using a bead of hot glue from an electric glue gun to fuse the glass over the hole. After hatching, PCR is performed on the blood of the animal to determine whether the genes are inserted into the animals cells, creating a mosaic or chimeric animal. FIG. 13B&C. shows PCR results from chicken blood of animals which had been subjected to $1-5 \times 10^6$ PA317 cells containing VLOVBGH. Five out of six PCR-tested animals were positive for insertion of the OVBGH construct, which consisted of an oval-bumin gene promoter and a bovine growth hormone cDNA in the vector VLPPBN. The less sensitive method of DNA blot analysis reveealled the expected bands in at least two of the six animals. Five out of six animals remain alive and healthy after six months. All three hens laid eggs. One male animal had a behavioral abnormality and was subsequently sacrificed. The vector VLOVBGH is designed to use the oviduct-specific ovalbumin promoter to express the bovine growth hormone gene specifically in the oviduct for production of the hormone and secretion into the egg. Such expression requires that an appropriate signal peptide be present on the protein sequence to permit secretion into oviducts. The animals developed normally, and laid eggs which were at first somewhat smaller than normal. Prior art (e.g., Love et al, supra) teaches that chimeras such as the above can be bred to produce transgenics. A similar strategy of somatic gene therapy, or mosaicism, enabled the production of proteins in the liver, using chickens (Cook et al, J. Poultry Sci. 72:554–567, 1993), except that a virus was used (avian sarcoma-leukosis virus) which permitted transgene expression but which resulted in death of the chickens from viral neoplasms. An additional problem with replication-competent virus vectors such as those of the Cook et al. example cited supra is that rearrangements frequently took place, resulting in changes in gene structure which interfere with expression. Therefore, the vectors of the instant invention which are typically stable long term, are preferable to retrovirus-derived vectors.

27. Making Human or Animal Gene Libraries using a Vector

The instant vectors are potentially able to transport 6–10 kb of foreign gene sequences, and to express them in many types of mammalian cells and tissues after transduction as described above. It would be desirable to create expression libraries of genes which would permit identification of the gene or phenotypic expression of the gene in a recipient cell. In a preferred embodiment, human or animal DNA is digested with an enzyme such as Mbo1 or Sau3A restriction endonucleases which digest DNA into very short fragments (average size, ~256 bp), depending upon its methylation status. The DNA is only partially digested to create fragments with an average size of 2–10 kb, depending upon the purpose of the library (short fragments may be more useful for expression of short genes or individual exons or groups of exons, while long fragments would enable the exxpression of larger genes or gene fragments). The DNA (which, in the above example has BamH1 compatible ends, due to the overhang sequence of Mbo1 or Sau3A enzymes) is isolated from a gel or gradient and is cloned into the compatible site of vector of choice. If the investigator wishes to express the gene from its own endogenous promoter, the gene can be cloned into the BamHl site of a vector such as VLPPBN (FIG. 2). If expression of RNA from the VL30 promoter is desired, the gene may be inserted into the BamH1 site of a vector such as VLSVP, which is VLPPB with an SV40 viral (early) promoter-driven puromycin resistance gene (for selection). Thus, an ATG initiation codon in the inserted gene or in the vector permits expression of the protein from the NVL3 promoter-initiated (or genomic) RNA. Another modification of this procedure is to include splicing signals to permit expression of the genes as spliced RNA. After transduction via producer cells such as PA317, the genes may be expressed in human or animal cells, depending upon need. The library can be screened via DNA or RNA hybridization, as well as by epitope screening using various antibodies against the desired protein. Thus, this embodiment is an alternative to expression libraries such as those made using the *E. coli* GT11 bacteriophage (ref. Ausubel et al, supra), where the expression of protein may not be modified as in an animal. An alternative embodiment is to include in the vector gene sequences derived from cDNA made from cellular RNA. In this case, linkers compatible with BamH1 or other appropriate restriction enzyme are attached at the ends of the cDNA to permit facile cloning into the vector. Such sequences should contain natural ATG codons and uninterrupted open reading frames, enabling the production of the cloned proteins in eukaryotic cells. Yet another embodiment is to use counter-selection as a screening method to obtain cells expressing the gene of interest. That is, the recipient cells for example having a (eg. auxotrophic) mutation are grown in supplemented medium during transduction with the vector library and subsequently during selection for the vectors in mass culture with a marker drug such as neo. However, the medium is not supplemented after the initial selection process. This enables the outgrowth of clones expressing the gene of choice (eg., the auxotroph target gene). This facilitates the cloning of genes for which a selectable phenotype exists, but for which no gene or antigen or antibody is known to exist. All that is needed is: (1) a counter-selectable cell line from an affected individual (or a mutation generated in cell culture), and (2) the library of human (or other organism) genes in vector format. This type of procedure is expected to greatly facilitate human gene therapy, because the selected genes which correct the disease phenotype are already being expressed in a functional and useful gene therapy vector, which can be rapidly and easily recovered (by PCR amplification or reverse PCR of the entire vector, or by superinfection with murine or primate type C retroviruses or helper to rescue the VL30 clone in a transducible format). These vectors are used to treat the affected individual's cells, ex vivo or in vivo. Thus, useful gene therapy is enabled without the prior identification of the affected gene. This procedure can be used to obtain treatments for many of the 5,000 or so known hereditary disorders, or for the rescue of recognition sequences such as antibodies (as antibody-producing genes) which can be used to modulate, ablate, or destroy other molecules or infectious agents such as oncogenes, bacteria and viruses. A special embodiment is one in which the antibody is also catalytic. This method enables the production of new enzymes using antibody technology to make antibodies against molecules designed to mimic the transition state of the desired reaction, then using the enzymes to perform complex metabolic tasks as a result of gene therapy using the vector. In addition, the simplified type of screening described here eliminates the construction of individual vectors, screening, expression testing for effectiveness, etc. The desired growth and regulatory characteristics of the vector can instead be determined directly by mass transduction of the cells affected. The recombinant DNA methods, and procedures for screening the libraries are found in Ausubel, supra. In an especially preferred embodiment, these methods are combined with stem cell techniques described above, wherein the therapeutic gene restores function in defective ES cells or other stem cells, and is then used to reconstitute a defective organ or tissue, such as blood.

28. Method of Screening for Titer-increasing Genes for Vectorology: The Horserace Technique Many types of DNA sequences are helpful for promoting efficient vectorology, for example by enhancing packaging into retroviral virions. Random cloning can be used to select for such sequences. For example, libraries such as those in the preceeding section can be repeatedly passaged from ecotropic to amphotropic, etc. by ping-pong (Bestwick, supra) or by simple serial passage of filtered supernatants between complementary helper cell lines (such as ψ2 and PA317). After several passages accompanied by drug (selectable marker) selection at each step, the most efficiently passaged vectors will predominate over those which are inefficiently packaged and transmitted. Thus, the survivors of the horserace will be the most efficient. Conversely, vectors constructed by subcloning sections of the VL30 genome can also be selected using the horserace method.

29. Autoexcision of an Episomal Vector: Delivery into Cells, Tumor-specific Expression, and Choice of Integrated or Autonomous Existence.

Among the known promoters of VL30 are those for tumor-specific or transformation-specific expression, including NVL1 and NVL2 (Carter et al, supra). These enhancer-promoter combinations can therefore be incorporated into the method of the instant invention for obtaining enhanced expression in cancer cells. However, it may also be desirable to obtain amplified, episomal copies of genes which are very strongly induced by cancerous or transformed cells. For example, genes could be expressed by this mechanism which would kill nearby cells through the bystander effect, also called metabolic cooperation. This is possible using a viral vector, such as minute virus of mice (MVM), however, the titers of this virus are very low ($\sim 10^2$/ml), making it near useless as a human genetic engineering tool. However, by combining the MVM reduced genome (FIG. 14) with a VL30 vector as shown, it is possible to use helper cells or other mechanisms as described herein to deliver the retrovector containing the parvovirus genome into the cell with the same efficiency as the retrovector. Once inside the cell, the retrovector makes a DNA copy of itself, including the parvovirus genome. Autoexcision of the parvovirus is permitted through the involvement of cellular mechanisms together with the viral protein, NS (nonstructural), activated from the vector. The P4 and P38 promoters shown in the preferred embodiment, MVM, are strongly activated in transformed cells. The P38 promoter can express a therapeutic gene, such as the herpes thymidine kinase gene (which is useful for bystander-effect killing of tumor cells by drugs such as gancyclovir). The excised MVM minigenome containing the therapeutic gene replicates autonomously as a single-stranded DNA genome, amplifying the copy number. The promoter is activated strongly in response to the transformed state of the cell, as much as 100–1000 times its normal activity. The essential parts of the parvovirus vector genome are the inverted terminal repeats (ITRs), the P4 promoter and NS gene, the P38 promoter, and a structural or therapeutic gene linked to expression from the P38 promoter (the exact sequences which are sufficient as cis-acting sequences for replication of the MVM minigenome are described in detail in Tam and Astell, *Virology* 193:812–824, 1993).

In a variation of this preferred embodiment, an alternative parvovirus, adeno-associated virus 2 (such as AAV2) is included in the retrovector such as VLPPBN. This parvovirus also excises from the genome after formation of vector DNA in the recipient cell. However, it can integrate within the human genome, often at a specific site, making it permanent within the cell. Thus, any gene can be delivered to cells for expression by these vectors without having to use DNA virus helper systems which are prone to the production of replication-competent virus.

30. Chinese Boxes: Transposons within Retrotransposons, and Vice Versa.

In addition to retroelements, cells also carry DNA based transposons such as the Ac/Ds elements of maize which were among the first characterized mobile genetic elements (McClintock, Cold Spring Harbor Symposium of Quantitative Biology, 16:13–47, 1952; ibid. 21:197-, 1957). Like retroelements, some DNA-based transposable elements encode a gene for enzyme activity facilitating transposition (transposase), while other transposable DNA elements rely upon other transposons to provide that function. Therefore, it is possible to transmit a DNA-based transposable element into a cell by enclosing it in a retrovector such as the preferred vectors described herein. After being inserted into the genome, the transposable DNA element is free to excise and wander within the cell genome. Occasionally, the excised DNA is lost, making this a convenient way to get a desired gene into the cell by means of selection, and eliminating the unnecessary selectable marker subsequently by excision of a transposable element carrying the marker. Conversely, a single integrant gene can move within the cell, providing a number of embodiments for gene expression which can be selected or permitted to evolve spontaneously as in nature. A fundamental prerequisite is that the transposase function must be provided, either in cis or in trans, to enable the transposon to excise. This combination of mobile genetic elements essentially provides DNA based elements with the ability to move between cells. On the other hand, it can be viewed that RNA-based mobile elements have been given the ability to mobilize or to excise certain sequences which can move within the cell, without reverse transcriptase. The reverse situation, where a retroelement such as the preferred vectors is included into a DNA transposon, is less directly practical. In this case, the DNA transposon must get into a cell and integrate. Then, in the presence of a reverse transcriptase (which could be found within the cell, or be exogenously provided by virus, helper sequences, etc.) the retroelement RNA will be reverse transcribed or packaged into viral particles. This system may be useful, however, in situations where DNA elements and transposase enzyme are transfected into the cell together to facilitate stable integration into the genome. DNA transposons may thus be used as a platform for integration, or for launching retroelements from within.

I claim:

1. A vector for transferring and expressing nucleic acid sequences comprising vector sequences, the vector sequences comprising linked:
   (a) a 5' long terminal repeat (LTR) sequence from a VL30 retrotransposon comprising a transcription initiation site for RNA;
   (b) an encapsidation sequence positioned 3' of the 5' LTR;
   (c) a primer binding site sequence from a VL30 retrotransposon positioned 3' of the 5' LTR;
   (d) a 3' LTR sequence from a VL30 retrotransposon positioned 3' of the primer binding site, wherein the 3' LTR includes:
      (1) sequences which cause polyadenylation of a RNA transcript initiated in the 5' LTR;
      (2) sequences which provide a primer for reverse transcription of the RNA transcript from step (d)(1) into a double stranded cDNA;
   (e) a polypurine tract sequence from a VL30 retrotransposon located 5' to the 3'LTR; and
   (f) sequences within each LTR which are cleaved prior to integration of the vector into the genome of a recipient cell,
   wherein the vector sequences comprise no more than 2 kbp.

2. The vector of claim 1 wherein the encapsidation sequence is from a VL30 retrotransposon.

3. The vector of claim 1 wherein the vector sequences are mouse VL30 retrotransposon sequences.

4. The vector of claim 1 selected from the group consisting of VLPB, VLPP, VLPPB, VLPPBN, and VLPPBNS.

5. The vector of claim 1 further comprising at least one ATG codon, positioned 3' of the transcription initiation site for RNA located in the 5' LTR, followed by a short open reading frame so that RNA transcripts initiated in the 5' LTR and terminated within the 3' LTR of the vector are more efficiently packaged into virions than the RNA transcripts are translated by ribosomes.

6. The vector of claim 1 further comprising sequences recognized as splicing signals, positioned 3' of an initiation site for RNA transcripts located in the 5' LTR.

7. The vector of claim 1 wherein the 3' LTR further comprises a transcriptional unit.

8. The vector of claim 7 wherein the transcriptional unit is a VL30 transcriptional unit.

9. The vector of claim 7 wherein the transcriptional unit is obtained by amplifying DNA or messenger RNA sequences comprising a preselected transcriptional unit using oligonucleotides which comprise a nucleic acid sequence obtained from the preselected transcriptional unit.

10. The vector of claim 1 further comprising at least one nucleic acid sequence comprising an open reading frame.

11. The vector of claim 1 further comprising a DNA sequence which comprises a DNA transposon.

12. The vector of claim 1 further comprising a DNA sequence which comprises DNA obtained from a virus.

13. The vector of claim 1 further comprising at least one DNA sequence encoding a protein.

14. The vector of claim 13 wherein the DNA sequence encodes a toxin.

15. The vector of claim 14 wherein the DNA sequence encoding the toxin comprises two exons.

16. The vector of claim 15 wherein exon 1 of the toxin gene is inserted within the 3' LTR of the vector and is operably linked to a transcriptional unit, and exon 2 is inserted 3' of the 5' LTR of the vector and 5' to the 3' LTR of the vector.

17. The vector of claim 10 wherein the DNA sequence encodes a reporter gene product or a selectable marker gene product.

18. The vector of claim 10 wherein the DNA sequence is followed by a poly(T) tract.

19. The vector of claim 13 wherein the DNA sequence is operably linked to an internal transcriptional unit.

20. The vector of claim 19 wherein the internal transcriptional unit confers tissue-specific transcription, hormone-specific transcription, or developmental-specific transcription.

21. The vector of claim 19 wherein the internal transcriptional unit is obtained by amplifying DNA or messenger RNA sequences comprising a preselected transcriptional unit using oligonucleotides which comprise a nucleic acid sequence obtained from the preselected transcriptional unit.

22. The vector of claim 19 wherein the internal transcriptional unit is a VL30transcriptional unit.

23. A method of preparing a vector having a preselected transcriptional unit comprising:
    (a) amplifying DNA or messenger RNA sequences comprising a preselected transcriptional unit using oligonucleotides which comprise a nucleic acid sequence obtained from the preselected transcriptional unit to yield a transcriptional unit cassette; and
    (b) inserting the transcriptional unit cassette into the vector of claim 1.

24. The method of claim 23 wherein the transcriptional unit cassette is inserted into the 3' LTR of the vector of claim 1, 5' of the sequences of step (d)(1) of the vector of claim 1.

25. The method of claim 23 wherein the transcriptional unit cassette is inserted 3' of the transcription initiation site in the 5' LTR.

26. The method of claim 23 wherein the transcriptional unit is a long terminal repeat.

27. The vector of claim 1 selected from the group consisting of VLP, VLCN, VLDN, VLPBN, VLPBNS, VLSN, VLPSNO, VLATGSAF, VLBEN, VLPPBGZ, VLIL2EN, VLATGF, VLATGR, VLOVBGH, VLSVP, VLATGSAR and VL30-MVM.

28. The vector of claim 11 wherein the DNA sequence is positioned 3' of the transcription initiation site in the 5' LTR.

29. A method for expressing a DNA sequence in a mammary cell in vitro comprising:
    (a) introducing a recombinant virus containing an RNA molecule into a mammary cell to yield a transformed mammary cell, wherein the RNA molecule is transcribed from the vector of claim 1, which vector further comprises a DNA sequence encoding a protein that is operably linked to a transcriptional promoter containing a hormone inducible transcription element and a mammary cell specific transcription element, wherein the DNA sequence is positioned 3' to the transcription initiation site in the 5' LTR of the vector, wherein a protein encoded by the DNA sequence in the transformed mammary cell is produced.

30. The method of claim 29 wherein the mammary-cell specific transcription element is selected from the group consisting of a casein promoter, a whey acidic protein promoter, and a lactoferrin promoter.

31. The method of claim 29 wherein exposing the transformed mammary cell to a hormone results in a change in the level of protein encoded by the DNA sequence.

32. A method of expressing in a recipient cell a toxin gene encoded by more than one exon in vitro comprising:
    (a) exposing the recipient cell to a recombinant virus containing an RNA molecule that is transcribed from the vector of claim 10 so that the virus is taken up by the recipient cell to yield a transformed recipient cell comprising a double-stranded cDNA obtained from the RNA molecule, wherein at least one nucleic acid sequence of the vector comprises an open reading frame that is a first exon of a toxin gene that is positioned 3' to the transcription initiation site in the 5' LTR of the vector and 3' to exons other than exon 1; and
    (b) culturing the cells under conditions suitable for expressing the toxin from the double-stranded DNA in the transformed recipient cell.

33. A method for delivering a DNA sequence to a mammary cell in vivo comprising introducing a recombinant virus containing an RNA molecule that is transcribed from the vector of claim 10 into a mammary cell in a nonhuman animal to yield a transformed mammary cell comprising a double-stranded cDNA obtained from the RNA molecule, wherein at least one nucleic acid sequence of the vector encodes a protein that is operably linked to a transcriptional promoter containing a hormone inducible transcription element and a mammary cell specific transcription element, wherein the DNA sequence is positioned 3' to the transcription initiation site in the 5' LTR of the vector.

34. The method of claim 33 wherein the mammary-cell specific transcription element is selected from the group consisting of a casein promoter, a whey acidic protein promoter, and a lactoferrin promoter.

35. The method of claim 33 wherein the transformed mammary cell is present in a mammary gland of a nonhuman mammal.

36. A method of delivering to a recipient cell a toxin gene encoded by more than one exon in vivo comprising:
    exposing the recipient cell to a recombinant virus containing an RNA molecule that is transcribed from the vector of claim 10 so that the virus is taken up by the recipient cell to yield a transformed recipient cell comprising a double-stranded cDNA obtained from the RNA molecule, wherein at least one nucleic acid sequence of the vector comprises an open reading frame encoding a first exon of a toxin gene that is positioned 3' to the transcription initiation site in the 5' LTR of the vector and 3' to exons other than exon 1.

37. The vector of claim 12 wherein the DNA sequence is positioned 3' of the transcription initiation site in the 5' LTR.

38. A method of obtaining transduced tumor infiltrating lymphocytes, comprising: introducing into autologous tumor infiltrating lymphocytes obtained from an individual a recombinant virus containing an RNA molecule that is transcribed from the vector of claim 10 so that the virus is taken up by the tumor infiltrating lymphocytes to yield tumor infiltrating lymphocytes comprising a double-stranded cDNA obtained from the RNA molecule, wherein at least one nucleic acid sequence comprises an open reading frame encoding a first exon of a toxin gene that is positioned 3' to the transcription initiation site in the 5' LTR of the vector and 3' to exons other than exon 1.

* * * * *

UNITED STATES PATENT AND TRADEMARK OFFICE
CERTIFICATE OF CORRECTION

PATENT NO. : 6,027,722
DATED : February 22, 2000
INVENTOR(S) : Hodgson

It is certified that error appears in the above-identified patent and that said Letters Patent is hereby corrected as shown below:

Column 3,
Lines 62 and 63, delete the paragraph break after "2231;".

Column 4,
Lines 12 and 13, delete the paragraph break after "supra).".

Column 9,
Lines 59 and 60, delete the paragraph break after "wherein".

Column 16,
Line 23, delete "3=PA317/LPPBN; 4=PA317/LIL2EN" and insert -- 3=PA317/VLPPBN; 4=PA317/VLIL2EN --, therefore.
Line 28, delete "PA317NLPPBN" and insert -- PA317/VLPPBN --, therefor.
Line 29, delete "PA317/LIL2EN" and insert -- PA317/VLIL2EN --, therefor.
Line 52, delete "PA317/NLPPBN" and insert -- PA317/VLPPBN --, therefor.
Line 55, delete "1) PA317NLPBN" and insert -- 1) PA317/VLPBN --; therefor.
Line 55, delete "2) PA317NLPPB" and insert -- 2) PA317/VLPPBN --, therefor.
Line 56, delete "4) HT108ONLPBN" and insert -- 4) HT1080/VLPBN --, therefor.
Line 57, delete "5) HT108ONLPPBN" and insert -- 5) HT1080/VLPPBN --, therefor.

Column 20,
Line 54, insert a paragraph break after "Sequences".

Column 23,
Line 32, delete "360°C" and insert -- 36°C --, therefor.

UNITED STATES PATENT AND TRADEMARK OFFICE
CERTIFICATE OF CORRECTION

PATENT NO.   : 6,027,722
DATED        : February 22, 2000
INVENTOR(S)  : Hodgson It is certified that error appears in the above-identified patent and that said Letters Patent is hereby corrected as shown below:

Column 27,
Line 15, insert a paragraph break after "Vector".

Column 48,
Line 66, delete "claim 10" and insert -- claim 13 --, therefor.

Signed and Sealed this

Twenty-seventh Day of November, 2001

Attest:

NICHOLAS P. GODICI
Attesting Officer    Acting Director of the United States Patent and Trademark Office

SEQUENCE LISTING

<160> NUMBER OF SEQ ID NOS: 16

<210> SEQ ID NO 1
<211> LENGTH: 39
<212> TYPE: DNA
<213> ORGANISM: Artificial Sequence
<220> FEATURE:
<223> OTHER INFORMATION: An oligonucleotide

<400> SEQUENCE: 1

-continued

```
tcagcagatc ttgaagaata aaaaattact ggcctcttg                             39

<210> SEQ ID NO 2
<211> LENGTH: 43
<212> TYPE: DNA
<213> ORGANISM: Artificial Sequence
<220> FEATURE:
<223> OTHER INFORMATION: An oligonucleotide

<400> SEQUENCE: 2
aagggcggcc gcttaattaa tccctgatcc tcccctgttc ctc                       43

<210> SEQ ID NO 3
<211> LENGTH: 36
<212> TYPE: DNA
<213> ORGANISM: Artificial Sequence
<220> FEATURE:
<223> OTHER INFORMATION: An oligonucleotide

<400> SEQUENCE: 3
actgcggccg catagacttc tgaaattcta agatta                               36

<210> SEQ ID NO 4
<211> LENGTH: 37
<212> TYPE: DNA
<213> ORGANISM: Artificial Sequence
<220> FEATURE:
<223> OTHER INFORMATION: An oligonucleotide

<400> SEQUENCE: 4
gaagatcttg aaagattttc gaattcccgg ccaatgc                              37

<210> SEQ ID NO 5
<211> LENGTH: 42
<212> TYPE: DNA
<213> ORGANISM: Artificial Sequence
<220> FEATURE:
<223> OTHER INFORMATION: An oligonucleotide

<400> SEQUENCE: 5
aaggcggccg cttaattaat ctaaggccgg ccaattgaga cc                        42

<210> SEQ ID NO 6
<211> LENGTH: 45
<212> TYPE: DNA
<213> ORGANISM: Artificial Sequence
<220> FEATURE:
<223> OTHER INFORMATION: An oligonucleotide

<400> SEQUENCE: 6
ggttaattaa ttagatctag catgattgaa caagatggat tgcac                     45

<210> SEQ ID NO 7
<211> LENGTH: 49
<212> TYPE: DNA
<213> ORGANISM: Artificial Sequence
<220> FEATURE:
<223> OTHER INFORMATION: An oligonucleotide

<400> SEQUENCE: 7
tacttaatta accatggatc cgttaactcc gaagcccaac ctttcatag                 49

<210> SEQ ID NO 8
<211> LENGTH: 80
<212> TYPE: DNA
<213> ORGANISM: Artificial Sequence
```

```
<220> FEATURE:
<223> OTHER INFORMATION: An oligonucleotide

<400> SEQUENCE: 8
tacttaatta accatggtct agtggatccg accttggaga gagagagtca gtgttaactc      60
cgaagcccaa cctttcatag                                                  80

<210> SEQ ID NO 9
<211> LENGTH: 34
<212> TYPE: DNA
<213> ORGANISM: Artificial Sequence
<220> FEATURE:
<223> OTHER INFORMATION: An oligonucleotide

<400> SEQUENCE: 9
tttagatctt ccctccccat tcccctccc agtt                                   34

<210> SEQ ID NO 10
<211> LENGTH: 22
<212> TYPE: DNA
<213> ORGANISM: Artificial Sequence
<220> FEATURE:
<223> OTHER INFORMATION: An oligonucleotide

<400> SEQUENCE: 10
cgaggtacct gaaagayyyy cg                                               22

<210> SEQ ID NO 11
<211> LENGTH: 19
<212> TYPE: DNA
<213> ORGANISM: Artificial Sequence
<220> FEATURE:
<223> OTHER INFORMATION: An oligonucleotide

<400> SEQUENCE: 11
gggttcagat cttgatcag                                                   19

<210> SEQ ID NO 12
<211> LENGTH: 97
<212> TYPE: DNA
<213> ORGANISM: Artificial Sequence
<220> FEATURE:
<223> OTHER INFORMATION: An oligonucleotide

<400> SEQUENCE: 12
taagcggccg ctagacttct gaaattctaa gattagaatt atttacaaga agaagtgggg      60
aatgaagaat aaaaaattct gatcaagatc tgaaccc                               97

<210> SEQ ID NO 13
<211> LENGTH: 66
<212> TYPE: DNA
<213> ORGANISM: Artificial Sequence
<220> FEATURE:
<223> OTHER INFORMATION: An oligonucleotide

<400> SEQUENCE: 13
taagcggccg ctagacttct gaaattctaa gattagaatt atttacaaga agaagtgggg      60
aatgaa                                                                 66

<210> SEQ ID NO 14
<211> LENGTH: 36
<212> TYPE: DNA
<213> ORGANISM: Artificial Sequence
<220> FEATURE:
```

-continued

```
<223> OTHER INFORMATION: An oligonucleotide

<400> SEQUENCE: 14
cgaggtacct gaaagatttt cgaattcccg gccaat                              36

<210> SEQ ID NO 15
<211> LENGTH: 73
<212> TYPE: DNA
<213> ORGANISM: Artificial Sequence
<220> FEATURE:
<223> OTHER INFORMATION: An oligonucleotide

<400> SEQUENCE: 15
cggaaatgat catggaatga taagatgacc taactaatag cccatctctc caagatcgat    60
caggcctaga tct                                                       73

<210> SEQ ID NO 16
<211> LENGTH: 73
<212> TYPE: DNA
<213> ORGANISM: Artificial Sequence
<220> FEATURE:
<223> OTHER INFORMATION: An oligonucleotide

<400> SEQUENCE: 16
cgagatctag gcctgatcga tcttggagag atgggctatt agttaggtca tcttatcatt    60
ccatgatcat ttc                                                       73
```